(12) United States Patent
Iwamoto et al.

(10) Patent No.: US 7,744,818 B2
(45) Date of Patent: Jun. 29, 2010

(54) STATIONARY PHASE MATERIALS FOR MICRO GAS ANALYZER

(75) Inventors: Nancy E. Iwamoto, Ramona, CA (US); Teresa A. Ramos, San Jose, CA (US); Robert R. Roth, Sunnyvale, CA (US); Ulrich Bonne, Hopkins, MN (US)

(73) Assignee: Honeywell International Inc., Morristown, NJ (US)

( * ) Notice: Subject to any disclaimer, the term of this patent is extended or adjusted under 35 U.S.C. 154(b) by 568 days.

(21) Appl. No.: 11/276,399

(22) Filed: Feb. 27, 2006

(65) Prior Publication Data

US 2006/0228261 A1   Oct. 12, 2006

Related U.S. Application Data

(60) Provisional application No. 60/657,557, filed on Feb. 28, 2005.

(51) Int. Cl.
*G01N 30/96* (2006.01)
*B32B 5/02* (2006.01)

(52) U.S. Cl. ............................ 422/88; 73/23.2; 436/172

(58) Field of Classification Search .................... 422/88
See application file for complete search history.

(56) References Cited

U.S. PATENT DOCUMENTS 5,879,794 A * 3/1999 Korleski, Jr. .............. 428/317.1
6,393,894 B1   5/2002 Bonne et al.
2004/0011255 A1   1/2004 Giangrasso
2004/0242023 A1* 12/2004 Yan et al. .................... 438/780

OTHER PUBLICATIONS

Poppe, "Mass transfer in regtangular chromatographic channels," Journal of Chromatography A., pp. 3-17, Mar. 2002.
Gross et al., "High-Speed Gas Chromatography Using Synchronized Dual-Valve Injection," Analytical Chemistry, Vo. 76. No. 13, pp. 3517-3524, Jul. 1, 2004.
Lambertus et al., "Design, Fabrication, and Evaluation of Microfabricated Columns for Gas Chromatography," Analytical Chemistry, vol. 76, No. 9, pp. 2629-2637, May 1, 2004.
Born et al., Electromagnetic Potentials and Polarization, Principles of Optics, pp. 71-108, Fifth Edition, 1975.
Brown et al., "An Experimental Study of Oscillating Flow With Absorbent Polymers for Use in Respirators," The American Industrial Hygiene Association Journal, 24 pages, May 1996.

(Continued)

*Primary Examiner*—Krishnan S Menon
*Assistant Examiner*—Dirk Bass
(74) *Attorney, Agent, or Firm*—Crompton Seager & Tufte LLC

(57) ABSTRACT

Selecting a stationary phase for a fluid analyzer using certain criteria to determine an appropriate material for use in, for instance, a micro fluid analyzer. High absorption of an analyte or sample, low water sorbency and high porosity or permeability of the material may be sought. A selected material may incorporate a toughening agent using a neutral leaving group. A selected material may have a capping agent to promote hydrophobicity. A selected material may be a hydrophobic polymer. The selection of a stationary phase may involve molecular modeling.

5 Claims, 82 Drawing Sheets

OTHER PUBLICATIONS http://www.deltacnt.com, "Dielectric Constants of Various Materials," Delta Controls Corporation, 43 pages, prior to filing date of present application Feb. 27, 2006.

http://webbook.nist.gov., "Welcome to the NIST WebBook," 2 pages, printed Aug. 2, 2006.

http://chemfinder.combridgesoft.com, "Chemfinder.Com," 2 pages, printed Aug. 2, 2006.

Doleman et al., "Trends in odor intensity for human and electronic noses: Relative roles of odorant vapor pressure vs. molecularly specific odorant binding," Proceedings of the National Academy of Sciences, vol. 95, pp. 5442-5447, May 1998.

Patel et al., "Chemicapacitive microsensors for volatile organic compound detection," Sensors and Actuators, B 96, pp. 541-553, Dec. 2003.

Bonne et al., "PHASED: a Faster, Smarter & More Affordable Analysis Device," 25 pages, prior to filing date of present application Feb. 27, 2006.

Grate et al., "Comparisons of Polymer/Gas Partition Coefficients Calculated from Responses of Thickness Shear Mode and Surface Acoustic Wave Vapor Sensors," Analytical Chemistry, vol. 70, No. 1, pp. 199-203, Jan. 1, 1998.

McGill et al., "Choosing polymer coatings for chemical sensors," The American Chemical Society, pp. 27-37, Sep. 1994.

Borman, "Better Detector for Plastic Explosives," Chemical, vol. 81, No. 34, 1 page, Aug. 25, 2003.

Bonne et al., PHASED Feasibility Demonstration, Honeywell, pp. 1-24, prior to filing date of current application Feb. 27, 2006.

Saridara et al., "Chromatography on Self-Assembled Carbon Nanotubes," Analytical Chemistry, vol. 77, No. 21, pp. 7094-7097, Nov. 1, 2005.

Iwamoto et al., "Molecular Dynamics and Discrete Element Modeling Studies of Underfill," The International Journal of Microcircuits and Electronic Packaging, vol. 21, No. 4, pp. 322-328, Fourth Quarter 1998.

Search Results for N. Iwamoto on "diaceto or diformidosilane" 20 pages, printed Feb. 18, 2006.

Cases et al., "Chromatography Theory," entire book, 475 pages, Copyright 2002.

* cited by examiner

Comparison of MGA Performance* with H2 or Air Carrier Gas

| | | N2(Air) | H2 | Ratio H2/N2 | He | Ratio He/N2 |
|---|---|---|---|---|---|---|
| A | μGC Pressure Drop (Viscosity in μP) | 176.5 | 88.9 | 0.50 | 197.2 | 1.117 |
| B | μGC Pressure Drop (Mass Diffussivity in cm2/s) Heat Loss | 0.15 | 0.56 | 3.7 | 0.404 | 2.69 |
| C | (Thermal Cond., μcal/(sKcm) MGA Energy/Analysis | 60.4 | 439 Reduced Pumping** | ~ 7.3 | 370 | 6.13 |
| D | (Joule/Analysis) | 1 | | ~ 0.8x1.3 | 0.137 | 0.163 |
| | MGA Pre-Concentration | | More Complex | Less Pre-C needed | More Complex, and He storage needed | Less Pre-C needed |
| E | (Sample Inject. into H2) MDL, Min. Detection Limit | 1 | 0.13-TCD,MDD 0.9-ITMS | 0.13-TCD,MDD 0.9-ITMS | 0.16-TCD,MDD 0.2-ITMS | 0.16-TCD,MDD 0.2-ITMS |
| F | Reduced Background Noise Detector Signal Processing | 1 | Less Complex | Lower MDL | Less Complex | Lower MDL |
| G | (N2, O2 Interference) Separation, Peak Capacity | 1 | | | | |
| H | Optimal flow in cm/s / Resolution | 98 / 11.5 | 364 / 11.5 | 3.7 / 1 | 263 / 11.5 | 2.7 / 1 |
| G | Leverage CI/API/PRT Ionization | 1 | 1 | 1 | 1 | 1 |

* Net Change: More complex; (2x more Δp=AxB); 1.1x more energy/analysis;
~5x lower MDL(Min.Det.Limit) of TCD, MDD, ITMS
**Due to provided H2-pressure

FIGURE 3

Retention indices and $\Delta I_R$ –values of differently polar C8 compounds on apolar polydimethyl siloxane (OV1) and polar polyethylenglycol (PEG) as stationary phase

| Compound | $I_R$ (OV1) | $I_R$ (PEG) | $\Delta I_R = I_R^{polar} - I_R^{unpolar}$ |
|---|---|---|---|
| n-octane | 800 | 800 | 0 |
| n-dibutylether | 864 | 966 | 102 |
| n-hexylacetate | 963 | 1101 | 138 |
| n-octanon-2 | 957 | 1295 | 338 |
| n-octanol-1 | 1038 | 1545 | 507 |

FIGURE 4

Comparison of Interaction Enthalpies, ΔH, before and after Hydration of Several Stationary Phase Films, for Dodecane and PMMD

| Correlation between Experimental and Calculated Phase Equilibrium or K-Values |||||||
| The listed K-values are for a common std. temperature of 298 K. |||||||
| | | | PDMS / TRX-1 / DB-1 ||| |
| | Boil.Pt. | ε[10] | Equil - K Expt. | Equil - K Calc(Tb,e) | ΔH(vap) kJ[11] |
| | K | | | | |
| A | | | | | |
| Methanol | 337.7 | 33.0 | 17.0 | 23 | |
| Ethanol | 351.2 | 25.0 | 37.4 | 43 | 38.56 |
| Acetone | 329.4 | 21.0 | 45.6 | 26 | |
| Ethylacetate | 350.2 | 6.0 | 171.8 | 138 | |
| Benzene | 353.3 | 2.3 | 285.0 | 372 | 30.72 |
| Trichloroethyl. | 359.9 | 3.4 | 389.1 | 318 | |
| Toluene | 383.9 | 2.4 | 746.5 | 1013 | |
| Octane | 398.8 | 2.0 | 1177.9 | 2094 | 34.41 |
| Decane | 447.2 | 2.0 | 8944.9 | 10512 | 38.75 |
| Dodecane | 486.2 | 2.0 | 60000.0 | 38658 | |
| Chlorobenzene | 404.8 | 5.6 | 1762.3 | 862 | 35.19 |
| B | | | | | |
| Pentane | 309.2 | 1.8 | 57.3 | 97 | |
| Hexane | 341.9 | 1.9 | 156.9 | 297 | 28.85 |
| Heptane | 371.6 | 2.1 | 443.2 | 760 | |
| Dichloromethane | 313.9 | 9.1 | 70.0 | 30 | |
| 2-Butanone | 352.8 | 18.5 | 136.8 | 58 | |
| 2-Pentanone | 376.5 | 15.4 | 340.4 | 138 | 33.44 |
| 2-Heptanone | | | | | 39.50 |
| 1,1,1-Trichloroethane | 347.3 | 7.5 | 229.0 | 104 | |
| Ethyl butyrate | 393.2 | 5.1 | 1105.9 | 652 | |
| Cycloheptane | 391.7 | 1.8 | 1017.9 | 1783 | |
| Butyl acetate | 394.2 | 7 | 1263.9 | 495 | |
| Butanol | | | | | 43.29 |
| Pentanol | | | | | 44.36 |
| Octanol | 467.7 | 5.10 | 1528.3 | 6988 | |
| DMMP | 454.0 | 3.3 | 2322.0 | 7411 | 53.63 |
| DEEP | 471.0 | 2.1 | 20110.1 | 22019 | 58.35 |
| C | | | | | |
| Methane | 111.6 | 1.7 | 0.0435 | 0.0486 | |
| Ethane | 184.6 | 1.8 | 0.3839 | 0.9213 | |
| Ethylene | 169.4 | 2.0 | | 0.4793 | |
| Acetylene | 189.4 | 2.0 | | 1.0466 | |
| Propane | 231.1 | 2.0 | 7.1931 | 5.1167 | |
| Butane | 272.7 | 2.0 | 15.5344 | 23.7914 | |
| Carbon dioxide | 194.6 | 1.6 | | 1.4600 | |
| Carbon monoxide | | | | | |
| Hydrogen | | | | 0.0007 | |
| Nitrogen | | | | 0.0116 | |
| | Boil.Pt. | ε | Equil - K | Equil - K | ΔH in kJ |

FIGURE 10

Bisperfluorobutanol group--SiOH Side

| | MW | SiOH unhydr | SiOH hydr pre-equil | SiOH hyr no pre-equil |
|---|---|---|---|---|
| hd | 159 | -21.50 | -9.61 | -27.90 |
| vx | 224 | -108.13 | -94.27 | -112.56 |
| dmmp | 108 | -3.77 | 10.48 | -7.81 |
| demp | 152 | -27.60 | -20.61 | -38.90 |
| dimp | 180 | -22.40 | -2.39 | -20.68 |
| deep | 166 | -25.77 | -11.22 | -29.51 |
| tbp | 266 | -17.06 | -11.75 | -30.04 |
| cl2co | 99 | -6.68 | 7.06 | -11.23 |
| clcn | 62 | -5.76 | 9.42 | -8.87 |
| hcn | 27 | -7.56 | 7.38 | -10.91 |
| h2s | 34 | -3.48 | 10.65 | -7.63 |

FIGURE 85

TrifluoropropylMethylSilyl Group--SiOH Side

| | MW | SiOH unhydr | SiOH hydr pre-equil | SiOH hyr no pre-equil |
|---|---|---|---|---|
| hd | 159 | -7.97 | -7.43 | -12.99 |
| vx | 224 | 15.18 | 24.22 | 18.66 |
| vx | 224 | -86.19 | -75.14 | -80.71 |
| dmmp | 108 | -2.45 | 1.67 | -3.90 |
| demp | 152 | -13.27 | -10.81 | -16.37 |
| dimp | 180 | -13.55 | -10.73 | -16.30 |
| deep | 166 | -10.84 | -0.90 | -6.47 |
| tbp | 266 | -22.09 | -13.17 | -18.74 |
| cl2co | 99 | -7.60 | -5.54 | -11.10 |
| clcn | 62 | -3.47 | -4.01 | -9.57 |
| hcn | 27 | -4.63 | -6.75 | -12.31 |
| h2s | 34 | -3.84 | -3.00 | -8.56 |

FIGURE 86

DifluoropropanolMethylSilyl Group -- SiOH side

| | MW | SiOH unhydr | SiOH hydr pre-equil | SiOH hyr no pre-equil |
|---|---|---|---|---|
| hd | 159 | -11.97 | -8.92 | -16.45 |
| vx | 224 | -14.33 | 23.01 | 15.48 |
| vx | 224 | -25.24 | -75.52 | -83.05 |
| dmmp | 108 | -4.36 | -6.53 | -14.06 |
| demp | 152 | -14.66 | -6.59 | -14.11 |
| dimp | 180 | -12.23 | -14.93 | -22.46 |
| deep | 166 | -14.65 | -9.26 | -16.79 |
| tbp | 266 | -23.86 | -17.20 | -24.73 |
| cl2co | 99 | -8.65 | -4.46 | -11.99 |
| clcn | 62 | -6.65 | -23.07 | -30.59 |
| hcn | 27 | -9.67 | -10.11 | -17.64 |
| h2s | 34 | -5.46 | -2.72 | -10.25 |

FIGURE 87

Dimethylsilyl Group = "TA" on SiOH side

| | MW | SiO unhydr | SiO hydr pre-equil | SiO hyr no pre-equil |
|---|---|---|---|---|
| hd | 159 | -11.67 | -53.01 | -58.13 |
| vx | 224 | -19.15 | -18.52 | -23.64 |
| dmmp | 108 | 15.90 | -3.15 | -8.27 |
| demp | 152 | -15.97 | -10.35 | -15.47 |
| dimp | 180 | -13.53 | -8.08 | -13.20 |
| deep | 166 | -9.07 | -8.18 | -13.30 |
| tbp | 266 | -16.04 | -17.56 | -22.67 |
| cl2co | 99 | -5.28 | -4.51 | -9.63 |
| clcn | 62 | -8.37 | -2.19 | -7.31 |
| hcn | 27 | -8.37 | -3.05 | -8.17 |
| h2s | 34 | -2.68 | -2.24 | -7.36 |

FIGURE 88

Nanoglass on SiOH side

| | MW | SiOH unhydr | SiOH hydr pre-equil | SiOH hyr no pre-equil |
|---|---|---|---|---|
| hd | 159 | -24.67 | -1.00 | -16.76 |
| vx | 224 | -26.79 | -15.57 | -31.33 |
| dmmp | 108 | -2.32 | 9.51 | -6.25 |
| demp | 152 | -28.38 | -17.06 | -32.82 |
| dimp | 180 | -29.61 | -13.19 | -28.95 |
| deep | 166 | -13.87 | -2.73 | -18.49 |
| tbp | 266 | -13.38 | -6.18 | -21.94 |
| cl2co | 99 | -8.54 | 4.38 | -11.38 |
| clcn | 62 | -5.27 | 6.43 | -9.33 |
| hcn | 27 | -8.09 | 2.68 | -13.08 |
| h2s | 34 | -1.24 | 7.16 | -8.60 |

FIGURE 89

Nanoglass on SiO Side

| | MW | NG SiO unhydr | NG SiO hydr pre-equil | NG SiO hyr no pre-equil |
|---|---|---|---|---|
| hd | 159.00 | -25.27 | -18.91 | -23.95 |
| vx | 224.00 | -30.93 | -30.47 | -35.51 |
| dmmp | 108.00 | -0.45 | -11.66 | -16.70 |
| demp | 152.00 | -11.37 | -25.34 | -30.38 |
| dimp | 180.00 | -20.97 | -20.62 | -25.66 |
| deep | 166.00 | -20.57 | -19.75 | -24.79 |
| tbp | 266.00 | -27.78 | -24.64 | -29.68 |
| cl2co | 99.00 | -12.98 | -12.75 | -17.79 |
| clcn | 62.00 | -15.93 | -6.73 | -11.77 |
| hcn | 27.00 | -13.72 | -19.74 | -24.78 |
| h2s | 34.00 | -13.72 | -21.10 | -26.14 |

FIGURE 90

DimethylSilyl Group = "TA" on SiOH Side

| | MW | SiOH unhydr | SiOH hydr pre-equil | SiOH hyr no pre-equil |
|---|---|---|---|---|
| hd | 159 | -11.74 | -9.73 | -37.90 |
| vx | 224 | -11.12 | 11.84 | -16.34 |
| dmmp | 108 | 0.15 | 20.85 | -7.33 |
| demp | 152 | -16.09 | 17.18 | -10.99 |
| dimp | 180 | -17.13 | -6.65 | -34.83 |
| deep | 166 | -8.60 | 22.60 | -5.57 |
| tbp | 266 | -15.22 | 12.39 | -15.79 |
| cl2co | 99 | -10.50 | 15.66 | -12.51 |
| clcn | 62 | -5.37 | -3.99 | -32.17 |
| hcn | 27 | -7.33 | 15.64 | -12.54 |
| h2s | 34 | -2.57 | 20.82 | -7.36 |

FIGURE 91

| | MW | tfe unhydr | tfe hydr pre-equil | tfe hyr no pre-equil |
|---|---|---|---|---|
| hd | 159 | -9.98 | -8.83 | -31.39 |
| vx | 224 | -18.97 | -20.25 | -42.81 |
| dmmp | 108 | -15.00 | -12.76 | -35.32 |
| demp | 152 | -20.00 | -11.93 | -34.49 |
| dimp | 180 | -22.78 | -13.46 | -36.02 |
| deep | 166 | -16.07 | -17.72 | -40.28 |
| tbp | 266 | -21.43 | -21.79 | -44.34 |
| cl2co | 99 | -9.43 | -9.90 | -32.45 |
| clcn | 62 | -7.42 | -6.31 | -28.86 |
| hcn | 27 | -7.73 | -5.75 | -28.31 |
| h2s | 34 | -4.63 | -3.00 | -25.55 |

FIGURE 94

Bisperfluorobutanol group-SiOH Side

| | MW | SiOH unhydr | SiOH hydr pre-equil | SiOH hyr no pre-equil |
|---|---|---|---|---|
| hd | 159 | -21.50 | -9.61 | -27.90 |
| vx | 224 | -108.13 | -94.27 | -112.56 |
| dmmp | 108 | -3.77 | 10.48 | -7.81 |
| demp | 152 | -27.60 | -20.61 | -38.90 |
| dimp | 180 | -22.40 | -2.39 | -20.68 |
| deep | 166 | -25.77 | -11.22 | -29.51 |
| tbp | 266 | -17.06 | -11.75 | -30.04 |
| cl2co | 99 | -6.68 | 7.06 | -11.23 |
| clcn | 62 | -5.76 | 9.42 | -8.87 |
| hcn | 27 | -7.56 | 7.38 | -10.91 |
| h2s | 34 | -3.48 | 10.65 | -7.63 |

FIGURE 95

TrifluoropropylMethylSilyl Group--SiOH Side

| | MW | SiOH unhydr | SiOH hydr pre-equil | SiOH hyr no pre-equil |
|---|---|---|---|---|
| hd | 159 | -7.97 | -7.43 | -12.99 |
| vx | 224 | 15.18 | 24.22 | 18.66 |
| vx | 224 | -86.19 | -75.14 | -80.71 |
| dmmp | 108 | -2.45 | 1.67 | -3.90 |
| demp | 152 | -13.27 | -10.81 | -16.37 |
| dim

| kcal/mole | Avatrel Unhydrated | Avatrel Hydrated (pre-equil) | Avatrel Hydrated (not pre-equil) |
|---|---|---|---|
| hd | -44.70 | -32.54 | -72.46 |
| vx | -90.59 | -25.39 | -65.31 |
| dmmp | -46.28 | -11.99 | -51.91 |
| demp | -71.33 | -14.55 | -54.47 |
| dimp | -53.96 | -23.69 | -63.61 |
| deep | -51.12 | -16.96 | -56.88 |
| tbp | -80.34 | -58.09 | -98.01 |
| clcn | -40.01 | -4.68 | -44.59 |
| hcn | -39.84 | -3.96 | -43.87 |
| h2s | -36.05 | -1.08 | -41.00 |
| cl2co | -41.78 | -5.76 | -45.67 |
| hexane | -45.41 | -22.16 | -62.08 |
| octane | -48.64 | -10.64 | -50.55 |
| decane | -48.66 | -22.28 | -62.20 |
| ethanol | -40.27 | -16.76 | -56.67 |

FIGURE 107

| kcal/mole | SU8 Unhydrated | SU8 Hydrated (pre-equil) | SU8 Hydrated (not pre-equil) |
|---|---|---|---|
| hd | -18.74 | -11.16 | -20.00 |
| vx | -25.86 | -29.95 | -38.79 |
| dmmp | -25.00 | -14.71 | -23.54 |
| demp | -23.67 | -19.81 | -28.65 |
| dimp | -27.81 | -25.03 | -33.86 |
| deep | -27.89 | -20.40 | -29.23 |
| tbp | -28.77 | -23.38 | -32.21 |
| clcn | -8.09 | -6.03 | -14.86 |
| hcn | -8.54 | -7.36 | -16.19 |
| h2s | -3.79 | -2.78 | -11.61 |
| cl2co | -9.18 | -8.45 | -17.28 |
| hexane | -15.00 | -9.28 | -18.12 |
| octane | -21.02 | -16.61 | -25.45 |
| decane | -19.39 | -20.54 | -29.37 |
| ethanol | -11.73 | -8.29 | -17.13 |

FIGURE 108

| | NG SiO side | | | NG SiOH Side | | | Graphite/CNT | | |
|---|---|---|---|---|---|---|---|---|---|
| | unhydr | hydr pre-equil | hyr no pre-equil | unhydr | hydr pre-equil | hyr no pre-equil | unhydr | hydr pre-equil | hyr no pre-equil |
| hd | -25.27 | -18.91 | -23.95 | -24.67 | -1.00 | -16.76 | -16.85 | -10.36 | -34.65 |
| vx | -30.93 | -30.47 | -35.51 | -26.79 | -15.57 | -31.33 | -30.33 | -29.55 | -53.84 |
| dmmp | -0.45 | -11.66 | -16.70 | -2.32 | 9.51 | -6.25 | -16.50 | -23.47 | -47.75 |
| demp | -11.37 | -25.34 | -30.38 | -28.38 | -17.06 | -32.82 | -23.54 | -23.18 | -47.47 |
| dimp | -20.97 | -20.62 | -25.66 | -29.61 | -13.19 | -28.95 | -25.88 | -27.92 | -52.21 |
| deep | -20.57 | -19.75 | -24.79 | -13.87 | -2.73 | -18.49 | -19.74 | -24.66 | -48.95 |
| tbp | -27.78 | -24.64 | -29.68 | -13.38 | -6.18 | -21.94 | -24.04 | -29.95 | -54.24 |
| clcn | -15.93 | -6.73 | -11.77 | -5.27 | 6.43 | -9.33 | -7.49 | -9.50 | -33.78 |
| hcn | -13.72 | -19.74 | -24.78 | -8.09 | 2.68 | -13.08 | -6.44 | -10.12 | -34.41 |
| h2s | -13.72 | -21.10 | -26.14 | -1.24 | 7.16 | -8.60 | -3.46 | -4.85 | -29.14 |
| cl2co | -12.98 | -12.75 | -17.79 | -8.54 | 4.38 | -11.38 | -9.07 | -13.38 | -37.67 |
| hexane | -17.61 | -11.59 | -6.55 | -9.98 | -25.82 | -10.06 | -17.93 | -8.58 | -32.87 |
| octane | -19.46 | -26.22 | -21.18 | -22.57 | -16.86 | -1.10 | -23.46 | -13.74 | -38.03 |
| decane | -19.26 | -18.57 | -22.46 | -23.63 | -14.93 | 0.83 | -24.32 | -16.24 | -40.53 |
| ethanol | -14.09 | -22.47 | -17.43 | -17.61 | -12.49 | 3.27 | -7.36 | -6.79 | -31.08 |

FIGURE 109

| | Tetrafluoroethylene/Teflon | | | Trifluoropropyl MethylSilyl Group—SiOH Side | | | GX3P | | |
|---|---|---|---|---|---|---|---|---|---|
| | unhydr | hydr pre-equil | hyr no pre-equil | unhydr | hydr pre-equil | hyr no pre-equil | unhydr | hydr pre-equil | hyr no pre-equil |
| hd | -9.98 | -8.83 | -31.39 | -7.97 | -7.43 | -12.99 | -64.77 | -42.98 | -51.59 |
| vx | -18.97 | -20.25 | -42.81 | -86.19 | -75.14 | -80.71 | -132.19 | -63.09 | -71.69 |
| dmmp | -15.00 | -12.76 | -35.32 | -2.45 | 1.67 | -3.90 | | | |
| demp | -20.00 | -11.93 | -34.49 | -13.27 | -10.81 | -16.37 | | | |
| dimp | -22.78 | -13.46 | -36.02 | -13.55 | -10.73 | -16.30 | | | |
| deep | -16.07 | -17.72 | -40.28 | -10.84 | -0.90 | -6.47 | | | |
| tbp | -21.43 | -21.79 | -44.34 | -22.09 | -13.17 | -18.74 | | | |
| clcn | -7.42 | -6.31 | -28.86 | -3.47 | -4.01 | -9.57 | | | |
| hcn | -7.73 | -5.75 | -28.31 | -4.63 | -6.75 | -12.31 | | | |
| h2s | -4.63 | -3.00 | -25.55 | -3.84 | -3.00 | -8.56 | | | |
| cl2co | -9.43 | -9.90 | -32.45 | -7.60 | -5.54 | -11.10 | | | |
| hexane | | | | | | | -10.14 | -18.21 | -26.82 |
| octane | | | | | | | -15.88 | -20.60 | -29.20 |
| decane | | | | | | | -22.02 | -20.86 | -29.46 |
| ethanol | | | | | | | -10.12 | -8.33 | -16.93 |
| dmhp | | | | | | | -30.76 | -29.02 | -37.63 |

FIGURE 110

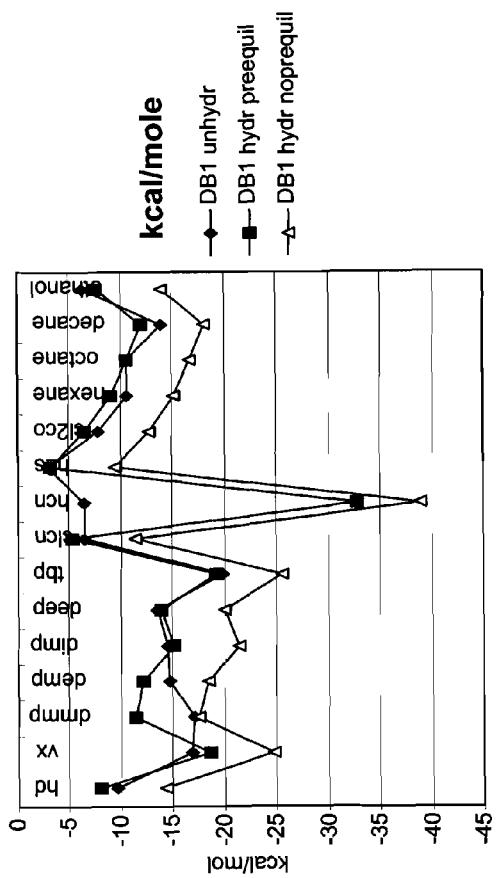
FIGURE 111
| kcal/mole | DB1 unhydr | DB1 hydr preequil | DB1 hydr noprequil |
|---|---|---|---|
| hd | -9.72 | -8.13 | -14.30 |
| vx | -16.85 | -18.60 | -24.77 |
| dmmp | -17.15 | -11.41 | -17.58 |
| demp | -14.70 | -12.24 | -18.41 |
| dimp | -14.58 | -15.21 | -21.38 |
| deep | -13.60 | -13.97 | -20.14 |
| tbp | -19.80 | -19.34 | -25.51 |
| clcn | -6.52 | -5.21 | -11.38 |
| hcn | -6.52 | -32.82 | -38.99 |
| h2s | -2.88 | -3.19 | -9.36 |
| cl2co | -7.95 | -6.52 | -12.69 |
| hexane | -10.57 | -9.04 | -15.21 |
| octane | -10.58 | -10.54 | -16.71 |
| decane | -13.92 | -11.94 | -18.11 |
| ethanol | -6.32 | -7.74 | -13.91 |
FIGURE 112
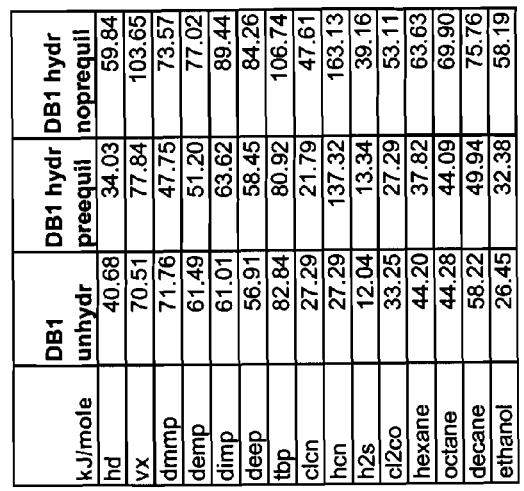
| kJ/mole | DB1 unhydr | DB1 hydr preequil | DB1 hydr noprequil |
|---|---|---|---|
| hd | 40.68 | 34.03 | 59.84 |
| vx | 70.51 | 77.84 | 103.65 |
| dmmp | 71.76 | 47.75 | 73.57 |
| demp | 61.49 | 51.20 | 77.02 |
| dimp | 61.01 | 63.62 | 89.44 |
| deep | 56.91 | 58.45 | 84.26 |
| tbp | 82.84 | 80.92 | 106.74 |
| clcn | 27.29 | 21.79 | 47.61 |
| hcn | 27.29 | 137.32 | 163.13 |
| h2s | 12.04 | 13.34 | 39.16 |
| cl2co | 33.25 | 27.29 | 53.11 |
| hexane | 44.20 | 37.82 | 63.63 |
| octane | 44.28 | 44.09 | 69.90 |
| decane | 58.22 | 49.94 | 75.76 |
| ethanol | 26.45 | 32.38 | 58.19 |
FIGURE 113

Regular NGE-SiOH side

| | NG SiOH unh | NG SiOH hydr pre-e | hyr no pre-equil |
|---|---|---|---|
| hd | -24.67 | -1.00 | -16.76 |
| vx | -26.79 | -15.57 | -31.33 |
| dmmp | -2.32 | 9.51 | -6.25 |
| demp | -28.38 | -17.06 | -32.82 |
| dimp | -29.61 | -13.19 | -28.95 |
| deep | -13.87 | -2.73 | -18.49 |
| tbp | -13.38 | -6.18 | -21.94 |
| cl2co | -8.54 | 4.38 | -11.38 |
| clcn | -5.27 | 6.43 | -9.33 |
| hcn | -8.09 | 2.68 | -13.08 |
| h2s | -1.24 | 7.16 | -8.60 |

Dimethyl substituted NGE

SiOH Side

| | SiOH unhydr | r pre-equil | o pre-equil |
|---|---|---|---|
| hd | -11.7402 | -9.72647 | -37.9013 |
| vx | -11.1215 | 11.83879 | -16.336 |
| dmmp | 0.154905 | 20.84698 | -7.32781 |
| demp | -16.0876 | 17.18279 | -10.992 |
| dimp | -17.1318 | -6.65133 | -34.8261 |
| deep | -8.60467 | 22.60469 | -5.5701 |
| tbp | -15.2239 | 12.38729 | -15.7875 |
| cl2co | -10.5042 | 15.6638 | -12.511 |
| clcn | -5.36715 | -3.99355 | -32.1683 |
| hcn | -7.32848 | 15.6355 | -12.5393 |
| h2s | -2.56695 | 20.81817 | -7.35662 |

| | MW | tfe unhydr | tfe hydr pre-equil | tfe hyr no pre-equil |
|---|---|---|---|---|
| hd | 159 | -9.98 | -8.83 | -31.39 |
| vx | 224 | -18.97 | -20.25 | -42.81 |
| dmmp | 108 | -15.00 | -12.76 | -35.32 |
| demp | 152 | -20.00 | -11.93 | -34.49 |
| dimp | 180 | -22.78 | -13.46 | -36.02 |
| deep | 166 | -16.07 | -17.72 | -40.28 |
| tbp | 266 | -21.43 | -21.79 | -44.34 |
| cl2co | 99 | -9.43 | -9.90 | -32.45 |
| clcn | 62 | -7.42 | -6.31 | -28.86 |
| hcn | 27 | -7.73 | -5.75 | -28.31 |
| h2s | 34 | -4.63 | -3.00 | -25.55 |

Trifluoropropylmethylsilyl Group--SiOH Side

| | SiOH unhydr | tr pre-equil | hyr no pre-equil |
|---|---|---|---|
| hd | -7.97278 | -7.4262 | -12.990912 |
| vx av | -35.50 | -25.46 | -31.02 |
| dmmp | -2.45325 | -8.17541 | -3.897153 |
| demp | -13.2746 | -10.8082 | -16.372945 |
| dimp | -13.5507 | -10.7337 | -16.298399 |
| deep | -10.8355 | -0.9033 | -6.468006 |
| tbp | -22.0895 | -13.1744 | -18.739119 |
| cl2co | -7.5999 | -5.53875 | -11.10346 |
| clcn | -3.47071 | -4.006 | -9.570713 |
| hcn | -4.63181 | -6.7499 | -12.314615 |
| h2s | -3.8367 | -2.99576 | -8.560474 |
| hexane | -7.3102 | -2.41142 | -7.976133 |
| octane | -10.0191 | -4.55157 | -10.116279 |
| decane | -8.63883 | -5.30938 | -10.874088 |
| etoh | -9.76525 | -8.21662 | -13.781334 |

| kcal/mole | Avatrel Unhydrated | Avatrel Hydrated (pre-equil) | Avatrel Hydrated (not pre-equil) |
|---|---|---|---|
| hd | -44.70 | -32.54 | -72.46 |
| vx | -90.59 | -25.39 | -65.31 |
| dmmp | -46.28 | -11.99 | -51.91 |
| demp | -71.33 | -14.55 | -54.47 |
| dimp | -53.96 | -23.69 | -63.61 |
| deep | -51.12 | -16.96 | -56.88 |
| tbp | -80.34 | -58.09 | -98.01 |
| clcn | -40.01 | -4.68 | -44.59 |
| hcn | -39.84 | -3.96 | -43.87 |
| h2s | -36.05 | -1.08 | -41.00 |
| cl2co | -41.78 | -5.76 | -45.67 |
| hexane | -45.41 | -22.16 | -62.08 |
| octane | -48.64 | -10.64 | -50.55 |
| decane | -48.66 | -22.28 | -62.20 |
| ethanol | -40.27 | -16.76 | -56.67 |

| kcal/mole | SU8 Unhydrat | SU8 Hydrated (pre-e | SU8 Hydrated (n |
|---|---|---|---|
| hd | -18.74 | -11.16 | -20.00 |
| vx | -25.86 | -29.95 | -38.79 |
| dmmp | -25.00 | -14.71 | -23.54 |
| demp | -23.67 | -19.81 | -28.65 |
| dimp | -27.81 | -25.03 | -33.86 |
| deep | -27.89 | -20.40 | -29.23 |
| tbp | -28.77 | -23.38 | -32.21 |
| clcn | -8.09 | -6.03 | -14.86 |
| hcn | -8.54 | -7.36 | -16.19 |
| h2s | -3.79 | -2.78 | -11.61 |
| cl2co | -9.18 | -8.45 | -17.28 |
| hexane | -15.00 | -9.28 | -18.12 |
| octane | -21.02 | -16.61 | -25.45 |
| decane | -19.39 | -20.54 | -29.37 |
| ethanol | -11.73 | -8.29 | -17.13 |

| | Graphite unhydr | Graphite hydr pre-equil | Graphite hyr no pre-equil |
|---|---|---|---|
| hd | -16.85 | -10.36 | -34.65 |
| vx | -30.33 | -29.55 | -53.84 |
| dmmp | -16.50 | -23.47 | -47.75 |
| demp | -23.54 | -23.18 | -47.47 |
| dimp | -25.88 | -27.92 | -52.21 |
| deep | -19.74 | -24.66 | -48.95 |
| tbp | -24.04 | -29.95 | -54.24 |
| cl2co | -9.07 | -13.38 | -37.67 |
| clcn | -7.49 | -9.50 | -33.78 |
| hcn | -6.44 | -10.12 | -34.41 |
| h2s | -3.46 | -4.85 | -29.14 |
| hexane | -17.93 | -8.58 | -32.87 |
| octane | -23.46 | -13.74 | -38.03 |
| decane | -24.32 | -16.24 | -40.53 |
| ethanol | -7.36 | -6.79 | -31.08 |

STATIONARY PHASE MATERIALS FOR MICRO GAS ANALYZER

This application claims the benefit of U.S. Provisional Application No. 60/657,557, filed Feb. 28, 2005.

The government may have some rights in the present application.

BACKGROUND

The present invention pertains to fluid detection and particularly to fluid detectors. More particularly, the invention pertains to materials of fluid detectors relative to fabrication of the detectors.

U.S. Provisional Application No. 60/657,557, filed Feb. 28, 2005, is hereby incorporated by reference.

Aspects of structures and processes related to fluid analyzers may be disclosed in U.S. Pat. No. 6,393,894 B1, issued May 28, 2002, to Ulrich Bonne et al., and entitled "Gas Sensor with Phased Heaters for Increased Sensitivity," which is incorporated herein by reference.

SUMMARY

This invention concerns selecting a stationary phase for a fluid analyzer using certain criteria to determine an appropriate material for use in, for instance, a micro fluid analyzer.

BRIEF DESCRIPTION OF THE DRAWING

FIG. 3 is a table of MGA performance with H2 or air carrier gas;

FIG. 4 shows a table of retention indices for polar compounds;

FIG. 10 shows amounts of correlation between experimental and calculated phase equilibrium or K-values;

FIGS. 64-91 may relate to adsorption energies of CWA's;

FIGS. 92-102 may relate to CWA on tetrafluoroethylene; and

FIGS. 103-110 may relate to some specific stationary phases.

FIGS. 111-127 may relate to DB1 and comparisons.

DESCRIPTION

Figure 1:
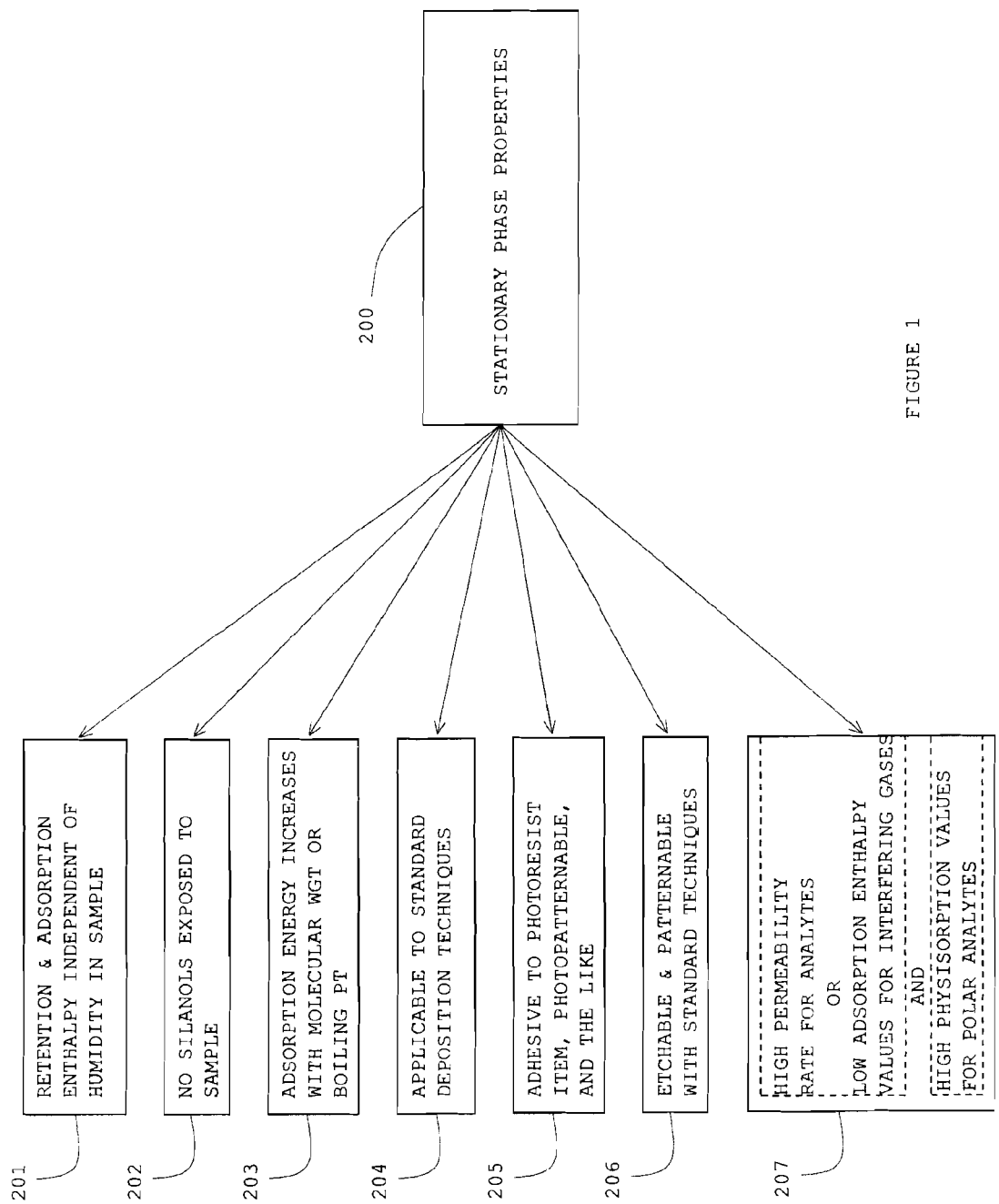
FIG. 1 is a diagram of stationary phase properties.

Microgas analyzer (MGA) stationary phases may utilize materials that provide certain properties within the MGA system. An example of an MGA is described at another place herein. As outlined in FIG. 1, desirable criteria or properties 200 of stationary phases may include: Item 201—Have a retention and adsorption enthalpy independent of humidity concentration in the sample gas; Item 202—Have no SiOH (silanols) exposed to the sample gas mixture, since silanols have retention/reaction enthalpies that are higher than normal adsorption enthalpies, and cause peak trailing; Item 203—Have adsorption energies that monotonically increase with molecular weight or boiling point; Item 204—Be applicable via std. deposition methods such as spin coating or spraying or vacuum deposition; Item 205—Offer reasonable adhesion to photoresist products or be photopatternable; Item 206—Can be etched and patterned by usual processes such as DRIE (deep reactive ion etching), plasma etching or liquid etching, and most importantly; and Item 207—Exhibit a high permeability rate for the analytes of interest or exhibit very low adsorption enthalpy values for interfering gases (e.g., alkanes), and high (physisorption and not reactive/chemical) values for polar analytes.

Some the primary properties or criteria of stationary phase material may include high absorptivity and low water interference. The water resistance may be derived through a use of high amounts of hydrophobic groups. The absorptivity may be derived by using enough polarizability on the surface without adding in active hydrogen bonding that will compromise water resistance. Items here may include non-polar sorbent for use for use in a micro GC concentrator/separator, new leaving groups and chemistries for silyl toughening agents for porous dielectrics, capping agents for porous adsorbing SOG's, and hydrophobic polymers as stationary phases for micro GC's bases on polynorbornene. Porous materials may be applied to an MGA or GC as spin-on formulations. Ultra low k dielectrics may be made by an introduction of pores. There may be surface functionalization after patterning and/or curing device structures. The structures may be made from one of the highly porous formulations, but porosity (high surface area) alone will not make a good stationary phase, and the specific functional groups found on the surface may tune the surface toward desired activity. The base of the polymers to be used may be extended. The polymers may be made porous to increase surface area, but the basic material may have the potential activity to resist water interference during adsorption.

The high surface area dielectric structures may be had within the MGA application. There may be porous materials of nanotube structures and are relatively stable to high temperatures that may be encountered during chip processing. Examples may include GX3P™ and NANOGLASS™ (Honeywell) which have open pore structures. Examples of high surface area carbon may include carbon nanotubes. There may be other porous examples, such as SiLK™ (Dow), where the surface pores are first opened by a plasma or wet etch in order to increase the surface area. Such structures may have a metal coating to provide an absorbent metal surface.

Functionization of high surface areas may be noted here in contrast to the related art. An example noted as a result of modeling may be the trifluoropropyl silyl group. The trifluoropropylmethysilyl group may be formulated into a spin-on treatment for NANOGLASS™ using dichloro- or diethoxy-trifluoropropylmethylsilane or similar monomers.

Other polymers may be found in modeling to be water insensitive. Even though these polymers may not be highly porous, pores may be introduced. Polynorbornene is an example, but others may include epoxy-novolac, pdms, polytetrafluoroethylene, and the like. Higher Tg materials may be made porous using similar technology as of GX3P™ and NANOGLASS™ which form pores using thermodecomposition of a pore-forming porogen constituent. Lower Tg materials may be made porous using a water soluble porogen strategy or lower temperature porogens made form HFC's.

Figure 2:
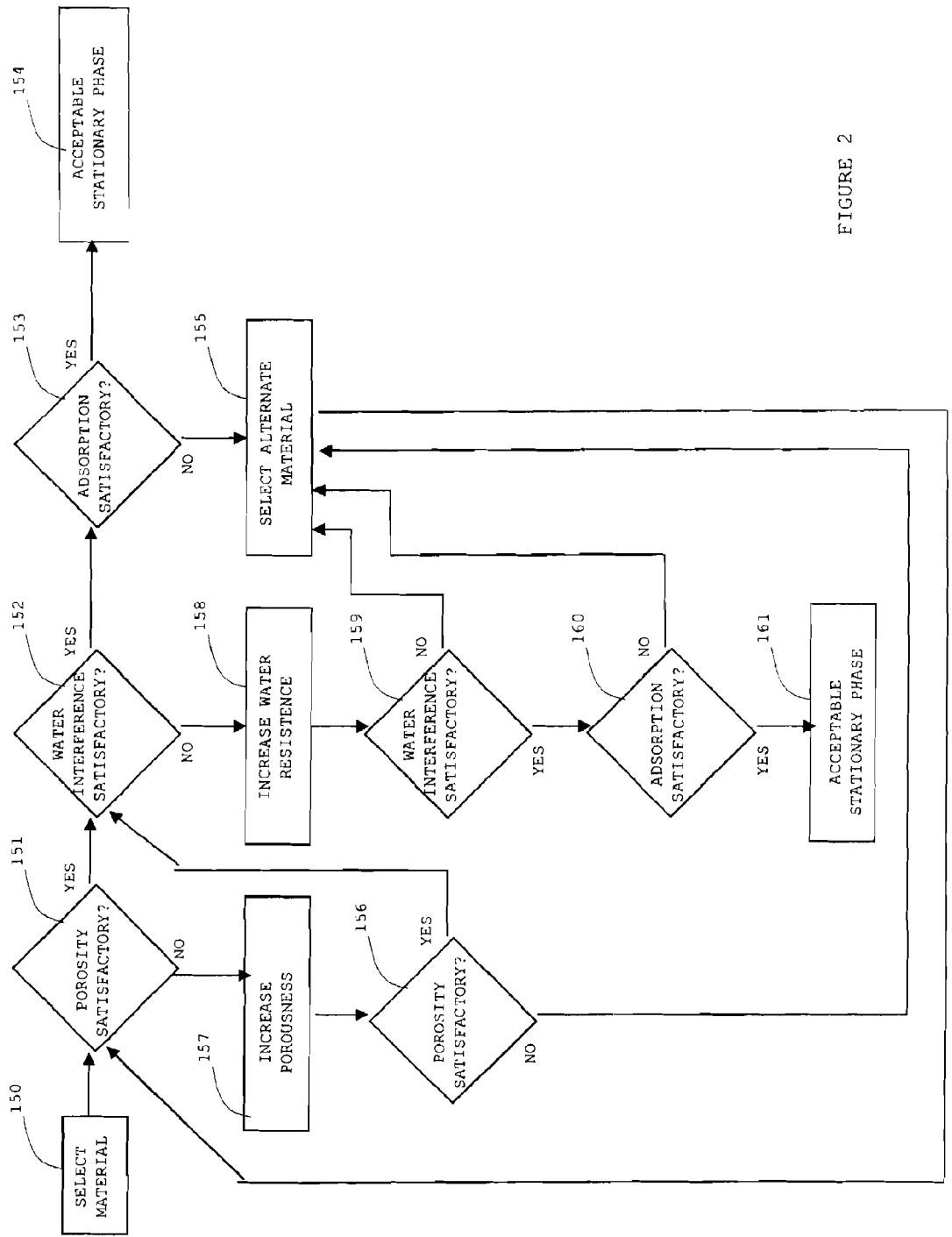
FIG. 2 is a flow diagram for selecting a stationary phase.

FIG. 2 is a diagram that illustrates linkage of the various material properties noted herein. One may begin at box 150 by selecting a candidate material for an MGA stationary phase. Then one may go to a question in diamond 151 which asks if the porosity of the material is satisfactory or acceptable for a MGA stationary phase. If the answer is no, then one may go to block 157 where, for example, porogen may be used to develop a porous material. Then from box 157, one may go to a diamond 156 where the question is whether the porosity of the material is satisfactory. If it is not then one may go to block 155 to select an alternate material which will be directed to a porosity question at diamond 151. If the question answer is yes to diamond 156, then one may go to a diamond 152 to answer a question about water interference. Also, if the question is yes to an inquiry of diamond 151, then one may go to the question in diamond 152 about whether the water interference of the material is satisfactory or acceptable. If yes, then one may go another diamond 153 that asks whether the absorption of the material is acceptable. If the answer is yes, then the material may be acceptable for use in the MGA at box 154. If the answer is no, then one may go to an alternate materials box 155 which may include hydrophobic polymers as material for stationary phases for micro GC's based on polynorbornens and other polymers which should perform with high adsorption and low water sensitivity, and select a material. However, from box 155 one may go with the newly selected material to the question at diamond 151 which asks whether the material is adequately porous. If the answer is yes, then the material may go to diamond 152 and follow the steps from that step on as indicated herein. If not, then one may go to box 157 where the porosity of the material may be developed possibly with porogen. From box 157 one may go to diamond 156 for the question as to whether the porosity is satisfactory. If not then one may go to block 155 to select an alternate material. If the answer is yes to diamond 156, then one may go to diamond 152 for the question as to whether water interference is acceptable or satisfactory. If the answer is yes, the one may go through the steps as noted herein for sequences from there. If the answer is no at diamond 152, then there may be water interference treatment such as capping treatments at box 158 for material such as a porous adsorbing SOG. From there one may go to a diamond 159 where the question of whether the water interference is acceptable. If the answer is no then one may go to box 155 and follow the steps after box 155 as noted herein. If the answer is yes, then one may go to the diamond 160 that asks the question of whether the adsorption is acceptable. If the answer is no, then one may go to the box 155 to select an alternate material and follow the steps as stated herein. If the answer is yes, then one may go to a box 161 where the material may acceptable for use in the MGA.

As a challenge one may evaluate stationary film material properties to enable at least comparative predictions and evaluations. A sorbent needed for the PHASED micro GC preconcentrator and/or separator should be highly hyrophobic but maintain some polarizability, contain very low hydrogen-bonding character, and be able to survive temperatures greater than 300 degrees C., with repeated cycling at greater than 200 degrees C. in air. It also should have low water sorbency.

This need may be fulfilled with several materials noted here. For example, materials that are highly nonpolar may be used. One may use an organic low k dielectric such as Silk or GX3P as the nonpolar sorbent. Nanotubes may be used as a nonpolar sorbent. To achieve the material need, one may metal coat the current silica/alumina sorbent, metal coat the organic low k dielectric or the nanotubes. Another material that may be used is a low k composite. These materials may provide some binding energy to an agent, and provide surface area for separation without thermal decomposition.

A GX3P film or layer may be used as a sorbent/separator with open pores. This layer may provide open pores, a high surface area, and a nonpolar surface as needed by the micro GC. The aromaticity may provide some binding to the agents being isolated. This layer would not appear to undergo as many processes as an IC, so it may be suited as the low modulus material.

A coating of carbon nanotubes (CNT's) (with standard CVD deposition) may be produced to provide a high surface area. The CNT's may provide a very high surface area with thermal stability (higher than the organic low k dielectric such as Silk or GX3P). The graphitic carbon may provide some activity to the absorbing species while maintaining a highly hydrophobic environment.

One may CVD or ALD coat a thin (i.e., in the angstrom range) coating of metal to the current porous inorganic material. The CVD or ALD thin coating of metal may be applied to the organic low k dielectric or the nanotubes which may include nodule coated supports to increase surface area of metal. Metal coating may provide activity to even non-polar entities, and provide less water sorbency than inorganic sorbents.

A composite structure of a low k inorganic and low k organic material may provide a halfway solution between the highly hydrophilic inorganic and the highly hydrophobic organic, but may also provide more sorbent activity than the organic solution alone, due to the increase in polarity.

Another approach may include use of a modified NANO-GLASS™. Instead of methyl groups, other organic silanes may be used for formulation. Stoichiometry may also be adjusted to increase organic content. The organic group on the silicon may modify the hydrogen bonding activity of the silicate and impart higher hydrophobicity to the surface. Modeling appears to indicate that phenylated nanoglass might offer better resistance to moisture effects; however, standard nanoglass appears to have a better CO2/EtOH energy separation. There may need to be a mixture of units or a patterning of a standard nanoglass and another patterning with a phenylated nanoglass.

There may be a need for a new leaving groups and chemistries for Silyl toughening agents for porous dielectrics. A known current silylacetoxy toughening agent (TA) appears to suffer from reactivity with copper leading to copper etching and residue formation. The ammonium acetate and acetic acid conditions used in the TA may lead to the copper etching and residue formation. Several new compounds have been identified in an attempt to get away from these conditions. In one family, a neutral leaving group may be used, and has been indicated in the literature to be moisture sensitive similar to the silylacetate and so should be readily hydrolyzable to react with the matrix SiOH. A second family is similar to HMDZ, but may use a dimethyl silyl group rather than a trimethyl silyl group. In this case, ammonia or an amide may be the leaving groups.

The first family of new TA agents may use a neutral leaving group. A neutral leaving group may avoid the etching and catalysis problems of the current acetoxy group. The present approach suggests that the amide leaving group may be a good alternative to the diacetoxy used in the related art. So dimethylsiyldiacetamide or dimethylsilyldiformamide may be the simplest compound whose leaving groups are neutral liquids. The TA reaction may involve: Si(NCOR)—>SiOH+ HNCOR and SiOH+SiOH—>SiOSi. Related art appears to show that the Si(NCOR) is easily hydrolyzable. The amide group may be known to be neutral or close to neutral so it should not be involved in the acid etching problem. The condensation reactions may be able to proceed in higher pH conditions (as opposed to the acid conditions obtained with the acetoxy group) with the neutral leaving group forming.

A second chemistry involving ammonia as a leaving group may be envisioned and may have similarity relative to HMDZ. But the new compounds should react with the nanoglass or silica to form a dimethyl bridging group which may be more stable than the trimethyl silyl capping group from HMDZ. These new compounds include (but are not limited to) hexamethylcyclotrisilazane, bis dimethylaminodimethylsilane and bis diethylaminodimethylsilane. One may note that the diamide compounds are a quite different chemistry than the HMDZ or diacetoxy chemistry. The amino compounds may have similar chemistries, but protect the dimethylsilylamines for the TA application in which the dimethyl group is found to have better stability than the trimethyl group found in HMDZ.

Capping agents may be had for porous adsorbing SOG. Capping agents may be used to promote hydrophobicity in thin film porous SOG's used for micro-chromatography applications. The thin films used in micro gas analyzers should be porous, thin and highly hydrophobic. SOG's commonly used as adsorber materials may suffer from unreacted SiOH functionality which causes high hydrophilicity. The use of these agents should increase hydrophobicity sufficiently enough to make the adsorption characteristics insensitive to water interference.

This approach may be related to another approach which describes the use of nanoglass and GX3P for chromatography applications, and also may be related to the approach which describes new leaving groups and chemistries for Silyl toughening agents for porous dielectrics, as well as related to existing toughening agent material noted herein. The similarity here is in the description of similar compounds used to react with SiOH group of silicates; however, the present approach may be used for the express purpose of increasing hydrophobicity for adsorptivity enhancement rather than primarily for toughening. A side benefit is a tougher film.

The present approach may use agents such as DMDAS, HMDZ, HMCTZ, DMSF, DMSDA, BDMADS, BDEADMS, dimethylsiyldiacetamide and dimethylsilyldiformamide to cap the SiOH with organic functionality that may also function as toughening agents. The list of possible capping agents may also include the di-alkyl silyl and di-aryl silyl derivatives of the above compounds. An especially good capping agent may be the trifluoropropylmethylsilyl group derived from trifluoropropylmethylsilylchloride which has recently been calculated to show low water sensitivity.

Hydrophobic polymers used as stationary phases for the micro GC's may be based on polynorborens and other polymers. Micro GCs stationary phases should operate with high affinity toward analytes while having little or no interference from atmospheric moisture. The present approach reveals a stationary phase made of hydrophobic polymers which should perform with high adsorption and low water sensitivity.

Molecular modeling studies appear to indicate that materials with high hydrophobicity should have resistance to water interference as a GC stationary phase, and thus should perform better than the silicates in the PHASED micro gas analyzer. It may be noted herein that highly carbon based materials such as carbon nanotubes and GX3P should make good GC supports with lower water interferents in comparison to silicate-types of materials.

The present approach may expand the list of hydrophobic materials that should be better stationary phases to include polynorbornene, PDMS, Teflon™ (polytetrafluoroethylene) or fluorinated polyolefins and novolac resins. The polynorbornene (polymerized thru the ring olefin without ring opening) surface appears interesting in that the adsorption energies may be higher than those found for other surfaces and may make the basis of a concentrator. The density of this polymer appears much lower than the other polymers, and may allow deeper penetration of the analyte species and improve adsorption. The high adsorption energies found when the analyte is placed within the mass suggest that this may be the case. The Teflon™ and PDMS surfaces appear to energetically resist the effects of water adsorption. Because polar groups also appear to help the adsorptivity of higher polar species, it may be concluded that a stationary phase which is highly hydrophobic by the lack of any hydrogen-bonding hydrogens, may have low water interference, and if the stationary phase also contains polar groups (with no hydrogen bonding hydrogens), then the adsorptivity polar analytes may be increased. The increase performance using higher polar polymers may be found in the polytetrafluoroethylene models in which the difluoromethyl groups have a large dipole moment, as well as the epoxy novolac models which contain large quantities of more polar ether linkages (in which models have assumed a high cure to tie up most of the free hydroxyl groups).

The development of films for the PHASED (phased heater array structure for enhanced detection) microgas analyzer, described herein, may be a key for meeting its high-speed (total analysis time <3 s), sensitivity (<1 ppb) and selectivity performance. The microanalyzer may be based on Si-micromachined gas chromatography channels with integrated flow, temperature and thermal conductivity detectors (TCD), with multi-stage pre-concentration (PC), injection without valves and no extra carrier gas other than the (air) sample gas. One may fabricate PHASED heater arrays of 40, 60 and 100 elements; with on-chip, integrated 20-50-stage PC; flow sensor; segmented separator column; and TCDs. One might fabricate and package an upgraded version to be compatible with standardized, modular 1.5×1.5" SP-76 substrates for NeSSI (new sampling/sensor initiative) system field tests at selected process industry sites, in addition to application of environmental, homeland security, biotechnology and medical diagnostics, while meeting palm-top size and affordability goals.

Measurement results may be obtained with excellent repeatability; TDC peak widths of about 8 ms (i.e., peak capacities of >100/sec) for a 20-stage pre-concentrator desorption, which may be synchronized with the sample/carrier gas flow velocity and then thermal-pulse-injected and made consistent with the $\leqq 3$ ms peak widths, a TCD response time of <1 ms, and sensitive micro-discharge devices as additional detectors.

Modeling efforts may focus on modeling, synthesis and selection of optimal absorber, separator and polymer film materials. An approach may be used to estimate dielectric constants, $\epsilon$, (i.e., polarity of analytes, and possibly stationary film), partition coefficients, K, retention factors, k', and retention times, $t_r$, for any analytes of which only boiling point, $T_b$, and elemental compositions. To estimate K, the addition of $\epsilon$ to boiling point, $T_b$, may reduce uncertainties by factors of 2-4×below estimations based on $T_b$ alone. This modeling effort appears to provide unexpected new insights into the relationship between retention and polarity of an analyte, such as the reduced partition coefficient and retention time when the polarity increases beyond a maximum of K has been reached.

With the derived K and k' values and their estimated film adsorption enthalpy, one may simulate and visualize the benefits of controlled temperature ramping of the separation column, either by extending the results of experimental isothermal GC (gas chromatography) separations or by generating such chromatograms from scratch.

To predict and meet specified MDLs (minimum detectable limits) and thus predict needed PC levels for given analytes, the first-principles model of the multi-stage pre-concentrator may be validated with experimental data obtained with a PHASED chip. PC gains for a one-level, thin-film-type capillary PC may then be computed as a function of its film thickness, the number of its stages, soaking and discharge temperatures, and the adsorption enthalpy of the analytes of interest, which may typically fall in the range between 6 and 15 kcal/mole or 20 and 70 kJ/mole. Next, one may evaluate stationary film material properties to enable at least comparative predictions and evaluations.

Regardless of size, gas chromatographs could be viewed as boiling point spectrometers in the sense that they may separate a mixture of gases by virtue of their different retention on the stationary phase of the separation column, which may be governed mainly by their adsorption energy, which in turn correlates with boiling points. Consequently, compounds of different boiling points may experience different interaction energies, be retained for different amounts of time, and thus be separated from each other and analyzed individually. The nature of the stationary phase may also influence the retention time, $t_R$, the related retention factor $k'=(t_R-t_o)/t_o$ and retention index for analyte i, $$I_i=100\{\log(t_{Ri}/t_{Rn})/\log(t_{Rn+z}/t_{Rn})+n\}, \text{where n=alkane of n C-atoms, z=1 or 2,}$$

because each film material also influences the adsorption energy or enthalpy, $\Delta H$. k' and $\Delta H$ are related by the remarkably simple relation $\log(k'_2/k'1)=\Delta H/R(1/T_2-1/T_2)$. Although this influence may be relatively modest and amount to no more than about 50%, it may be the basis for part of the separation strategy. In general, polar compounds such as alcohols, water and ketones may be believed to have higher adsorption energies and thus longer retention times than non-polar compounds such as alkanes, bimolecular gases and noble gases, as may be quantified. Stationary phases with large ranges of retention times and energies may be desirable for good separation. For good pre-concentration, one may also require high specific surface area to achieve high mass transfer rates and storage capacity.

There may be tradeoffs. If an unknown mixture of analytes comprises both polar and non-polar compounds, and if the problem at hand was to devise a strategy for the separate elution and analysis of all analytes, one might make sure that the separation power of the selected column was strong enough to separate all compounds. This may be accomplished with desk-top GCs with capillary columns of 20 to 60 m in length and analysis time of 5-30 minutes. If one add to this the need to complete the analysis in less than 4 to 10 seconds, within a tight energy budget, and to pre-concentrate the target analytes of interest 1000- to 10,000-fold, then one may need to seek and devise smarter and faster methods of analysis.

A solution may be need to cope with the presence in the sample gas of 1-3 mol % water vapor, which may occupy many adsorption sites and reduce the effectiveness of the adsorber and separator film materials. Selection of such materials may be facilitated if retention times and separation on them could be predicted.

There may be a preconcentration tradeoff, that is, heating vs. heating and cooling, in the quest for 1,000 to 10,000-fold pc, with a question of whether it is more energy-efficient to achieve that gain by only heating the needed number of elements in the pre-concentrator array or by cooling a fewer number of elements (to achieve a greater fractional adsorption in less time and with less pumping energy) in that array before heating them up to desorb. It seems that the "heating-only" approach, if feasible, may be by far the most efficient, because the (Peltier) cooling approach should involve a constant power drain during the soaking/adsorption time.

There may be a carrier gas tradeoff air, $H_2$ or He. From fluidic and mechanical complexity points of view, the use of air as a carrier gas may be the least complicated approach for a compact, stand-alone MGA. One should need no on-site $H_2$ or He storage or generation, and the flow rates required for optimal GC separation should be lower, thus reducing the pump size and power. However, the S/N and sensitivity of TDC, MDD and MS detectors may be higher with $H_2$ and particularly with He for MDD and MS. An additional aspect to consider is the notion of soft ionization in which either of the following may be noted.

There may be some intermediate ion, typically $H_3O^+$, that transfers its $H^+$ ion to the analytes of interest, which may be done advantageously with an air carrier, because the $O_2$, $N_2$ and Ar affinity for $H^+$ ions is much lower than that of most analytes; or the analytes in the sample gas are ionized by subjecting them to a strong electric field. Although one approach may be to welcome ionization with fragmentation of the analyte to aid with its identification. Presently, one may consider soft ionization for use in a compact, high-speed micro analyzer. A table of FIG. 3 summarizes the pros and cons of the approaches.

In some examples, the change in retention indices for n-octanol-1 on PDMS, a non-polar phase, and PEG, a polar phase, may be from I=1038 to 1545 or an increase of 50%, despite already being 30% higher than the reference n-octane on PDMS. A table of FIG. 4 shows a few other related index values.

The operation and performance of PHASED MGA separation may be noted. To describe and model PHASED separation and elution of any analyte or analyte mixtures, one may start with physics and thermodynamics, with estimating separation based on physical properties of analytes and stationary phases. One may discuss the contributions made by the structural features of PHASED on analyzer resolution and then address how thermodynamic and physical properties of analytes may help to predict retention time.

Figure 5:
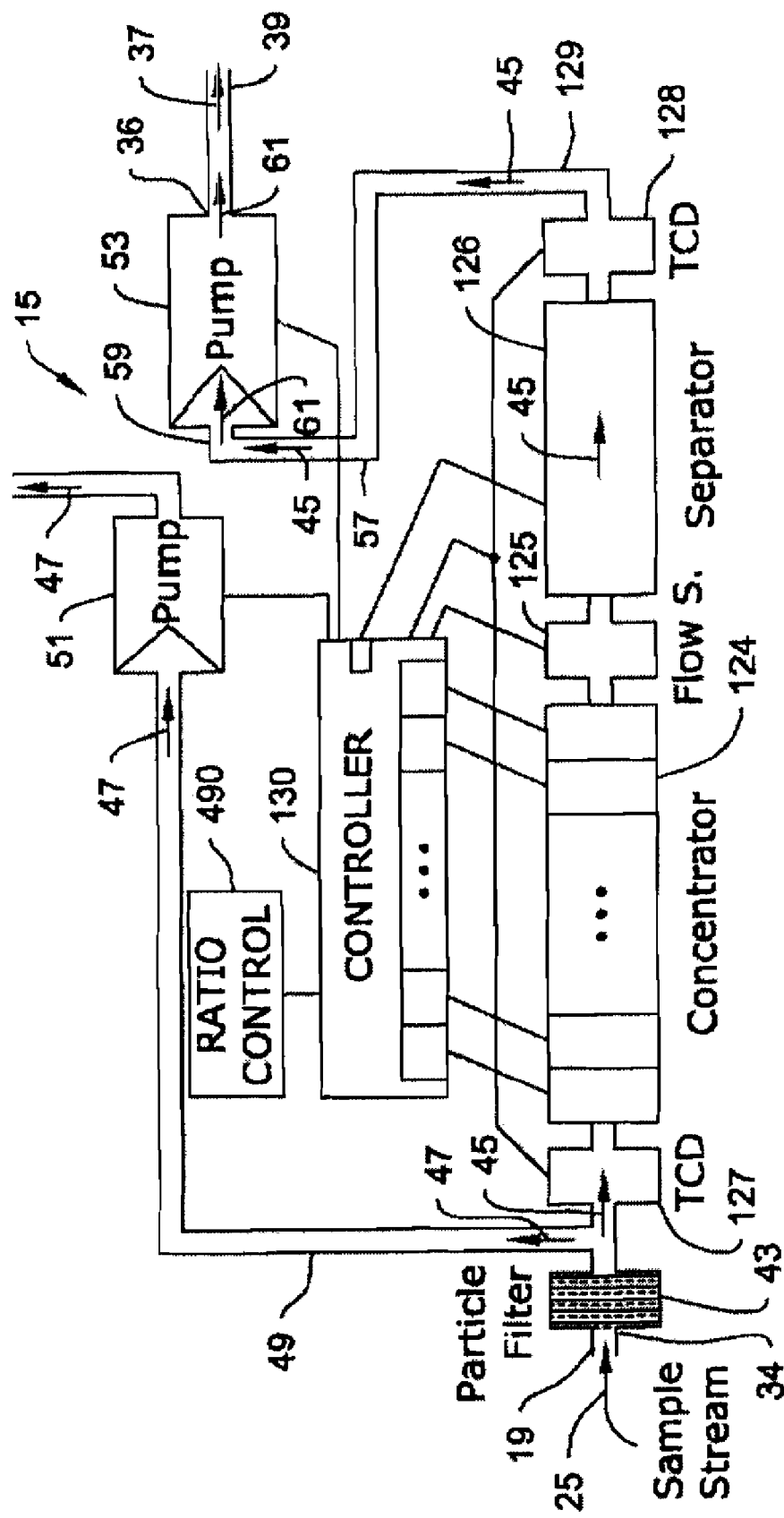
FIG. 5 is a layout of an illustrative phased heater mechanism.

The PHASED analyzer structure may consist of an array of pre-concentrator and separator elements forming a continuous column, as shown in FIG. 5. Such column may be of a square cross section, see FIG. 6, wherein the array of thin-film heaters and corresponding thin-film stationary phase may occupy one of the four sidewalls. This may be a significant departure from other style GC structures, especially for separation columns, which might consist of circular cross-section capillaries whose inside diameter may be uniformly coated with a stationary phase or film of 0.1 to 10 μm in thickness.

One may note the resolution in view of coating one side of the square cross section column, and the uneven heating or complete lack thereof on the uncoated walls of the PHASED columns. Theoretical solutions in terms of reducing the risk of low performance may be noted in the following.

One item is having the coating on one side. In expanding the Golay equations for GC column theoretical plate height and resolution to non-circular, rectangular and partially coated columns, there may be comparisons between a circular column with uniform inner coating of the stationary phase, a square column with all walls coated, and square column with one wall coated. The theoretical plate heights of these designs may relate as 1:1.5:2, respectively. A reason that the uncoated walls do not cause a much greater increase in plate height may be the contribution of rapid radial diffusion, which largely eliminates the effect of laminar stratification. Without gas-phase diffusion, the retention time, $t_r=t_o$, near the uncoated walls may correspond to that of the unretained time, $t_o$, and thus result in no separation at all and very broad elution peaks composed of a range of retention times. The significance about the 2× lower PHASED-one-coated-wall resolution, relative to a capillary of equivalent size, may be that it is not larger than that, plus it could be supported by experimental evidence. The above degradation factor of 2× may be smaller.

Uneven heating is not necessarily a contention. It may be noted that: 1) The elution times may be shortened by about 2× for each 15 to 20° C. rise in column temperature; and 2) The elution or capacity factor expressed in terms of the elution time as $k'=(t_r-t_o)/t_o$ may be proportional to stationary film thickness (e.g., reducing the thickness from 600 nm to 10 or 0.5 nm may reduce the k' by 60-1200×). During temperature ramping, the unheated walls (facing the heated membrane walls) may at times be colder by 20 to 180° C. relative to the heated film and thus may increase k' by about 2-1500× at least part of the time. This may partially balance the effect on k' of the much thinner films of the unheated walls (which could just consist of a $\leqq$1-nm "deactivation" film to "cap" the SiOH remaining from siloxane or $SiO_2$-based column and film materials). Because the cold wall film thickness (and mass-loading capacity) may be so small, its contribution to the overall separation "work" may appear small but be viewed as supportive of achieving a k'(cold)$\geqq$0, which in turn could support achieving a reduction in the theoretical plate height penalty factor of 2×.

Quantitative values of both the "one wall" and "uneven heating" effects may be determined experimentally. One could calculate GC retention times for industrial, environmental, medical and home security analytes. GC-based analyzers may be fabricated with an approach to control stationary film temperature, a specified film thickness and a type of material to achieve the desired separation of small, medium or large analyte molecules. To tailor film and column geometries to achieve k'-values and thus a predictable separation of a set of analytes, of which only the atomic composition and boiling points are known, may be feasible for chromatographers. A simple relation between an analyte property and elution time may be an analyte boiling point temperature. One might determine the partition (or equilibrium) coefficient, K, and from there the values of k' and $t_r$, using the known relations for $k'=K/\beta$ and $t_r=t_o(k'+1)$ by one or more of the following approaches.

One approach may be experimental via a data bank of analyte-and-film k' values as generated. These k' values (despite uncertainty in film thickness) may be converted into $K=k'\cdot\beta$ for their particular value of $\beta$=(gas volume)/(stationary film volume), from which the k' values for other column geometries may be derived.

Another may be calculation of K via molecular modeling of adsorption enthalpy, $\Delta H$ and its relation to K via ln (K)=$\Delta H/RT-\Delta S/R$, where, according to Trouton's rule, the vaporization entropy is approximately $\Delta S=\Delta H/T_b$ at the boiling point, $T_b$. Information about this modeling work may be presented in the bar graph of FIGS. 7 and 8, in which the former presents a comparison between vaporization enthalpies from the literature, experimental isothermal GC retention times at various temperatures, and molecular modeling. As shown in the model validation results of FIG. 7, the modeling uncertainties seem no larger than those of the experimental data.

There may be a calculation of K via a correlation with the analyte boiling point, $T_b$, and its (liquid) relative dielectric constant, $\epsilon$, which may express its polarity, that is $K=K(T_b, \epsilon)$, under the heuristic assumption that this might result in more accurate K-values relative to $K=K(T_b)$.

There may be a calculation of K via linear salvation energy relationships (LSERs). In the development of LSERs, dielectric constants may have been used, but have been replaced with the parameter set, $\pi$, $\alpha$, $\beta$, R and log L16, as the better set for modeling. Molar refraction and thus $\epsilon$ may be built into the polarizability parameter R of the LSERs.

One may note results obtained for the molecular modeling and the $K=K(T_b, \epsilon)$, approaches. As to molecular modeling, the calculated energies may be generated using a standard Newtonian force field (CVFF/using Discover from Accelrys, Inc.) The force fields may include parameterization of important bond and non-bond forces to calculate the total energy of the system.

$$\Delta E = \sum D_b [1 - e^{-\alpha(b-bo)}] + \sum H_\theta (\theta - \theta_0)^2 +$$
$$\sum H_\phi (1 + s\cos(n\phi) + \sum H_\chi \chi^2 + \sum\sum F_{bb'}(b - b_o)(b' - b'_o) +$$
$$\sum\sum F_{\theta\theta'}(\theta - \theta_o)(\theta' - \theta'_o) + \sum\sum F_{b\theta'}(b - b_o)(\theta - \theta_o) +$$
$$\sum F_{\phi\theta\theta'} \cos\phi (\theta - \theta_o)(\theta' - \theta'_o) + \sum\sum F_{\chi\chi'} \chi\chi' +$$
$$\sum \varepsilon[(r^*/r)^{12} - 2(r^*/r)^6] + \sum q_i q_j / \varepsilon r_{ij}$$

where the first 4 terms represent bond stretch, angle, torsion and out of plane movement respectively, the $5^{th}$-$9^{th}$ terms represent coupled deformations and the last two terms represent non-bond interactions for a Van der Waals and a Coulombic contribution. Newtonian molecular modeling of force fields generally use all of these contributions.

Figure 7:
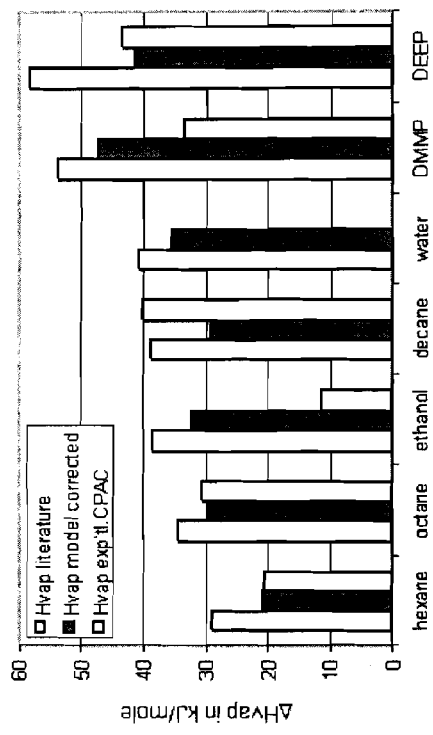
FIG. 7 is a graph for validation of molecular modeling of adsorption energies on analytes.

FIG. 7 shows the calculated enthalpies of vaporization as may be estimated from the modeled total internal energy change going from the condensed to a molecular state where $\Delta H = \Delta E + nRT$. The model vaporization energies appear to track well with literature values, thus providing a form of validation of the calculations. However, studies may be derived from application of the molecular models in screening stationary phases for adsorptivity (FIG. 8) as well as determining the resistance of the stationary phases to the common water interferent.

Figure 8:
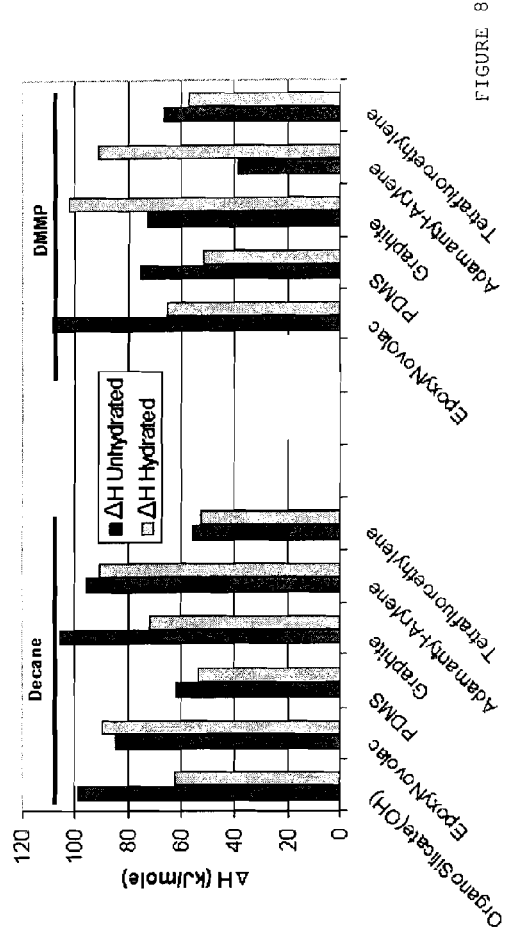
FIG. 8 is a graph showing a comparison of interaction enthalpies.

FIG. 8 shows interaction/adsorption (internal) energies for a number of compounds of interest and their dependence on the presence of water vapor in the analyte sample mixture (leading to hydrated vs. non-hydrated states of the film surface). Among the stationary phase film materials noted, the materials appear to exhibit decreasing $\Delta H$-dependence on the presence of water, particularly for a polar analyte such as DMMP, while retaining relatively large adsorption energies. The materials may include organo-silicates, epoxy-novolac, PDMS, graphite/carbon nanotubes, polyadamantyl-arylene, and polytetrafluoroethylene. FIG. 8 shows an adsorption distinction between a nonpolar (decane) and polar (DMMP) analyte, as well as a higher hydration effect of the polar DMMP. The highly hydrophobic surfaces like graphite and the arylene-acetylide, have higher DMMP adsorption when hydrated thus suggesting the significance of a polar nature of the stationary phase surface when adsorbing polar analytes. A notable surface is tetrafluoroethylene which may contain the high individual bond dipole moment (C—F), and have very low water interference. These items suggest that it may be desirable to have some form of polar entity involved in the stationary phase, but with low hydrogen bonding capability in order to reduce the interference from moisture. These observations may agree with a QSAR analysis run against the modeled adsorption energies for various sample analytes adsorbing to a surface of its own molecules. Molecular descriptors may be used as variables including dipole moment, molar refractivity, atomic polarizabilities, solubility, molecular weight, density and hydrogen bonding capability. In this case, the polarity as suggested by the dipole moment may be an important variable ($r^2=0.998$).

$\Delta E_{ads}$(hydrated)=28.4871+1.19332·InertialMoment+ 4.10169·DipoleMagitude−5.10113*DipoleZcomponent−0.108962*MolRef Polarity issues may be important to the design of the stationary phase, especially when considering that concentration/separation should occur in a relatively short period of time, with very small features on a chip-scale device. However, now that modeling may more quantitatively illustrate the adsorptivity changes due to material design, the question of the best matching of surface functionalization to the base stationary phase should be noted, as a base polymer is not necessarily used which could provide a deleterious influence to the activity in the device's thin film format. Additionally, one may be limited to the types of base materials that may be available which provide adequate surface area. Since current models may assume that adsorption is a key performance variable, modeling improvements for dynamic issues such as surface diffusion may have to be relative to material performance needs.

Figure 11:
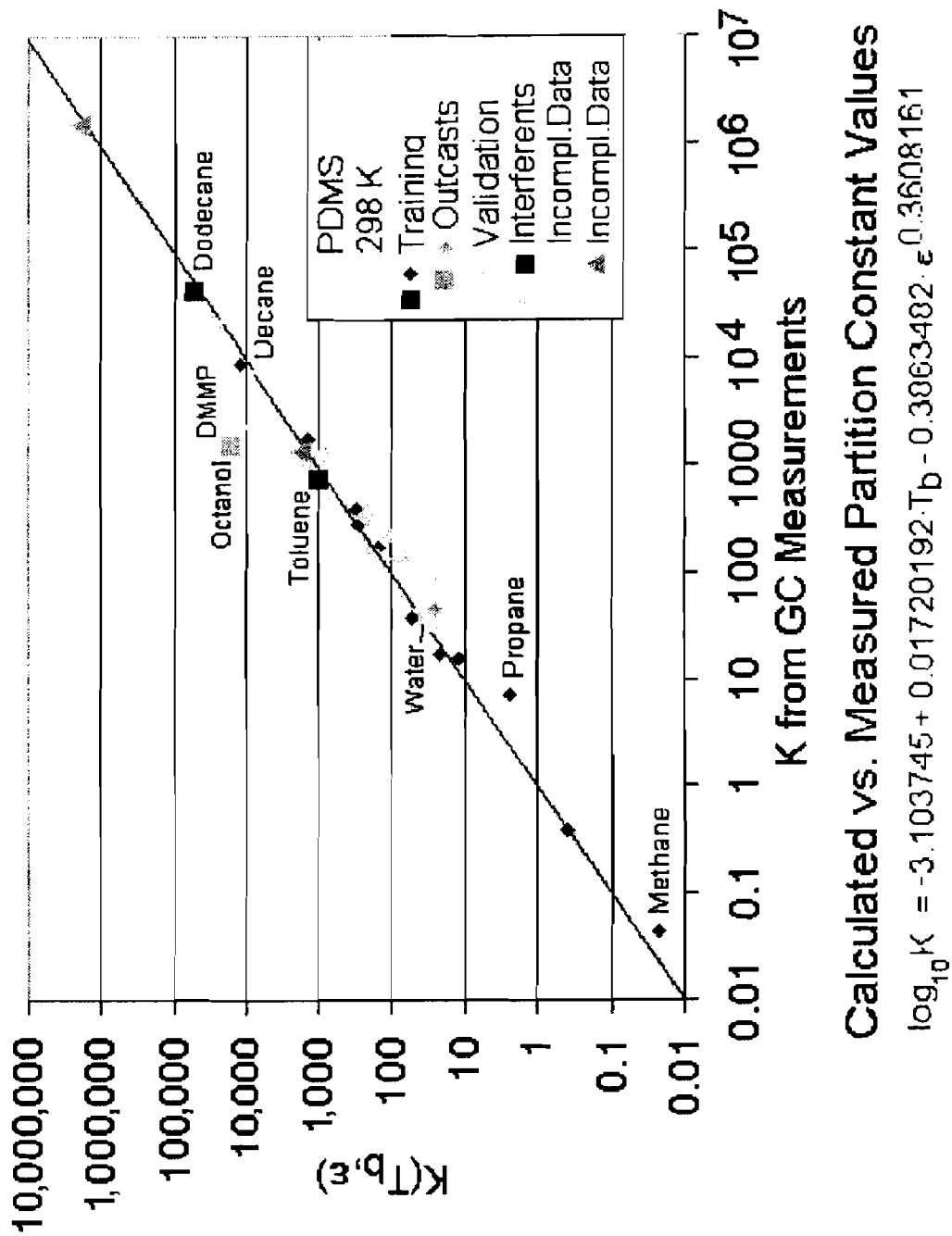
FIG. 11 is a graph of calculated and measured partition constant values.

The $K=K(T_b, \epsilon)$ approach may be noted. To derive or "train" the $K(T_b, \epsilon)$ correlation, one may use a set of k' values (normalized to 298 K) provided for GC measurements with PDMS-based columns. A table 3 of FIG. 10 lists the analytes used for training (top group A) and the analytes used for "testing" or "validation" (group B), for which k' and K data may be available. FIG. 11 shows the plot of calculated vs. experimental K-values for the training set (dark diamonds and squares of group A) and the calculated vs. experimental K-values for the "validation" set (diamonds, squares and inverted triangles of group B); the K-values of some compounds without $\epsilon$-data may be estimated from their boiling points and calculated dielectric constants. For the largely pure PDMS stationary phase (RTX-1 and DB-5), the derived correlations $K=K(T_b,\epsilon)$ appear improved in terms of the reduced uncertainties (1-sigma) for fits based on the following items.

1. One linear $T_b$-term and no $\epsilon$-term: ±15.8% for the 11 compounds of group "A"
2. One $T_b^m \cdot \epsilon^n$-term with non-linear exponents: ±7.4% for the 11 compounds of group "A"
3. Individual $T_b^m$ and $\epsilon^n$-terms, with m=1: ±6.6% for the 16 compounds of groups "A" and "B" (after deleting 2 outliers) and
4. Single linear $T_b$-plus two non-linear $\epsilon$- and $T_b \cdot \epsilon$-terms, without outlier deletions: ±3.4% for 18 compounds of groups "A" and "B"

This last type of correlation, derived for F-100, PDMS/RTX-1 and a fluorinated version of it (RTX-200), is shown in the following.

$$\log_{10} K = -3.624056 + 0.01636964 \cdot T_b - 1.216989 \cdot \varepsilon^{0.7910698} + \quad (1)$$
$$3.198916 / T_b^{0.1381811} \cdot \varepsilon^{0.7340864} \pm 3.38\% \; 18D0,$$
$$TLS = 31.35, \; TME = 8.88\% \; 7\text{-}JAN\text{-}05 \; RTX - 1$$

$$\log_{10} K = -3.982456 + 0.01640873 \cdot T_b - 1.513345 \cdot \varepsilon^{1.117895} + \quad (2)$$
$$2.550284 / T_b^{0.06985425} \cdot \varepsilon^{1.084002} \pm 7.34\% \; 18D0,$$
$$TLS = 161, \; TME = 17.1\% \; 3\text{-}JAN\text{-}05 \; RTX - 200$$

-continued $$\log_{10} K = -3.954085 + 0.01700603 \cdot T_b - \\ 1.694788 \cdot \varepsilon^{1.11793} + 2.818873/T_b^{0.0698} \cdot \varepsilon^{1.084}; \pm 2.77\% \ 14D1, \\ TLS = 3.74, TME = 5.17\% \ 9\text{-}Jan\text{-}05 \ F-100$$ (3)

The correlation uncertainty may be improved by about 2-4× as the dielectric constant is added to boiling point temperature. For gases analyzed and separated on PDMS, the improvement may be from a std. deviation of ±15.8 to 3.4%, despite increasing the number of analytes from 11 to 18. For the 13 gases analyzed and separated on F-100, the improvement may be from a std. deviation of +4.47 to +2.77%.

Figures 12, 13:
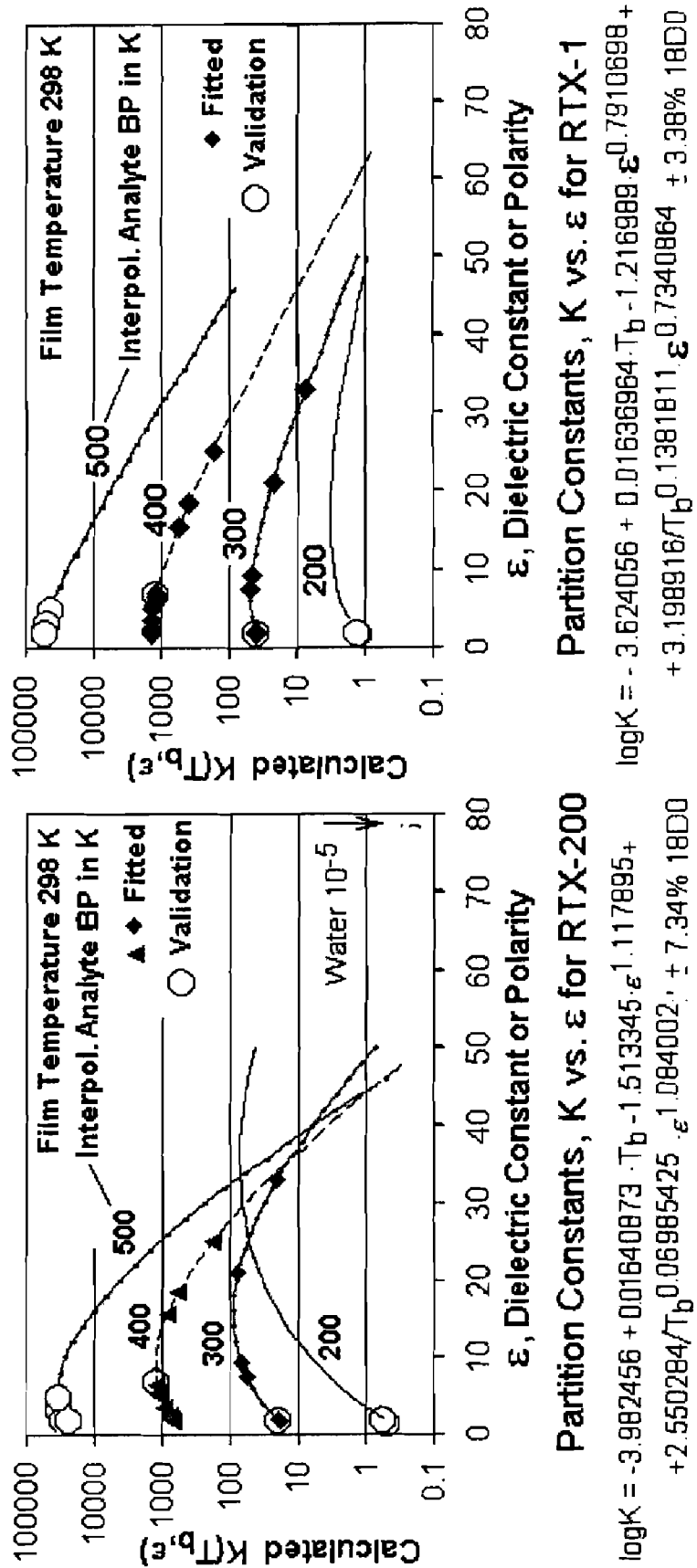
FIGS. 12-16 are graphs of K versus dielectric constant or polarity.

FIGS. 12 through 16 show graphic representations of the correlations. In FIGS. 12 and 13, the points may be placed right on the curves corresponding to round boiling point temperatures of 200, 300, . . . , 500° K. by choosing their boiling points to be $T_b^* = \text{INT}((T_b+50)/100)*100$ and their true dielectric constant, $\varepsilon$, for calculating $K(T_b^*,\varepsilon)$, which is also how the curves are drawn. However, for FIGS. 14, 15 and 16, the plotted K may retain the variability "flavor" of their measured value, $K_m$, by plotting $K=K_m \cdot K(T_b^*,\varepsilon)/K(T_b,\varepsilon)$, which moves each K-value by just an individual factor toward the constant-$T_b$-curves of even boiling temperatures (200, 300, 400°, . . . in K) in such a way that their relative distance from the actual correlation equation is maintained, while shifting its ordinate value toward one of the shown constant $T_b$-curves, without changing its $\varepsilon$-value. That K-scale distance from one of the even temperature curves may be zero if the measured value $K_m=K(T_b,\varepsilon)$. The reason for going through this exercise may be to better visualize the 3-D surface of $K$-$T_b$-$\varepsilon$ and understand the implied relation to and role of $\varepsilon$, without resorting to 3-D plots.

One could then compare the constant boiling temperature curves in the K vs. $\varepsilon$ plots for the three stationary phases PDMS, RTX-200 and F-100, and notice that these curves may show maximum K values for certain analyte polarities, i.e., $\varepsilon$-values, a stronger $\varepsilon$-dependence for more "polar" stationary phases, i.e., the K-values decrease more rapidly after its maximum and at lower values of $\varepsilon$, and the analytes featuring very large polarities may have K-values that are lower than one would estimate solely on the basis of their boiling points, and thus would exhibit relatively low k' values and be retained for less time.

If the these trends and relations are verified with more analytes, especially with highly polar ones, then one might envision having stationary phases that separate polar compounds but do not retain water significantly. Examples of highly polar analytes and their $\varepsilon$-values may include formamide—84, water—79, methanol—33 and ethanol—25.

Other challenges that still loom may include accurate thickness determination of the stationary phase films inside the capillary columns, which relate the measured retention or capacity factor, k', to the partition coefficient, K, via the volumetric ratio, $\beta$=(Gas Phase)/(Stationary Phase), and $K=k' \cdot \beta$. To resolve this, one might explore the feasibility of a gravimetric approach, based on the micro-weight gain of a capillary before and after depositing the stationary phase, and then use its density to arrive at its volume and its (assumed uniform) film thickness; and accurate determination of the zero-retention time, $t_o$, which is often difficult with traditional FID detectors but not with TCD or MDD detectors included in PHASED, which also respond to non-organic gases.

An estimation of analyte polarity or dielectric constant, $\varepsilon$, may be noted. To support and complement the estimation of the partition coefficient (between analytes and stationary phases), K, for which knowledge of $\varepsilon$-value may be shown to be advantageous, one may present a thought process for estimating the analyte permittivity or relative dielectric constant, $\varepsilon$, in the liquid state of the analyte, which may be the state associated with its solvation/adsorption on a stationary phase film of a gas chromatography column. This still may leave open the assumed influence of $\varepsilon$ of the stationary phase on K, to be analyzed.

The relation between molecular polarity, molar refractivity and dielectric constant may deal with the Lorentz-Lorenz equation of classical optics, which relates mean polarizability, $\alpha$, molar refractivity, A, and dielectric constant, $\varepsilon$, where $\alpha \cdot 4 \cdot \pi \cdot N/3 \equiv A = (\varepsilon-1)/(\varepsilon+2)$, with $N=6.02 \cdot 10^{-23}$ Avogadro's number of molecules per mole. Maxwell's relation of $\varepsilon=n^2$ may imply that $\varepsilon$ is frequency dependent, as is the molar refractivity, A, which is the total polarizability of a mole of a substance or analyte, and thus may be quite independent of its gas pressure or its gas or liquid state. A part in predicting K is that A is a material constant which may be a function of and can be predicted from its atomic constituents, $A_i$, as might be shown for $O_2$, HCl, $H_2O$, $CS_2$ and acetone. To get $\varepsilon$ explicitly, one may rewrite the above equation as $\varepsilon=(1+2 \cdot A)/(1-A)$, although this implies values of A limited to $A \leq 1$ because values of A>1 may lead to negative values of $\varepsilon$.

It may be that adsorption/solution of analytes on polymeric film materials might not be so much influenced by high (optical-frequencies) dielectric constant or polarizability but rather more by DC or low-frequency values of $\varepsilon$, and one may refit new, low-frequency A-values for a set of known $\varepsilon$-values, from which one may derive the $A_i$ needed for our analytes of interest via regression analysis with the contribution of the involved atomic species.

Figure 17:
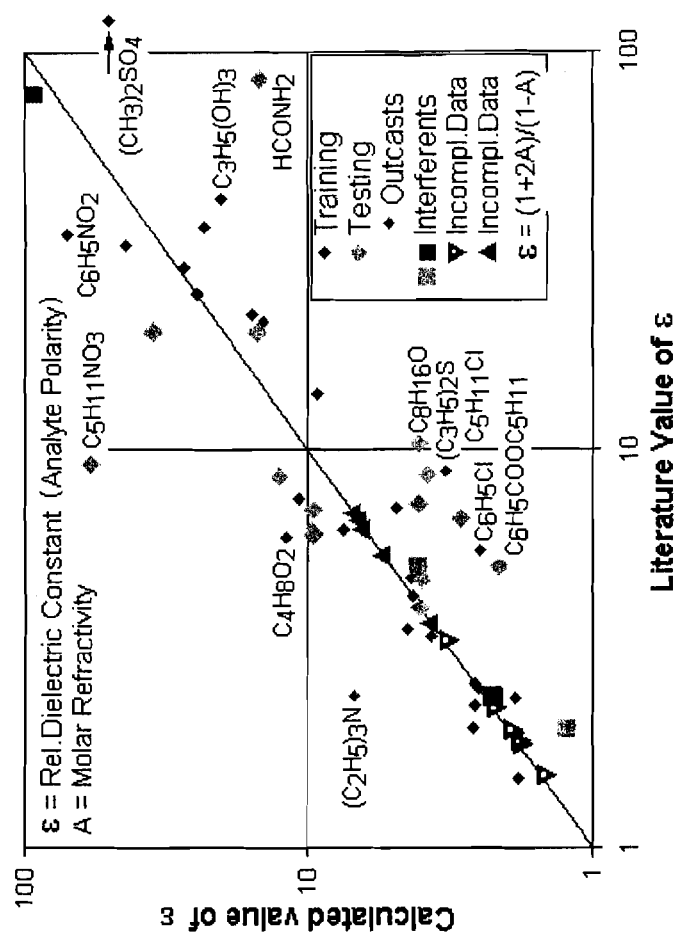
FIG. 17 shows a graph of calculated versus literature dielectric constants.

Accordingly, one may select i=1 to 7 to represent H, C, O, Cl, S, N and P, respectively, and heuristically expanded to i=11 to allow for extra representation of the contributions of the groupings HC, OH, HCl and HP and optimizing the regression by allowing non-linear exponents for the first seven of these atomic contributions. This appears to narrow the 1-sigma regression uncertainty from about ±13 to 5.4%. FIG. 17 shows a graphical representation of the achieved relation between the literature and values of $\varepsilon$ calculated this way. The dark-colored (small diamond or square-shaped) points represent the set of data used to derive the correlation, whereas the light-green-colored (large square-shaped) points represent $\varepsilon$-data used to validate that correlation. The triangles represent calculated values or estimates only, since no measured $\varepsilon$-values appeared readily available for those compounds.

Parametric analysis may be based on experimental GC data. An analyte mixture composed of 8 compounds (dodecane, octanol, toluene, hexane, DMMP, DEMP, DEEP and DCH) may be analyzed and separated and be shown in the composite of FIG. 18. These may be isothermal runs at 100, 110 and 125° C., obtained with a capillary of 1.5 m in length, 100 μm ID; a very thin, medium-polar stationary phase (F-100), and $H_2$ carrier gas at an average velocity.

One may leveraged the information embedded in experimental chromatograms for parametric analyses of the same capillary-based separation and of the channel geometry available in the PHASED chips, as represented by its own geometry. From the retention times, $t_r$, of the 8-component run at 110° C. with 8.96 mL/min $H_2$ gas carrier flow rate (at assumed ambient conditions), one may determine $t_o$ and k', to simulate the benefits of capillary temperature ramping, which might not be available experimentally in a high-speed chromatographic set up, and then translate these items into a predicted performance of PHASED.

There may be a determination of $t_o$ and k'. Before noting such determinations, one may note some aspects of the analysis of the GC data.

Figures 19, 20:
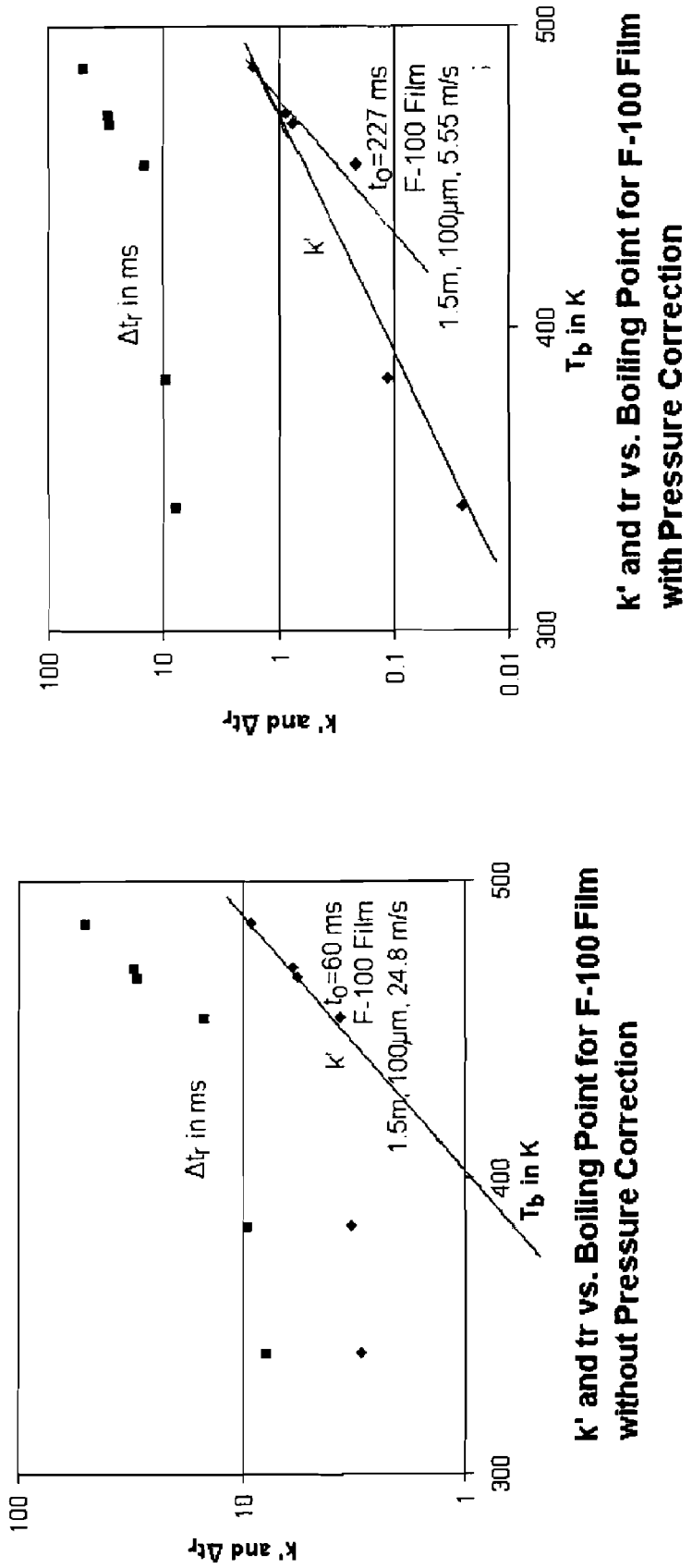
FIGS. 19 and 20 show plots of k' and tr versus boiling point for a material.

By potting ln(k') vs. boiling point, $T_b$, ($T_b$ for DEMP and DCH not available here) and trying to get straight lines by varying $t_o$ (zero retention time), one may derive a best fit to the data with $t_o$=227 ms, the plots for which are shown in FIG. 19 (the odd point is for DMMP which often sticks out), as well as for the flow and GC conditions, k'=1.696 for dodecane, 26.26 psid at column inlet, and 5.55 m/s for average gas velocity of $H_2$, which may result in 2 mL/min $H_2$ gas flow at ambient conditions and appears much smaller than an experimental value of 8.96 mL/min.

By computing $t_o$ from the 8.96 mL/min, correcting for the temperature effect on velocity and $t_o$, one may get $t_o$=60.4 ms and FIG. 20 (here the odd points are for hexane and toluene), as well as the flow and GC conditions, k'=9.21 for dodecane, 117.6 psid (without correcting viscosity for the temperature rise, which may cause an additional increase of about 20%), and 24.85 m/s for the average gas velocity of $H_2$.

Figures 21, 21A:
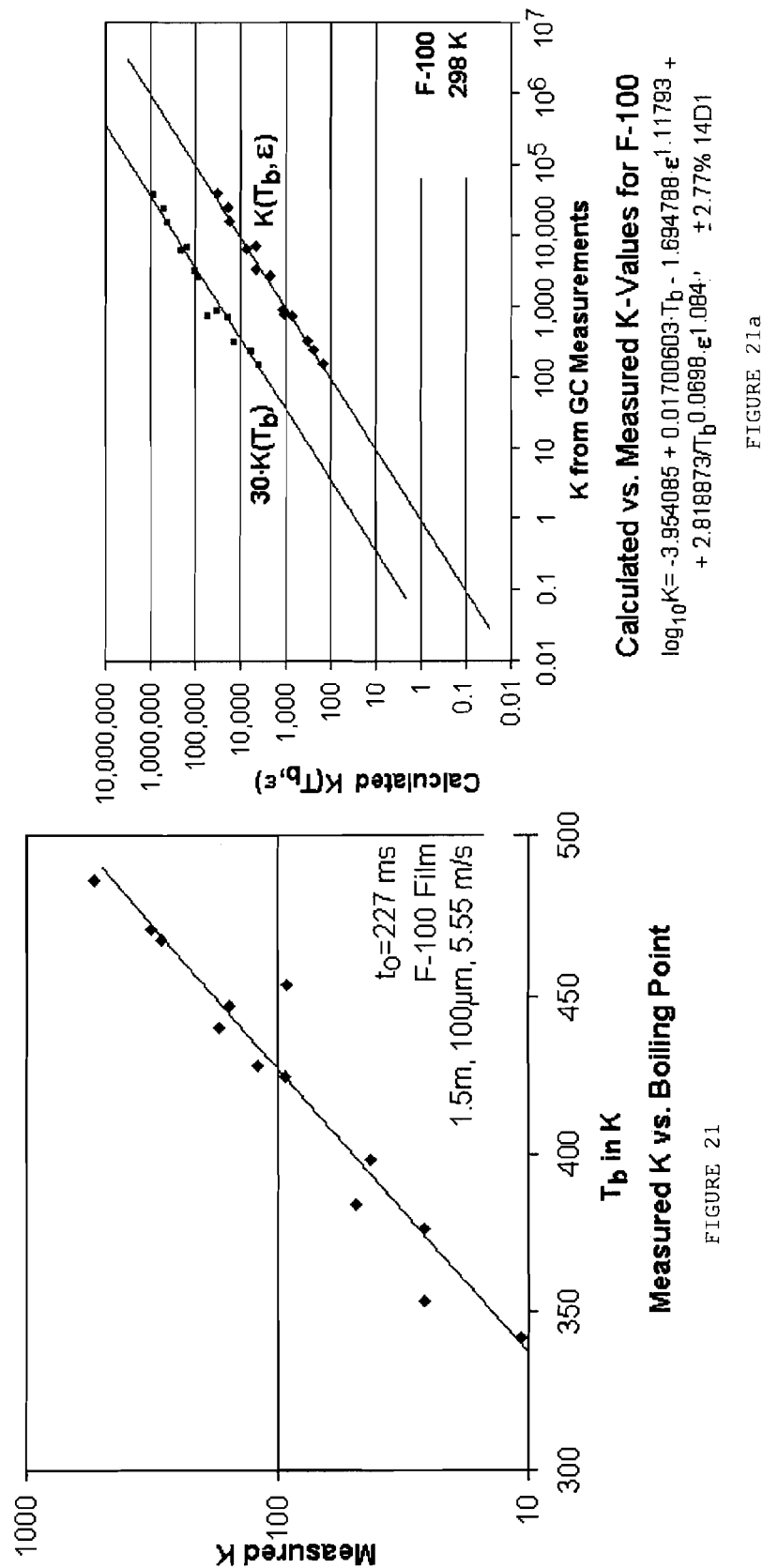
FIG. 21 shows a graph of measured K versus boiling point of a material.
FIG. 21a is a plot of calculated versus measured K-values for a material.

For these scenarios, the slope of the k'-at-110° C.-line connecting the upper 4 points on the k' vs. $T_b$ plots may be equal to the slope of the line averaging over the much larger set of analytes, which may analyzed with the same setup, for which the results may be plotted in FIG. 21. FIG. 21a shows calculated vs. measured k-values for f-100.

To reconcile these results one may check for pressure effects, since significant pressure drops could be involved with the capillary flow. As the pressure drops from the inlet to the outlet, the laminar flow may accelerate but affect analyte retention times in the same way, i.e., linear averaging over the pressure drop range for a case above may correspond to an average carrier gas pressure of about 59 psig and an average flow velocity reduced from 24.85 m/s to that of a gas compressed by a time-averaged factor of (59+14.5)/14.5=5.06×, which may lead to an unretained velocity of 500 cm/s and result in $t_o$=150/500=0.3 s, which appears closer $t_o$=227 ms than 60 ms. In summary, to =227 ms may be selected for a simulation of the capillary separation process, an average carrier gas pressure of 59 psig and the associated 74/14.5, about 5× drop in $H_2$ gas diffusivity relative to its value at ambient pressure.

By using the above as reference data, one may estimate the PHASED separation performance, knowing that the present PHASED chips may use a "column" or channel of maximally 25 cm in length, with a square cross section and a stationary phase-plus-heater combination (for controlled temperature ramping) on just one of its four walls. This may result in a 2× performance degradation, relative to a circular and uniformly coated capillary, as expressed by the broadening of the peak half width, w, associated with a loss in resolution*, R*. That degradation may be balanced in part by having the PHASED channel operate closer to its optimal velocity, corresponding to the minimum in Golay's equation for theoretical plate height vs. carrier gas velocity, resulting in an additional degradation factor between 1 and 1.38, depending on the k'-value, as noted here. Resolution may be defined as $R^*=t_r/w=(L/(H\cdot 5.54))^{0.5}$ (i.e., high resolution is desirable, just as it is desirable to achieve a high $\lambda/\Delta\lambda$ in optical spectroscopy), with L=column length and H=height of a theoretical plate.

By itself, a 6× drop in column length may result in a drop of $6^{0.5}$=2.45× in resolution* or corresponding increase in peak width, if H is constant. However, the additional effect of carrier gas properties (diffusivity and velocity) should be taken into account, for a range of k'-values. For k'=0.1 and comparing the capillary with pressurized $H_2$ vs. PHASED with air/$N_2$ carrier gas, one may get, for a PHASED square cross section channel with L=25 cm, an equivalent hydraulic ID of also 100 µm, and a film thickness of ~0.1 µm, an optimal $N_2$ velocity of 174 cm/s and a resolution* of 15.5, via Golay's equation. For a capillary with L=150 with an average $H_2$ gas pressure of 59+15=74 psia, a $H_2$ diffusivity of D=5×$D_o$, and the same ~0.1-µm film thickness, one may get an optimal velocity of 93.34 cm/s with a resolution of 38. But at the set average velocity of 5.55-6 m/s to meet analysis speed goals, just a resolution* of 21.6 could be used.

Thus, for k'=0.1, PHASED resolution* may be lower than that of the used capillary by a factor of 2×(one wall vs. circular channel), multiplied by the ratio of resolutions, 21/15.5=1.39, for a total loss of about 2×1.39=2.8×. For k'=10 and comparing the capillary with pressurized $H_2$ vs. PHASED with air/$N_2$ carrier gas, one may get, for a PHASED square cross section channel with L=25 cm, an equivalent hydraulic ID of also 100 µm, and a film thickness of about 0.1 µm, an optimal $N_2$ velocity of 67.2 cm/s and a resolution* of 9.5, of which only 7.8 might be used if velocity is optimized for k'=0.1, rather than for k'=1 with v(optimal)=98 cm/s.

For a capillary with L=150 and an average $H_2$ gas pressure of 59+15=74 psia, a $H_2$ diffusivity of D=5×$D_o$, and the same ~0.1-µm film thickness, one may get an optimal velocity of 35.9 cm/s with a resolution of 23.4, but at the set average velocity of 555 cm/s, just a resolution* of 8.4 might be used. Thus, for k'=10, the PHASED resolution* may be lower than that of the capillary by a factor of 2× (one wall vs. circular channel, multiplied by the ratio of resolutions, which may be near 1 in this case, for a total loss of about 2×.

Figure 22:
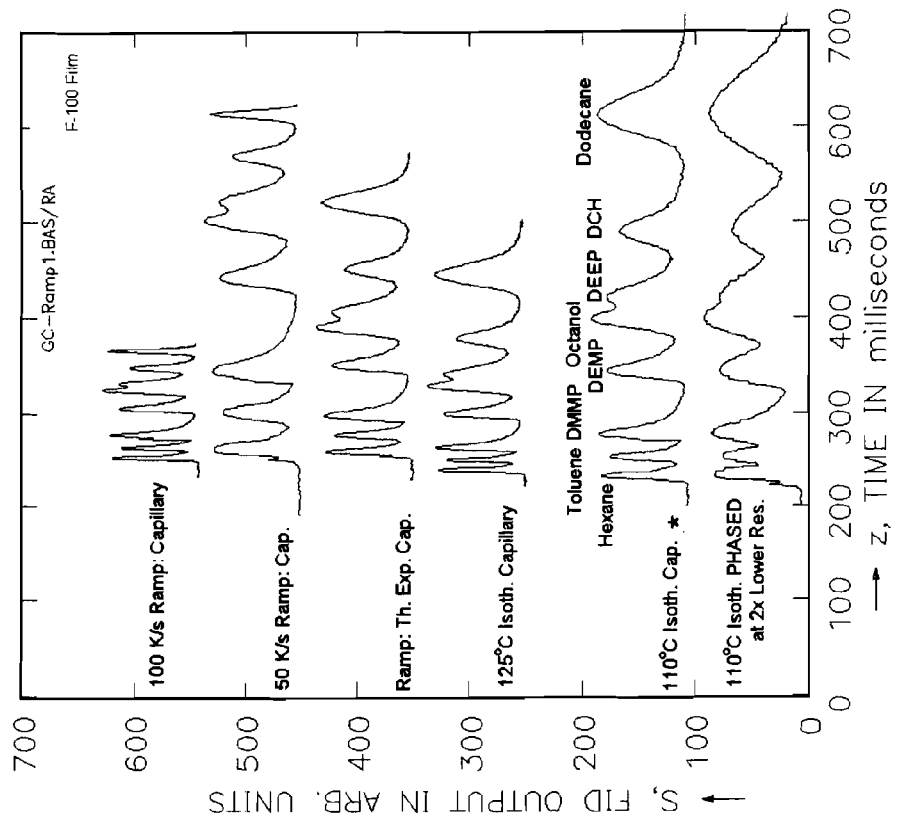
FIGS. 22 and 23 are gas chromatogram plots.
Figure 23:
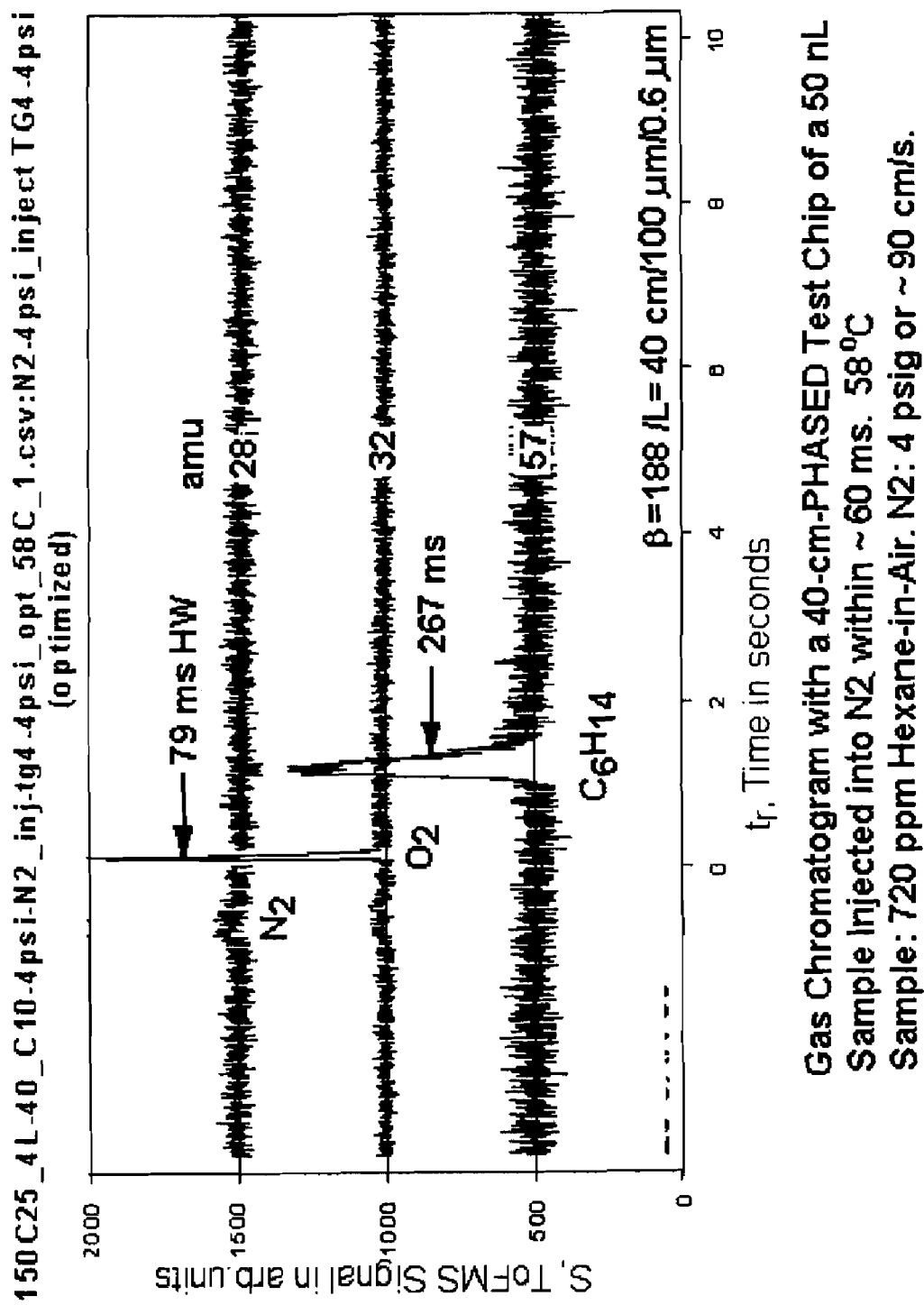

A simulated gas chromatogram having this 2×lower resolution may be plotted in FIG. 22 (first curve from the bottom) by increasing the width of each half-peak (assumed Gaussian) by 2×. It may represent a PHASED separation of the same 4/4 mixture of gas analytes, but with L=25 cm, 100-µm-square channel, v~70 cm/s, with just one wall coated, and an isothermal run at 110° C. As shown, the degradation relative to the second capillary curve in FIG. 22 appears noticeable but not signification. Additional experimental results may be presented in FIGS. 23 and 24:

FIG. 23 shows mass traces resulting from separating an approximate 80 ms injection pulse of 50 nL of the 720 ppm hexane-in-air sample into a $N_2$ carrier gas before flowing into a PHASED chip having a 42-cm long microchannel coated on one side with 0.6 µm of NGE and using a Leco ToFMS as a detector. A sharp $O_2$ peak should be close to the to time. The hexane peak S/N may indicate a MS MDL of about 40 ppm (for a zero-to-peak S/N of 1).

Figure 24:
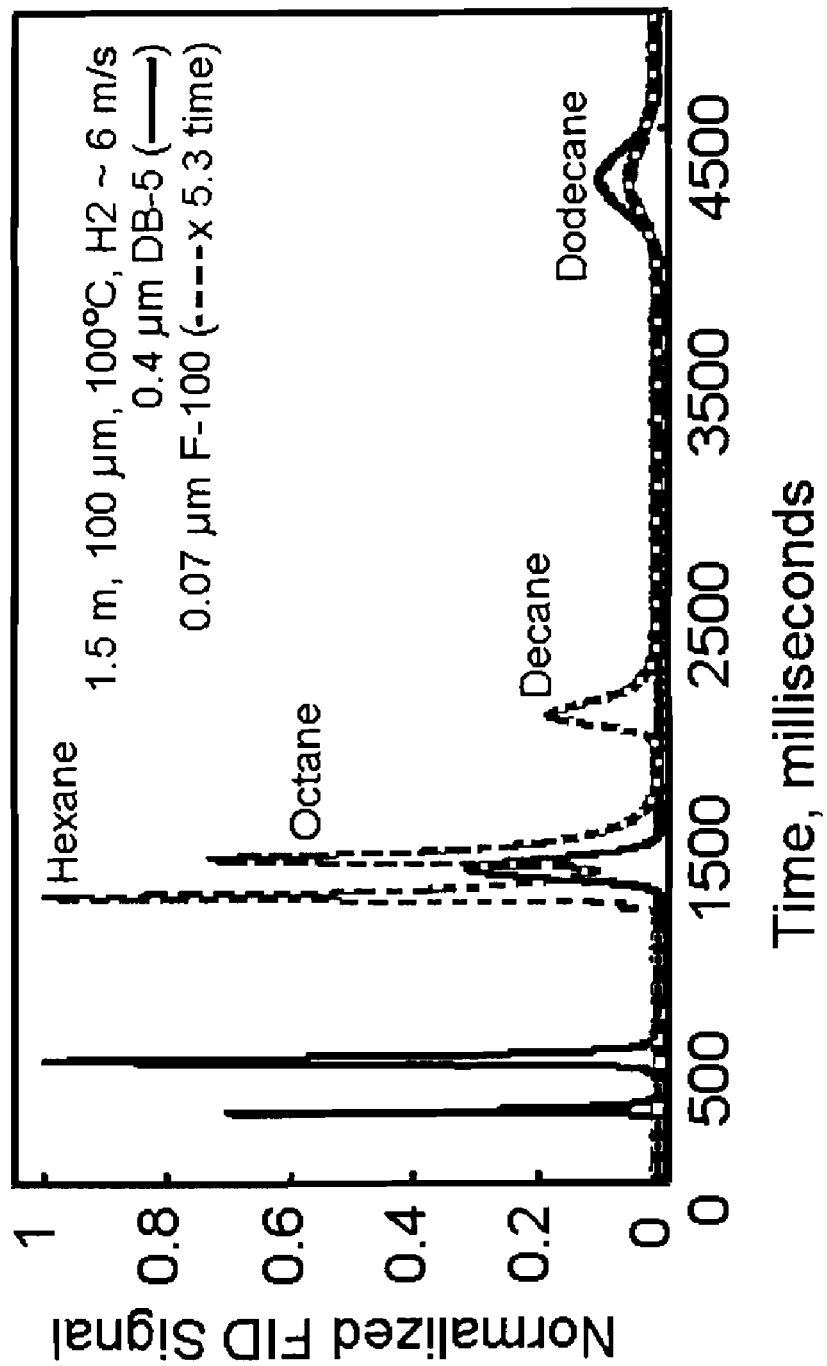
FIG. 24 shows a comparison of alkane separation between stationary phases.

FIG. 24 shows a comparison of alkane separation with two different PDMS films doped, one with phenol (DB-5) and the other with silylarylene (F-100). Their approximately 5× different thicknesses may cause the largest difference in elution time, but their chemistry would appear responsible for the different retention ratios.

One may note column temperature ramping. Building on the chromatograms shown in FIG. 18, one may predict the benefits of temperature ramping and changes in column geometry. In effect, one may digitize the isothermal chromatogram (110° C., eight components separated on a thin, polar stationary phase) and then move the time scale in accordance with the influence of temperature on k': $t_r=t_o\cdot(k'+1)$. From the k' vs. T data in FIG. 18 one may derive the temperature dependence of k' for the compounds from hexane to dodecane and note that it may take a ramped temperature change of $\Delta T$=17 to 26° C. to change k' by a factor of 2×.

Figure 18:
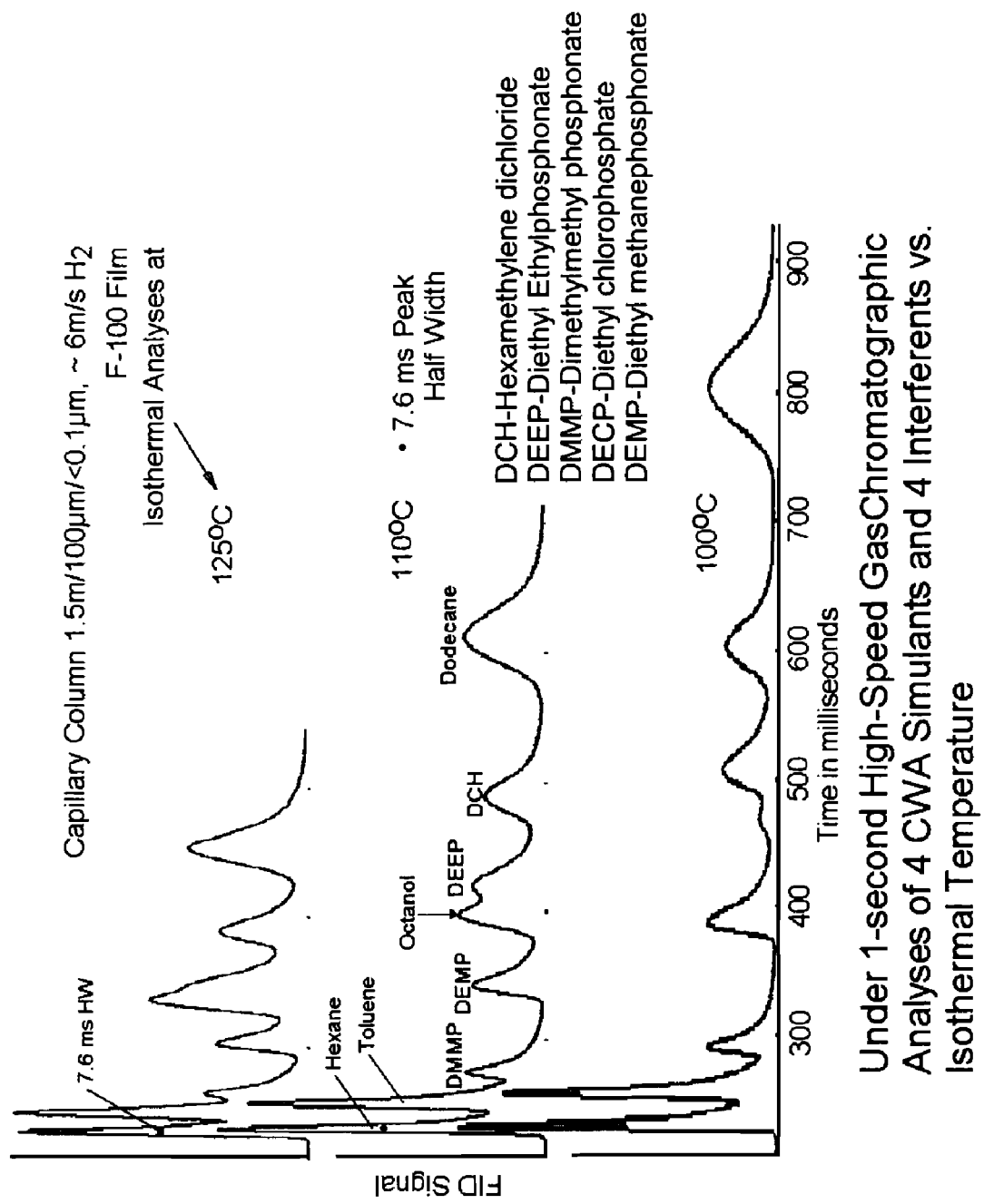
FIG. 18 is a graph of simulants versus isothermal temperature.

Using a simple factor of $2^{(\Delta T/18)}$ and trying out various T-ramping functions may result in the computed chromatograms in FIG. 22, of which the bottom one may correspond to a simulated PHASED with a 2× lower resolution* than the 110° C. chromatogram of FIG. 18. On all traces in FIG. 22, the FID signals for hexane and toluene may be digitally reduced to 25% of their experimental value for the sake of clarity. Except for the bottom trace (number 1), all other shown traces may represent 1.5-m capillary-based results. Moving up from the bottom, the number 2 trace may be is the original 110° C. isothermal (no temperature ramping) chromatogram of FIG. 18. Trace number 3 may show a simulated 125° C. isothermal chromatogram, comparing favorably with the measured one in the middle of FIG. 18, and based on reducing all k' by approximately 2× and including the higher flow velocity caused by thermal expansion. Trace number 4 may just consider the thermal expansion effect of a 200° C./second temperature ramp, without changing k'.

Trace number 5 may be a simulated chromatogram resulting from a temperature ramp rate of 50° C./second, after holding its start for ~200 ms after $t_o$. Trace number 6 appears similar to trace number 5, except for a 2×larger ramp rate (100° C./s) to show that excessively high ramp rates may be detrimental by causing retention times of different compounds to get too close to each other. Rather, a carefully selected ramp rate could optimize resolution and peak capacity.

These measurements and simulations of the PHASED operation with ramp rates of only a 50-100° C./s indicate that the eight peaks from the experimental chromatogram may be eluted within the first 400 ms, and over 50 peaks within <1 second (including $t_o$).

Pre-concentration modeling may involve a multistage PC model from first principles and to be compared with experimental data. Such data may be obtained with 20 elements of a PHASED-chip PC heater array, in which these 20 may be exposed to a constant flow of air with 720 ppm of hexane and then subjected to phased, individual desorption pulses of 6 ms each. In this way, the desorbed hexane from all elements may contribute to the injection pulse, which may lead to the TCD and ToFMS traces shown in FIG. 25.

With desorption pulse lengths decreased from 20 to 6 ms and increased desorption peak temperatures from about 135 to ~165° C., i.e., closer to optimal conditions, may enable an increase in the equivalent (i.e., corrected for the total peak broadening including diffusion-broadening as the peak traveled from the PHASED chip to the mass spectrometer) PC gain for hexane from 34× to about 62×, despite the still sub-optimal sample flows (about 60 cm/s rather than about 110 cm/s) and some remaining electrical and fluidic leakage. One may continue to use the 720-ppm hexane source because of its convenience (no toxicity and little danger of condensation due to its high vapor pressure, but its high volatility may make for difficult PC conditions). The stationary phase film, as above, may be 0.6 μm of NGE, which has been spin-coated onto the 4" heater wafer of PHASED.

Figure 28:
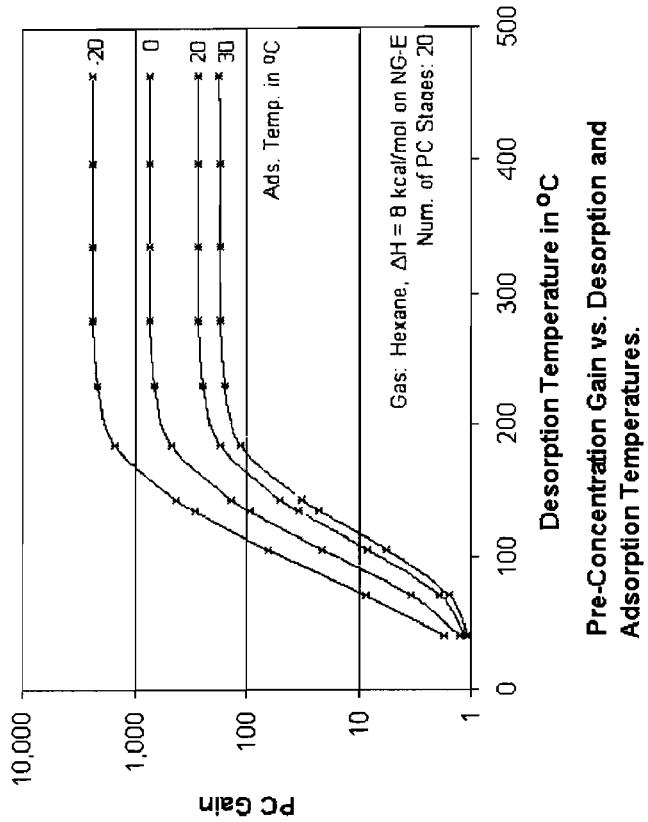
FIG. 28 is a graph of pre-concentration gain versus desorption and adsorption temperature.
Figure 27:
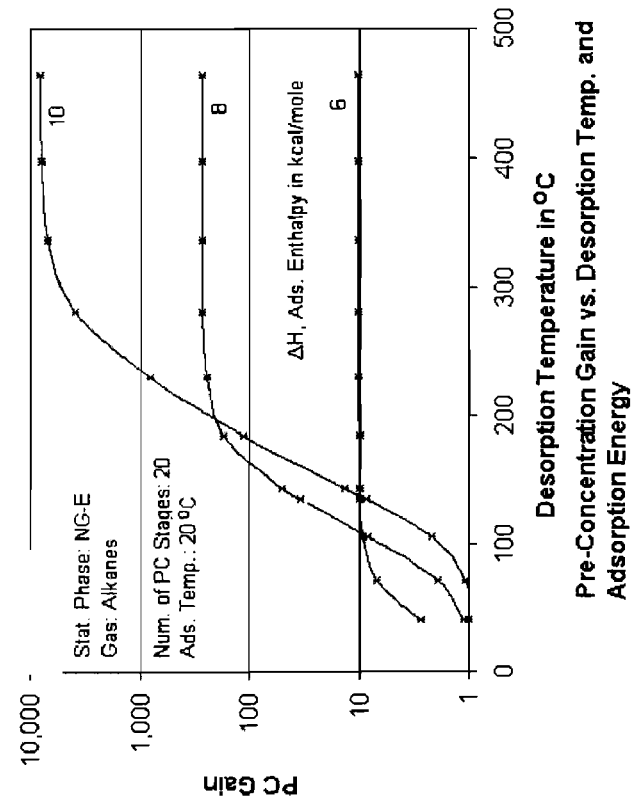
FIG. 27 is a graph of pre-concentration gain versus desorption temperature and adsorption energy.

The modeled and experimental gains may be translated to those for lower vapor pressure analytes by virtue of their known partition coefficients (K-values). For the available experimental conditions, the above PC gain data may agree with calculated results, which could be then extrapolated with high confidence to those >10,000× gains achievable with analytes of larger adsorption energies at higher sample flows and larger desorption temperatures, as shown in FIGS. 26, 27, 28 and 23, revealing sensitivity to desorption temperature (to get all analyte to desorb) as the independent variable in all figures, number of effective PC stages (FIG. 26), analyte heat of adsorption (FIG. 27), and adsorption temperature (FIG. 28).

Figure 9:
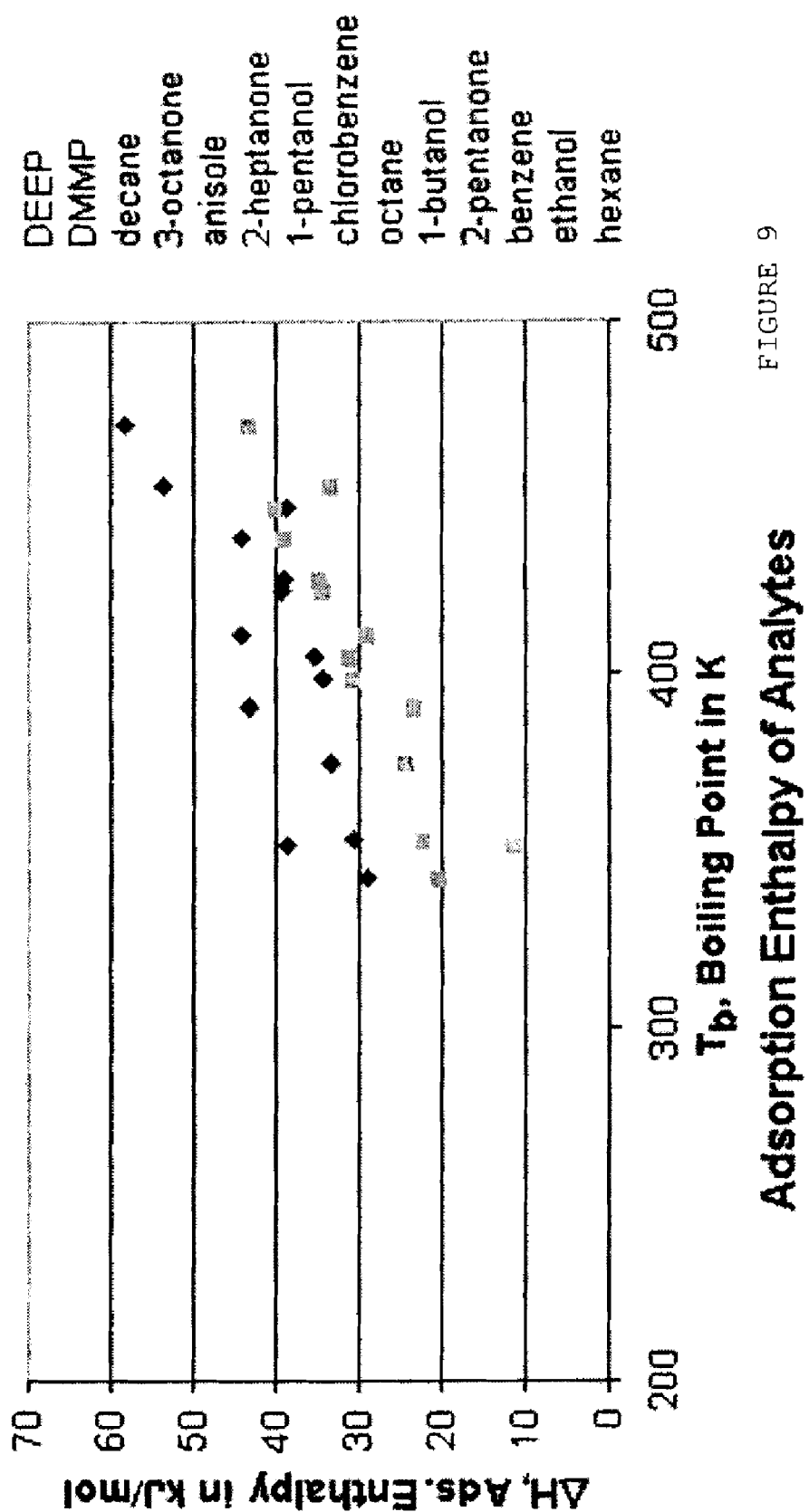
FIG. 9 shows adsorption enthalpy of analytes.
Figure 25:
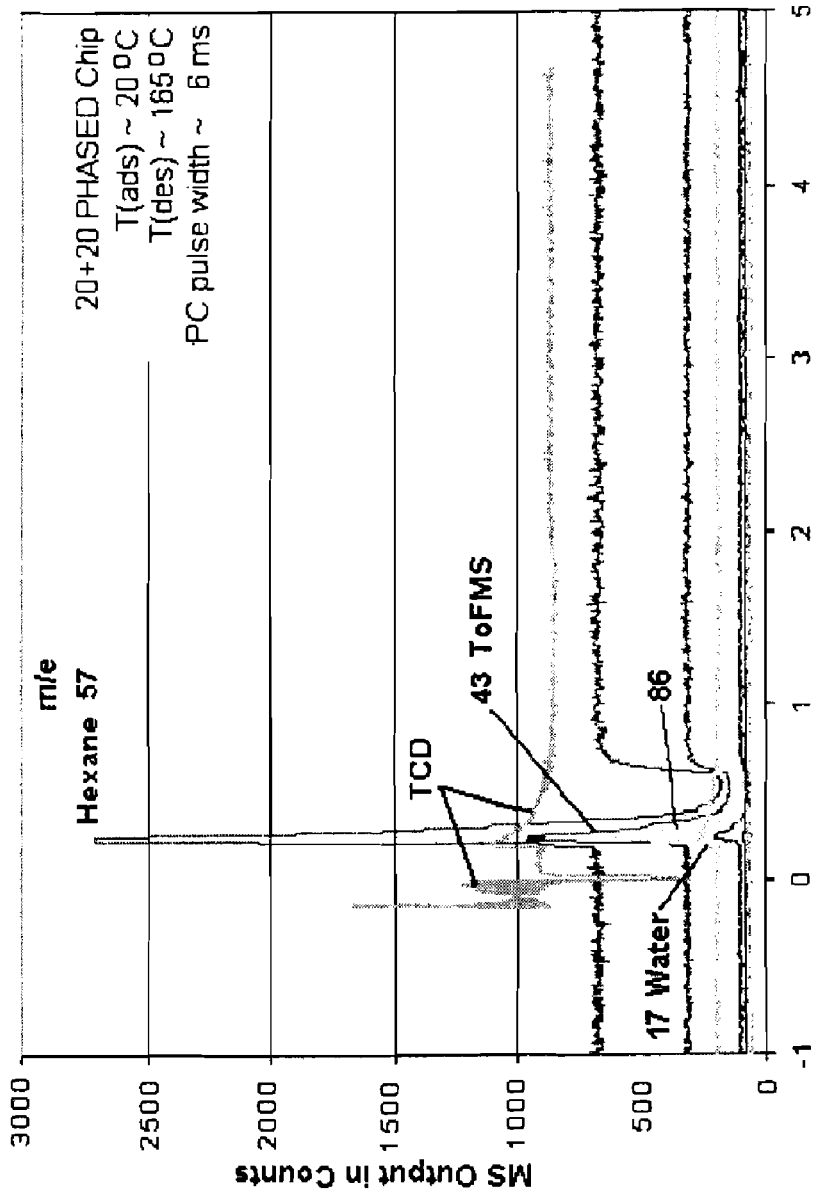
FIG. 25 is a graph of detector outputs versus time of a fluid analyzer.
Figure 26:
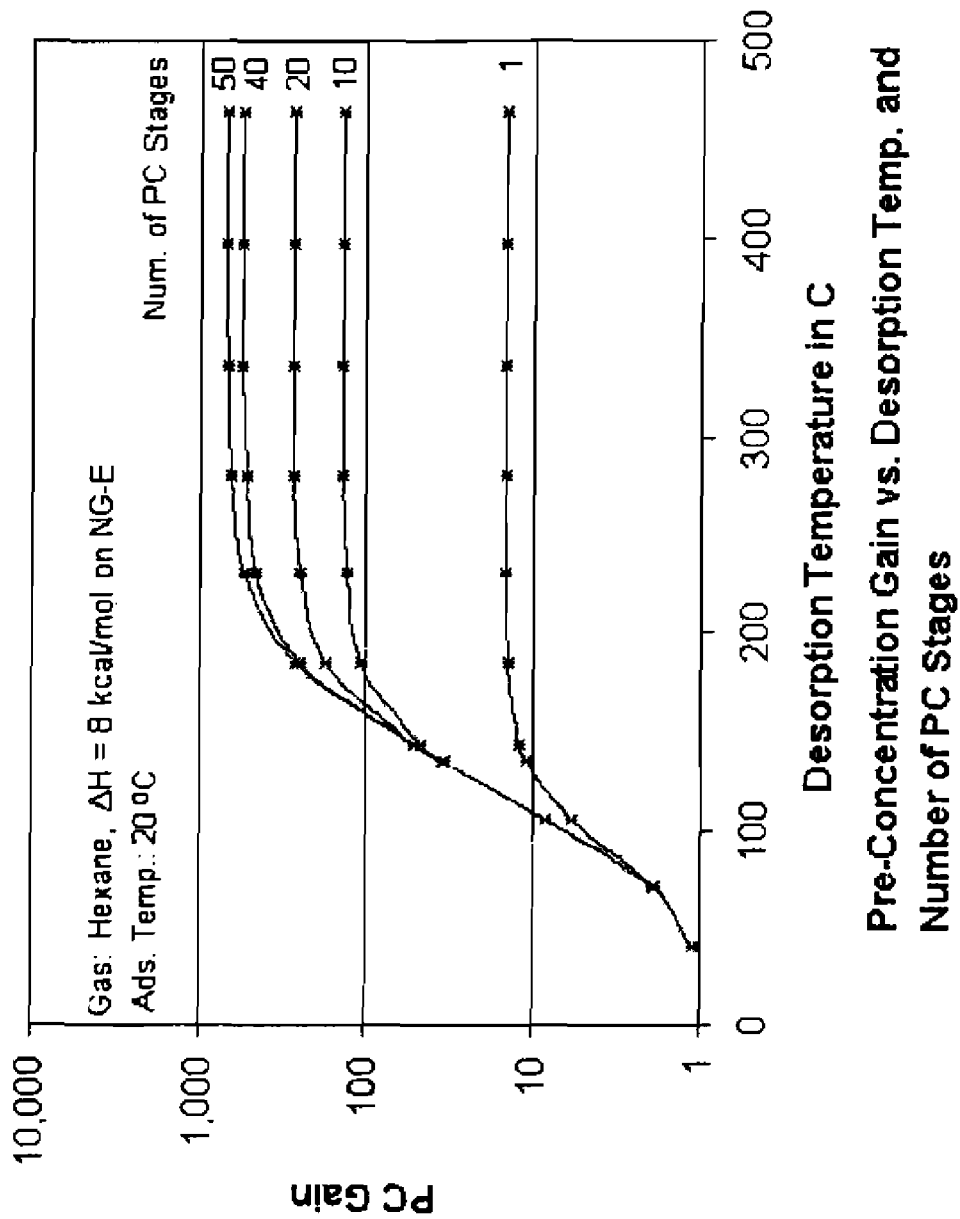
FIG. 26 is a graph of pre-concentration gain versus desorption temperature

The modeling results appear to compare favorably with the experimental data of FIG. 25: The hexane peak height may be about 5.2× higher than the 720-ppm baseline MS (time-of-flight mass spectrometer) trace, but due to sub-optimal flow and diffusion during transport through the separator and beyond it to the MS, the peak appear to be broadened about 12× over its optimal approximate 7-8-ms peak-width at the start of the separation. If one assumes a triangular shape of the peak, its height may be about 5.2·12=63× higher than the 720-ppm baseline. The calculated PC gain for hexane for 20 PC stages, 20° C. adsorption, 165° C. desorption temperatures and hexane vaporization/desorption enthalpy, $\Delta H$, between 28.85 and 20.42 kJ/mole (6.89 and 4.87 kcal/mole), according to literature, and GC experimental results with DB-5[5], respectively, may yield PC gain values between 125 and 4×. The difference between this and the noted experimental value of 63× should not be attributed only to uncertainty of the model but also to the variability of $\Delta H$, which for "unprocessed" NANOGLASS™ may be measured to be about 1.2× higher than the literature value for vaporization enthalpy, $\Delta H_v$, but measured to be about 1.2-1.7× lower for DB-5 than $\Delta H_v$, as noted in conjunction with FIG. 9. If that factor is taken into account, together with increases in the desorption temperature to 200° C. and the number of PC stages to 50, then calculated PC gain may be about >3700× for NGE. This gain could be higher still for films of thickness greater than the 0.6 μm used in the representations of FIGS. 26, 27 and 28, and for film-analyte combinations exhibiting greater adsorption enthalpies and K values, of which had been shown a range in FIGS. 7, 8, 9 and 11.

An estimation of a polymer sensor response may be made. Polymeric stationary phase thin-films may perform a third function in GCs, i.e., detection, besides pre-concentration and separation of analytes. Such polymer film detection of analytes may be based on changes in the film's electrical resistance, capacitance or stress. Capacitance-based detectors may be used in PHASED in addition to the present differential TCD and others, due to their fabrication compatibility.

Estimation of detector performance with new analytes may be a challenge in analyzer applications, whether in the industrial, medical, environmental or homeland security fields, even if only the presence or absence of an analyte is to be detected. However, many applications may require that this detection be accomplished with a low rate of failure and specifically a low rate of false-alarm or false-positive failures. To meet this need, one may engage several diverse detectors based on different physical sensing phenomena. Each of these detectors may have its own weaknesses or "blind spots," such as the thermal conductivity detector for sensing analytes of thermal conductivities close to that of the background or carrier gas, the flame ionization detector for sensing analytes that do not generate ions in a hydrogen flame, or the capacitive polymer sensor for analytes with dielectric constants or other properties close to that of the carrier gas in relation to the polymer film itself.

When polymer detector films are exposed to analytes, their gas-phase concentration may establish an equilibrium concentration in the film, which may be quantified by the same equilibrium or partition coefficient, K, as noted in conjunction with the prediction of retention times. Others have related this partition coefficient of an odorant or analyte to the vapor pressure of the analytes, and shown that low-ppm sensitivity of such polymeric films to several analytes may be achieved via capacitance measurements. One may want to predict such sensitivity on the basis of measured or calculated K values. One may assume that the film is thin enough to render transport and diffusion effects negligible while enabling a focus exclusively on equilibrium phenomena as determined by K, whether associated with film swelling or not. A source of K data for several types of polymers may be available, associated a characterization of the performance of SAW (surface-acoustic wave) detectors.

To calculate the response of a capacitive sensor, one may envision an interdigitated pair of electrodes deposited onto an insulating and low-dielectric constant substrate, onto which the sensing film might be deposited. To achieve the desired millisecond response time, one may use sub-micrometer film thickness, as used with high-speed gas chromatographers. The detector signal may then be measured and computed on the basis of the change in composite dielectric constants between those of the film-host plus either the carrier gas or the adsorbed and solvated analyte.

One may derive an approach to estimate liquid dielectric constants, $\epsilon$ (i.e. polarity of analytes or stationary films), partition coefficients, K, retention factors, k', and retention times, $t_r$, for any analytes of which only boiling point, $T_b$, and elemental compositions are known. Boiling point, $T_b$, may provide the main basis for approximate prediction of k' and K of analytes, whereas their elemental composition may enable a rough estimation of their polarity, (low-frequency) permittivity or dielectric constant, $\epsilon$, which in turn may reduce uncertainties in estimation of K-values by factors of 2-4× below estimates based on $T_b$ alone. This modeling effort may provide unexpected insights into the relationship between K and polarity of hypothetical analytes of equal $T_b$ but increasing $\epsilon$, which may show reduced K-values and retention time as their polarity increases beyond a point at which K has reached a maximum.

With derived K and k' values and their estimated film adsorption enthalpy, one may simulate and visualize the benefits of controlled temperature ramping of the separation column, either by extending the results of experimental isothermal GC separations or by generating such chromatograms from scratch. This may enable one to project how to meet and exceed specified peak capacity and of separation time for a given range of analytes.

To predict and meet specified MDLs (minimum detectable limits) and thus predict PC gains for given analytes, a first-principles model of the multi-stage PC may be validated with experimental data from a PHASED chip. The model may enable one to quantitatively predict the performance and limitations of achieving preconcentration gains with a one-level PC as a function of the number of its stages, soaking and discharge temperatures ($\leq 300°$ C.), and the adsorption/solvation enthalpy of the analytes of interest, which may typically fall in the range between 6 and 15 kcal/mole or 20 and 70 kJ/mole.

There may be experimental data that could be translated into a calculated separation performance of an available PHASED chip with separation channels of up to 25 cm in length, to achieve peak capacities >20 within 1-second analysis times, particularly if temperature ramping is included.

The K- and $\epsilon$-values may be used to estimate the performance of polymer gas sensors as GC detectors. This and the determination of the influence of $\epsilon$ of the stationary phase on K, and the stability of stationary-phase films over time after exposure to water vapor and after patterning with a photoresist, might be used to evaluate stationary-phase films for micro-analytical measurements.

There may be applications of advanced film materials, such as various flavors of high specific surface area, nanoporous organosilicate films (spin-on glass (SOG)), which may be coated onto wafers or into capillaries.

There may be molecular modeling of analyte adsorption on MEMS GC stationary phases. Future microelectromechanical systems (MEMS), nanoelectromechanical (NEMS), and micro-optical electromechanical systems (MOEMS) may require a distinct understanding of interfacial effects in order to predict their performance and to reliably manufacture these devices. Molecular modeling may be a tool for simulating and understanding critical working interfaces by modeling the atomic mechanics during performance.

Molecular modeling may be used for improving materials used in MEMS devices using as example the comparative performance of materials for stationary phases in gas chromatographs. This comparison may be based on derived interaction enthalpies between analytes and stationary phases and using simulations of surface separation by employing molecular dynamics. The separation performance may be compared to experimental GC data, showing that qualitative comparison of separation may be present from the molecular scale and confirming that molecular modeling may be a useful tool to pre-select stationary phases for specific activity.

Figure 6:
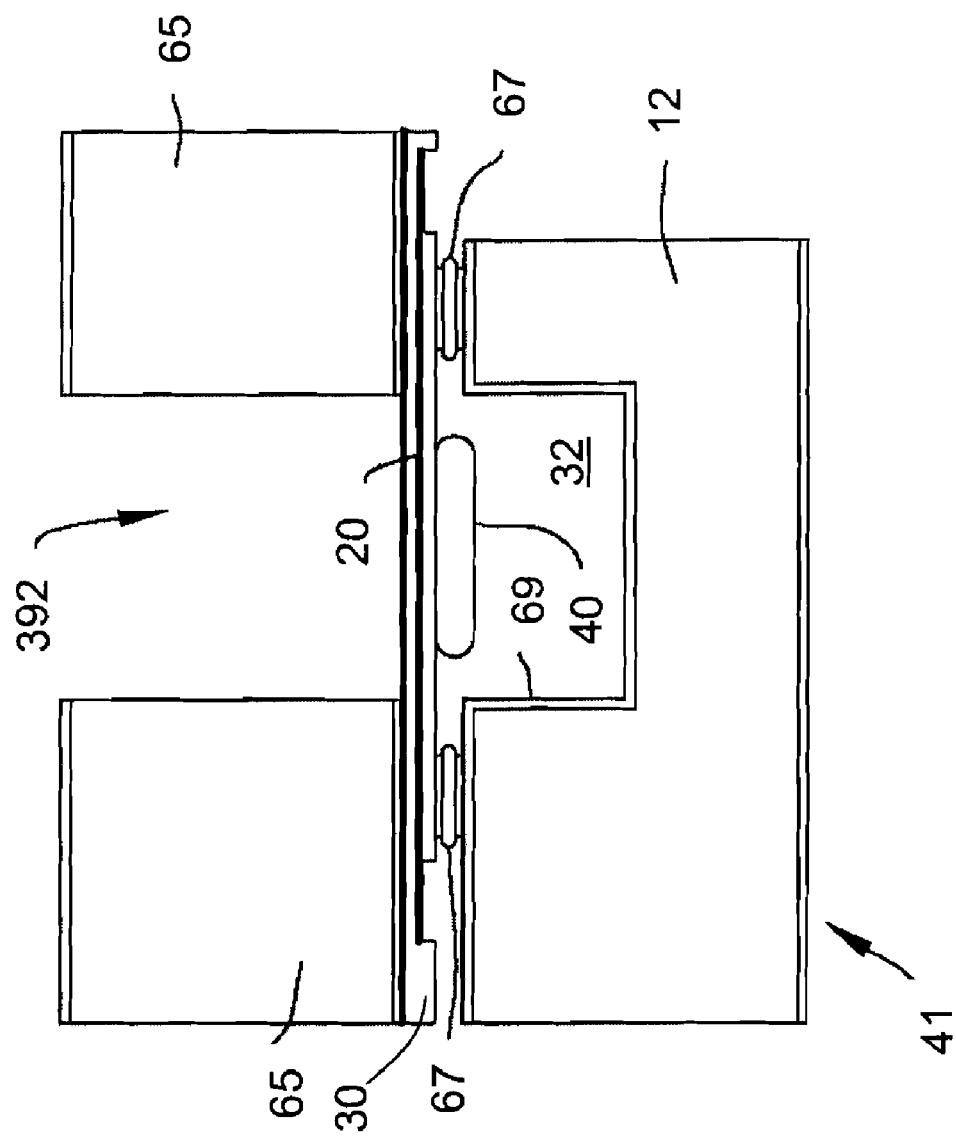
FIG. 6 shows a cross-section end view of a single film element.

A MEMS analyzer may be a miniaturized gas chromatograph (GC) with ultimate goals of pre-concentration, separation and detection within 3 seconds, sensitivity of less than 1 ppb and a total packaged size of less than 200 cm3. The active capture and separation of analytes may utilize an array of heatable adsorption-desorption microelements (which led to the name "PHASED" for phased heater array structure for enhanced detection). Pre-concentration, separation, detection, and flow and temperature sensing functions may be integrated onto one chip. The present microanalyzer may be envisioned for applications such as industrial chemical process control, environmental monitoring, security and medical diagnostics. A schematic of the MEMS analyzer (e.g., a PHASED system) is shown in FIG. 5. A cross-section of a stationary phase adsorption (Ads) layer 40 in channel 32 is illustrated in FIG. 6.

A significant material needed for the basic analyzer function may be the stationary phase film in the preconcentrator, separator and even in some types of detectors such as CIDs (chemical impedance detectors). Possible structural failure modes for this stationary phase may include delamination and film cracking, but the key operational parameters requiring understanding in order to achieve the desired performance may be analyte adsorption thermodynamics, involving rates, film capacities, chemical kinetics and analyte permeabilities. Pre-concentration and GC separation performance may then be the natural consequence of these.

Because a quantitative understanding of the adsorption/desorption enthalpies for each individual analyte appears important to the design and analyzer performance prediction, molecular modeling may be used to simulate the thermodynamic response of the adsorption/separation surface to envisioned analytes under dry and humid conditions, in order to predict the ultimate response of the MEMS analyzer.

The notion of stationary phase function in gas chromatography may be represented by the Golay equation—equation 1 where H=theoretical plate height; $D_m$=diffusivity of analyte in mobile phase; v=average mobile phase velocity; k'=retention factor; r=column radius; $D_s$=diffusivity of analyte in stationary phase; and $d_f$=the thickness of the stationary phase.

$$H = 2D_m/v + [(1+6k'+11k'^2)/(1+k')^2][r^2/(24D)]v + \tfrac{2}{3}[k'/(1+k')^2][d_f^2/D_s^2]v \qquad (1)$$

The theoretical plate that may determine the efficiency of the stationary phase, and the GC column (and is usually defined by the length of column divided by the number of theoretical plates, where the total number of theoretical plates in the column is defined by the the retention distance and peak width by n=4× (retention distance/peak width)$^2$. Because the theoretical plate height may describe the average length of column that will separate distinct GC peaks, in order to reduce the size of the column, the theoretical plate height should be minimized. This aspect appears to be significant for a MEMS GC device, which should have the highest efficient stationary phase to accommodate performance on a chip-sized design.

In the Golay equation, the term that may be most impacted by the stationary phase is k' (which is the ratio of the retention volume to the mobile phase volume and may be measured from the retention times of the chromatogram), as this ratio is related to the equilibrium constant K where k'=Kβ, and where β is the volumetric ratio of the two phases (stationary/mobile phase). The equilibrium constant or partition function, K, may represent the concentration ratio of analyte in the stationary/mobile phase. K and k' may be determined by molecular modeling.

If one concentrates on other terms which involve the stationary phase, besides k', the thickness of the stationary phase ($d_f$) and diffusivity of solute in stationary phase ($D_s$) may be considered. Decreasing the stationary phase thickness may improve the separation by decreasing the theoretical plate height, but this may lend insight into how the stationary phase is performing as it seems to suggest that at the limit of thickness the theoretical plate improvement may be due to a surface rather than a bulk effect.

When considering general diffusivity theory, D may be defined as:

$$D = (kT/h)d^2 \exp(-E/RT) \qquad (2)$$

where d is the elementary distance traveled; in a solid it may be the lattice distance, and kT/h may have dimensions of a frequency. When applied to stationary phases and the Golay equation, this relationship suggests that to minimize H, a larger elementary distance may be required. Because a larger elementary distance implies a lower density (or a larger path d), this interpretation suggests that an extremely low dense material should increase d thru a higher path tortuosity, and help keep H low thru the diffusivity part of the Golay equation. Thus, from the Golay equation, there may be an interaction between the adsorptivity of the material and the path that the analyte should undergo. The molecular model may examine the adsorptivity. That may lead to the thermodynamic terms of the Golay equation and also the quality of the surface dynamics that address the surface quality. Examination of larger models may also begin to address the quality of the pathlength, but cannot seem to contain the entire path of the analyte molecules as the size of these types of models may be usually too large to consider. An obvious extension to the molecular model for this modeling community may be a use of a discrete element model, parameterized from the molecular scale.

To evaluate, qualify and rank the best materials to be used for the active adsorption surfaces, one may look for an approach to predict adsorption enthalpies and free energies as the initial representation of k'. For seeking molecular mechanics and dynamics modeling results, the Accelrys software Discover may be used, employing the CVFF (consistent valence force field) force field.

Figure 29:
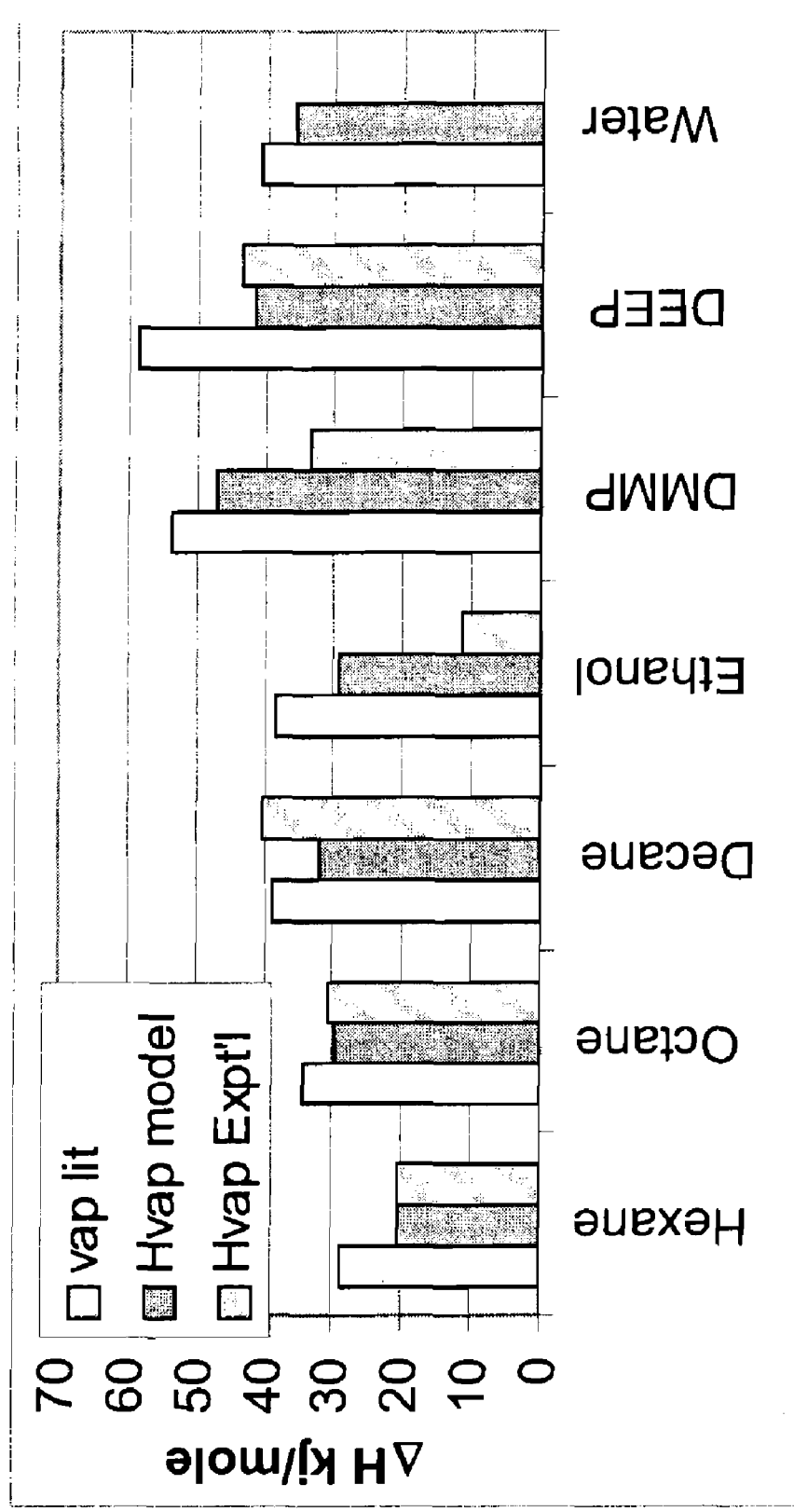
FIG. 29 shows a value of ΔH kj/mole for various materials.

To study the thermodynamic part of the Golay equation, vaporization/condensation enthalpies may be first computed and then compared to relevant literature values to validate the model. For benchmark vaporization energies, the target masses may consist of randomly generated cells of the analyte, containing up to 50 molecules of the analyte. The differences from the separated species may be used as the vaporization energy. A temperature adjustment may be made using RT in order to estimate the enthalpies. These items are shown in FIG. 29 (where DMMP=dimethylmethylphosphonate and DEEP=diethylethylphosphonate) and may be compared to relevant literature, and also compared to the vaporization energies measured using GC data. The results from the models appear to indicate that the calculations are consistently low in enthalpy when compared to the relevant literature, but that the trends appear similar indicating possibly useful comparison.

Figure 30:
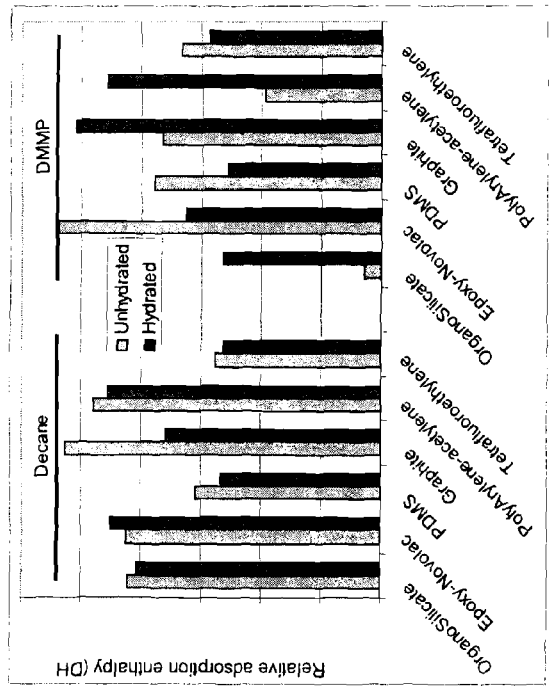
FIG. 30 shows a relative adsorption enthalpy for various materials.

In order to generate adsorption enthalpies, the target surface masses may be generated using an amorphous mass, and the specific analyte may be energy minimized onto the surface. The differences from the separated species may be used as the adsorption energies. An RT adjustment may be made in order to estimate adsorption enthalpies (ΔH) as a first approximation of k'. The models may be generated for both dry and humid conditions for a variety of analytes. Preferred film materials may be sought whose adsorption enthalpies are the least affected by the presence of water vapor and also show distinct enthalpy values for as many as possible of the analytes of interest. An example of the noted stationary phases are shown in FIG. 30, showing how a highly polar analyte such as DMMP (dimethylmethylphosphonate) may be highly sensitive to the hydrated conditions of the stationary phase.

Because GC separation generally follows a boiling point (BP) trend, the adsorption free energies and boiling points may also be noted. In order to do this, a closer estimate of the equilibrium constant K (and thus a closer estimation of k') may be had by estimating the free energies of adsorption by inclusion of the entropic effects of Trouton's rule (S=H/RT at BP). These may be considered minor modifications to the enthalpy, and that the energy trends generally remain the same, they may be included because of the better theoretical linkage between free energy and K.

Figure 31:
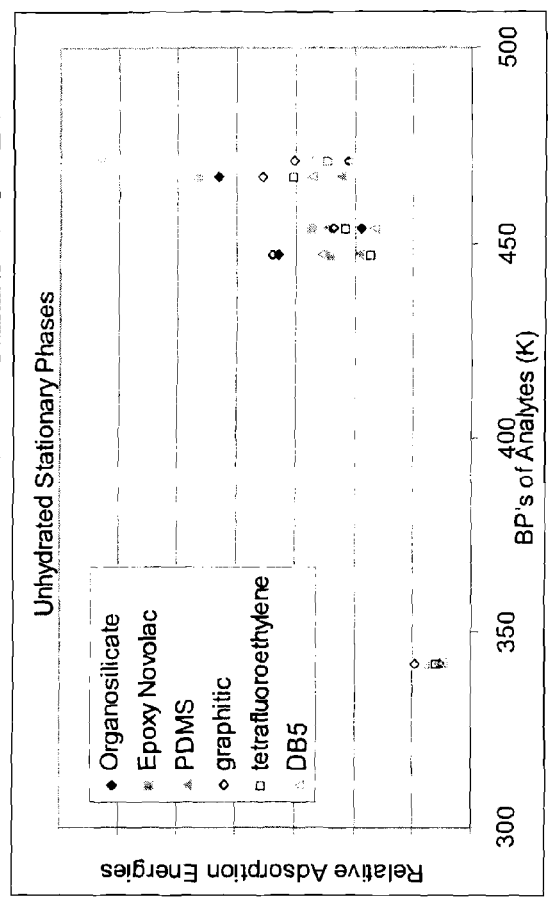
FIGS. 31 and 32 show relative adsorption energies versus boiling points for various analyte materials for unhydrated and hydrated stationary phases, respectively.
Figure 32:
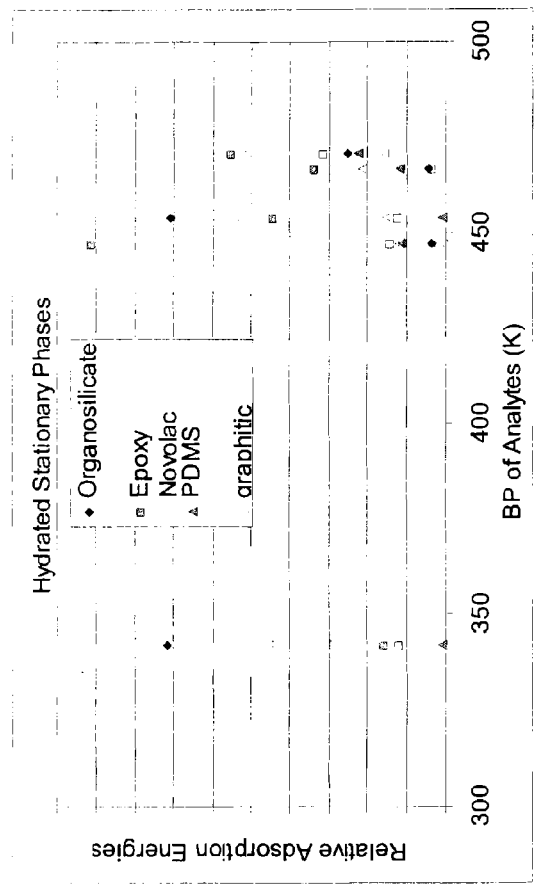
Figure 33:
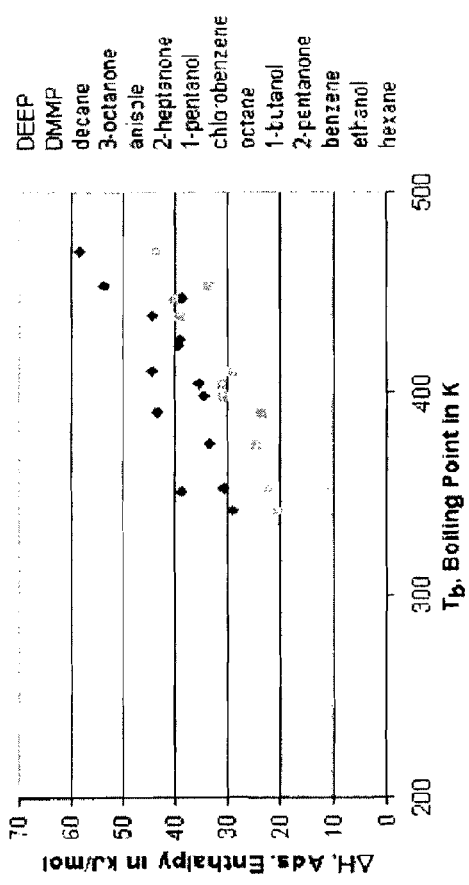
FIG. 33 is a graph of adsorption enthalpy versus boiling point for various materials.

The free energy trends with boiling points are shown in FIGS. 31-33. FIGS. 31 and 32 show the modeled trends where the modeled analytes are dimethylmethylphosphonate, diethylethylphosphonate, diethylmethylphosphonate, hexane and decane. FIG. 33 shows trends using the measured enthalpies showing the linear trend of boiling point with measured adsorption enthalpies. A comparison of FIGS. 31 and 32 suggests that hydration may also disrupt an expected adsorption energy trend with the BP.

FIG. 12 shows vaporization modeling benchmarks compared to the relevant literature and experimental values generated from GC analyses. FIG. 13 shows enthalpy comparisons of a highly nonpolar to highly polar analyte on various polarity stationary phases.

Figure 34:
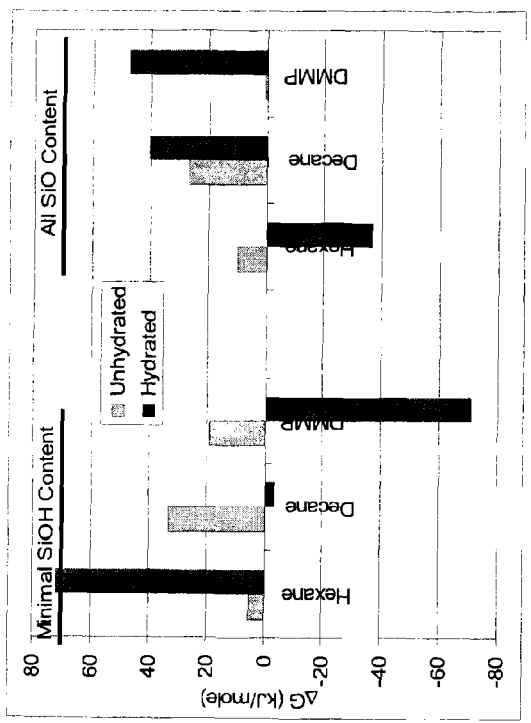
FIG. 34 shows SiOH and SiO contents of materials for unhydrated and hydrated situations.

One aspect of the specific structural effects is shown in FIG. 34, in which silicate models may be adjusted for silanol ("organosilicateOH") content and the free energies of adsorption may be compared. There appears to be a significant loss in adsorption for DMMP when there is silanol content coupled to a hydrated surface. But in general, the trends with hydration and silanol content appear not consistent in suggesting that the silicate condition is exceptionally important in order to maintain predictable performance.

Figures 14, 15:
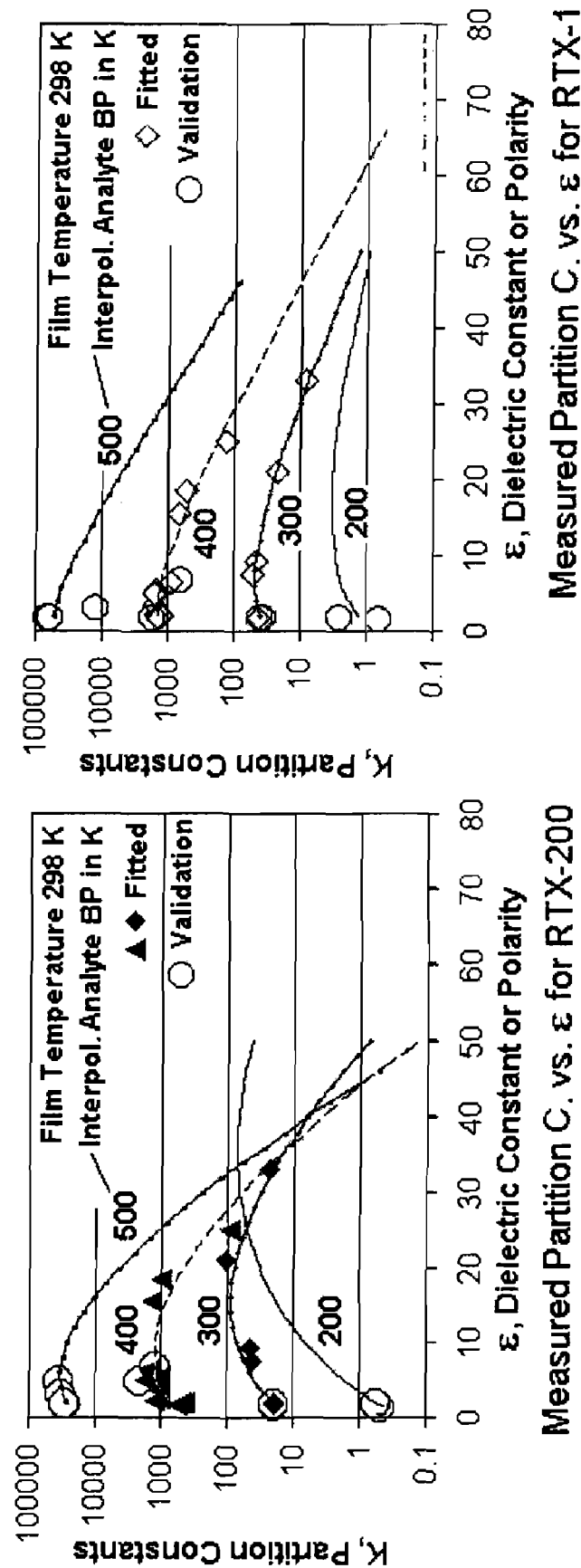
Figure 16:
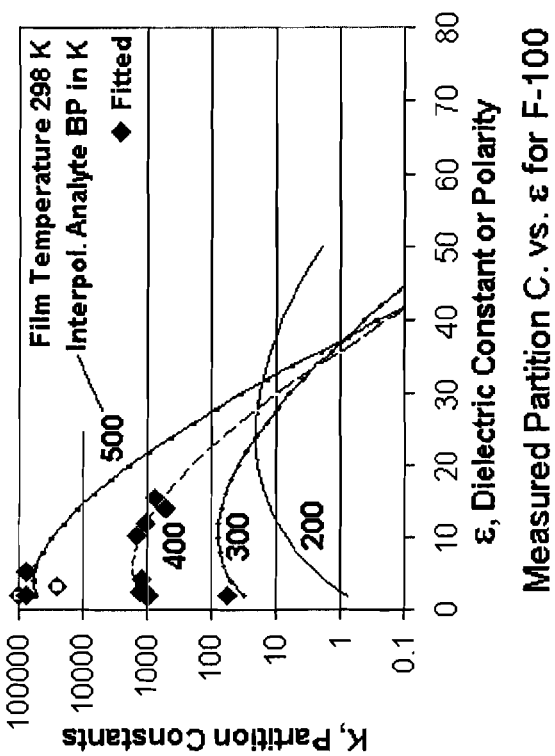

FIG. 14 shows boiling point trends of adsorption energies for the unhydrated state of the stationary phases. FIG. 15 shows boiling point trends of adsorption energies for the hydrated state of various stationary phases. FIG. 16 shows experimentala adsorption enthalpy trends with a boiling point. FIG. 17 shows adsorption enthalpy changes with SiOH content in an organosilicate-based stationary phase.

Among the stationary phase film materials evaluated, organo-silicates, epoxy-novolac, PDMS, carbon surfaces represented by graphite/carbon nanotubes (which may be of importance to new GC stationary phases being developed) and polyarylenes (derived from low-k dielectrics), and finally tetrafluoroethylene. All show different ΔH (and ΔG) dependence on the presence of water. In general, those materials with low polar content like the graphite or polyarylenes, appear to have the lower interference to moisture. However, those highly hydrophobic surfaces like graphite and the polyarylenes, appear to have higher DMMP adsorption when hydrated suggesting the importance of a polar nature of the stationary phase surface when adsorbing polar analytes. A significant surface is tetrafluoroethylene which appears to contain the high individual bond dipole moment (C—F), and to have very low water interference. This may suggest that it would be desirable to have some form of polar entity involved in the stationary phase, but with low hydrogen bonding capability in order to reduce the interference from moisture.

An analysis may involve the dynamic models of analytes diffusing across a stationary phase surface. These models may be done to determine whether separation and relative retention time could be qualitatively determined using molecular modeling. In order to simulate separation using a surface of the stationary phase, the analytes may be first randomly oriented in a cell volume, and the relative orientations may be miniminzed. This may represent the initial analyte mixture. The analyte mixture may then be introduced onto one end of a simulated surface and the mass may be minimized with the surface. The analytes may then be given an initial forcing potential to start the movement along the surface and the simulation be continued for up to 5 ps depending upon the mixture. The simulations may be repeated at least twice to be sure of the elution order, and all positions may be averaged for the final comparisons. Although more statistics might be determined from the multiple simulations, one may concentrate on the averaged results. It appears from these trajectories, that the effect surface interaction may be attained in these simulations due to the separation of the analytes found.

Figure 35:
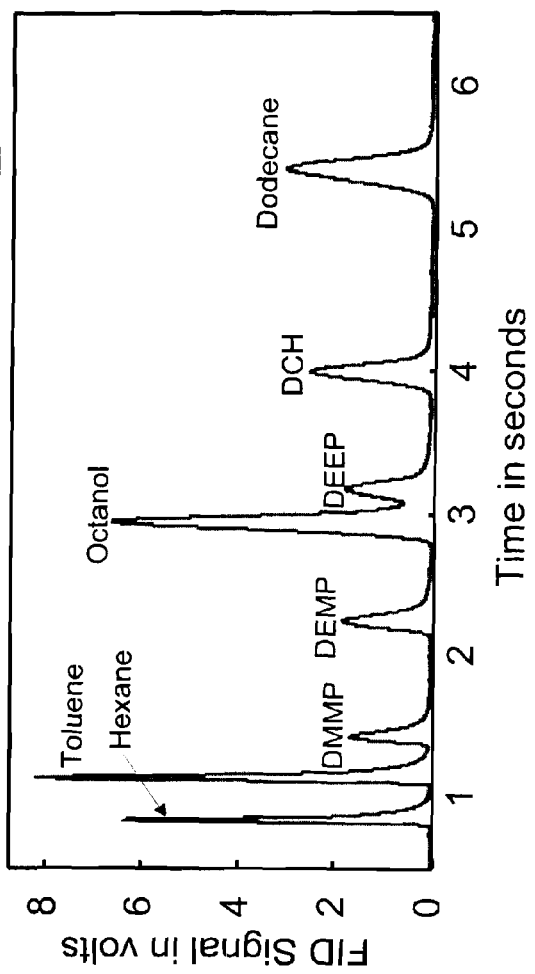
FIG. 35 shows an experimental GC analysis of a several compound mixture showing relative retention orders on a silicone stationary phase.
Figure 36:
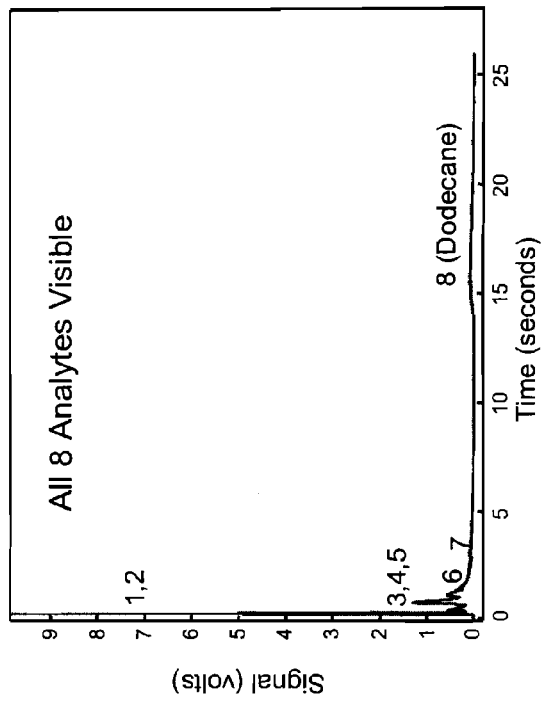
FIG. 36 shows an experimental gas chromatography (GC) separation of a several component mixture on a GC chip using a carbon nanotube stationary phase.

FIGS. 35-36 show experimental GC results on capillary-deposited (DB-5) and chip-deposited (carbon nanotube) stationary phases, respectively. FIGS. 35-36 show an experimental chromatograms using a silicone stationary phase to compare the relative elution orders found in the simulations. From the results, hexane is expected to elute first and dodecane is expected to elute last. It also appears that the carbon nanotube surface is more difficult to elute.

Figure 37:
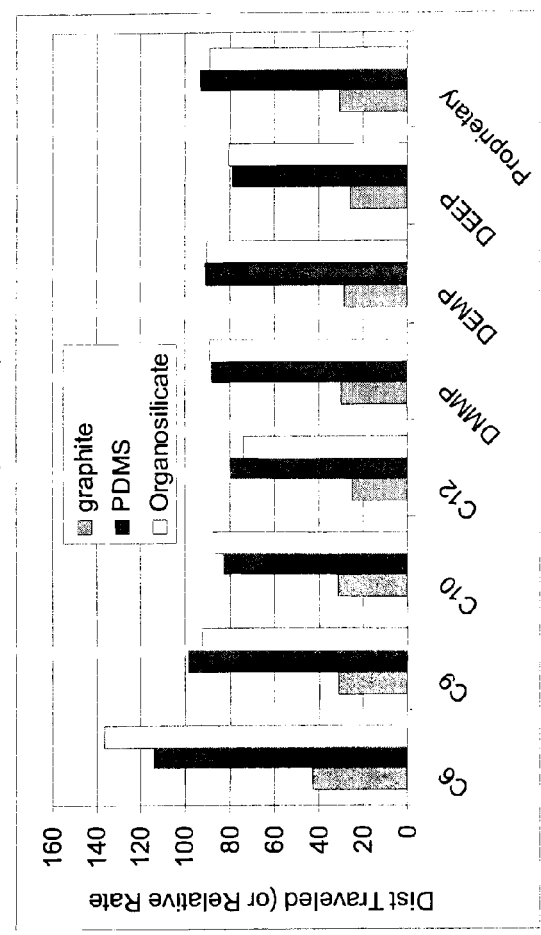
FIG. 37 shows a relative averaged elution order expected from the three stationary phases simulated, graphite, PDMS and organosilicate.
Figure 38:
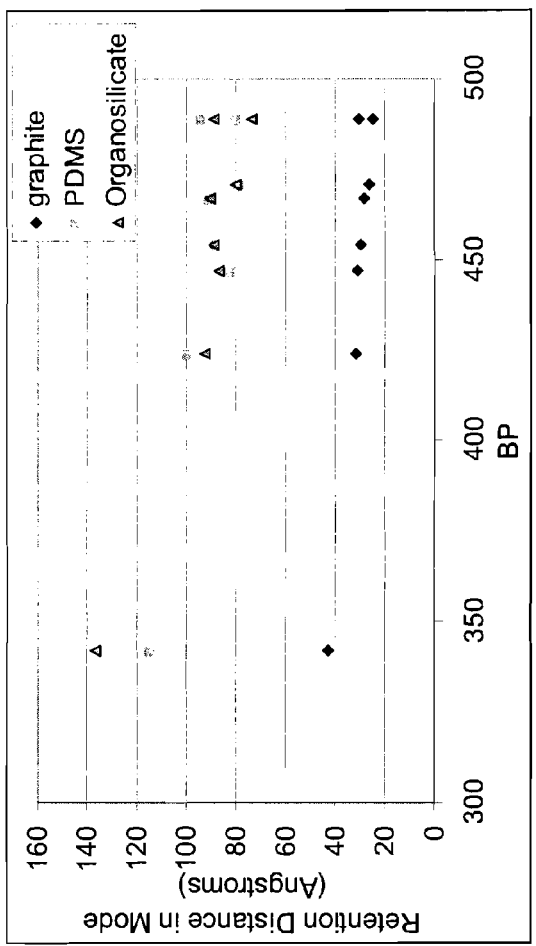
FIG. 38 shows retention versus boiling points of analytes on different stationary phases.

The dynamic simulation results are shown in FIGS. 37-42. For instance, FIG. 37 shows a relative averaged elution order expected from the three stationary phases simulated, graphite, PDMS and organosilicate. It may be found that the graphite surface is the most retentive having the lowest travel of the analytes. This may be supported with trials with carbon nanotubes, and may be especially apparent when comparing experimental GC results of a silicone stationary phase versus carbon nanotubes (FIGS. 35-36). The organosilicates and PDMS may be found to be similar in performance. As indicated in FIG. 38, the three stationary phases may separate the molecules roughly according to their relative volatility (boiling points). This may also be expected by analysis of the relative adsorption energies.

FIG. 35 shows an experimental GC analysis of an eight compound mixture showing relative retention orders on a silicone stationary phase, capillary 100 cm/100 μm, 400 thick nm-DB5, 100 degrees C. This information may be from Rob Synovec of the University of Washington. FIG. 36 shows an experimental GC separation of the eight component mixture on a GC chip using a carbon nanotube (CNT) stationary phase 125 degrees C., 50 cm length capillary, and H2/30 psi. This information may be from Rob Synovec of the University of Washington. FIG. 37 shows results of averaged retention times on three different stationary phases showing a high relative retention ability of the graphitic surface. FIG. 38 shows retention versus boiling points of analytes on the different stationary phases.

Figure 39:
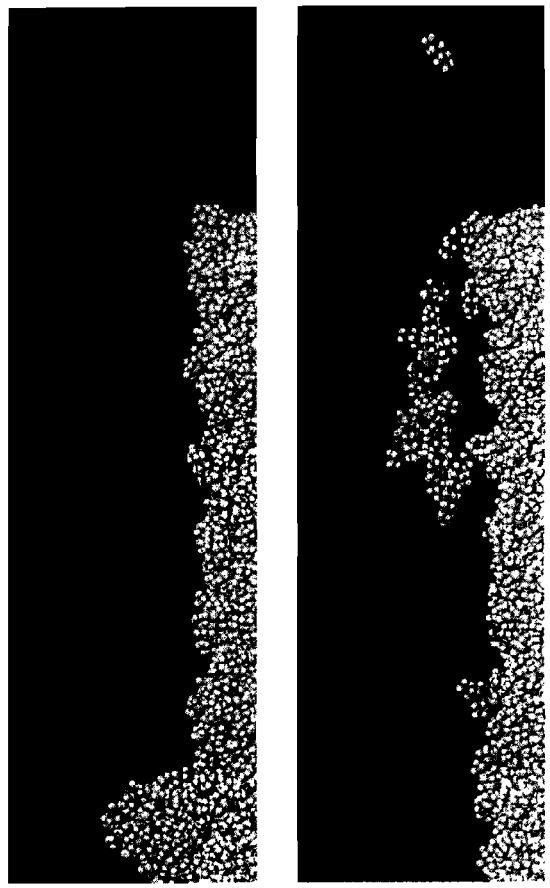
FIG. 39 shows separation simulations on PDMS.
Figure 40:
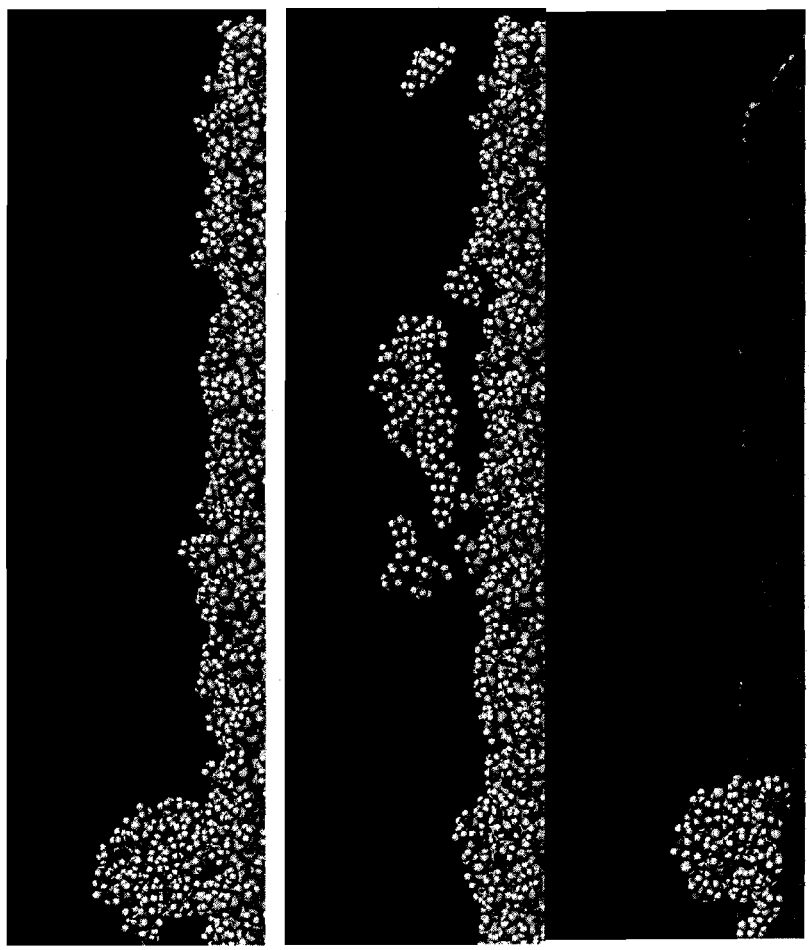
FIG. 40 shows a mixture eluting on an organosilicate.
Figure 41:
FIG. 41 shows the elution simulation on a graphite surface.

As might be appreciated in simulation trajectory results (FIGS. 39-41), molecular models may be be run on a sufficiently small scale to reveal the actual separation dynamics. FIG. 39 shows separation simulations on PDMS. After separation, hexane appears to be eluting first (at the far right of the bottom figure in FIG. 39). The DEEP phosphonate and docecane appears to be the slowest to elute. FIG. 40 shows the same mixture eluting on an organosilicate. In general, the mixtures appear to be eluting similiarly to the PDMS. However, FIG. 41 shows the elution simulation on a graphite surface (to simulate a carbon nanotube surface). There appears to be very little movement of this mixture down the surface of the graphite; however, clearly dodecane appears to be left behind and elute very slowly. When looking for elution distance of the analytes, there may be some separation and re-positioning occuring within the traveling mass over the course of the simulation. This seems to suggest that given a long enough path, analyte separation should become resolved.

The elution order on PDMS (from FIG. 39) may also be compared to the experimental elution order found on DB5 (from FIG. 35), which may be a slightly phenylated PDMS silicone and close to the PDMS structure. This comparison is found in FIG. 42, which shows that relative elution order may be almost the same for both simulation and experimental differing only in DMMP and DEMP order. In general, this may be enough to show that the molecular models can give approximated retention order; but as may be appreciated by the center masses of analytes found in the center of the three examples (FIG. 39-41), better separation should be achieved to reasonably expect a good prediction of actual separation. Actual order in the simulation might be expected to improve as the models are scaled to bigger surfaces, higher pathlengths and slower simulation speeds in order to better reflect surface to analyte interaction and higher realism in speeds.

These models appear to show that on a molecular level, separation may be started from a fundamental level. So retention may begin in the molecular forces derived from the adsorption, and may continue with the dynamic interaction with the surface. Using different mixes, it appears that in general the amount of separation and the extent of retention may depend upon the content of the mixture.

Figure 42:
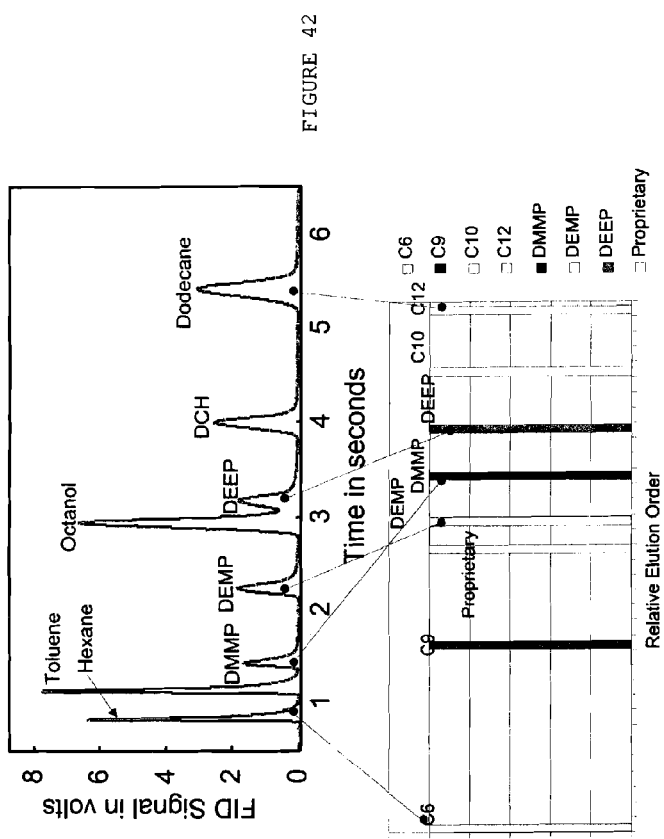
FIG. 42 shows a relative elution order which may be nearly the same for both simulation and experiment.

FIG. 39 shows before (top) and after (bottom) snapshots of a separation dynamic simulation of a mixture of hexane, nonane, decane, dodecane, DMMP, DEMP and DEEP on PDMS showing separation. FIG. 40 shows before (top) and after (bottom) snapshots of the same mixture as FIG. 36, using an organosilicate stationary phase layer. FIG. 41 shows before (top) and after (bottom) snapshots of the same mixture as FIG. 36, using a graphite stationary phase layer. FIG. 42 shows an elution order from the experimental (FIG. 35) contrasted to the molecular model order (FIG. 39).

Figure 43:
FIG. 43 shows examples of a residue on different organosilicates where phosphonates have found stabilization within depressions of a surface.

Another facet of these simulations is that in addition to their use in predicting the relative elution order, the simulations appeared to indicate which stationary phases were more prone to residuals left at the origin, and which would foul a column if not baked out. This is a phenonomenon which may be observed with various PHASED tests, which may be rectified by a bake/clean cycle before injection of the next test. For the organosilicate, DEEP or DMMP may be found to be one material likely to be left as a residue, but this may depend upon the initial analyte mixture. For the PDMS, DMMP appeared be found buried in a molecular depression. These hints at column fouling may be an additional advantage of the usefulness of the molecular simulation. Residue is apparent in FIGS. 39-41, but FIG. 43 shows examples of the residue on different organosilicates where the phosphonates (solid gray-scale) have found stabilization within depressions of the surface of an organosilicate. FIG. 43 shows an example of material left at an origin during a simulation due to extra stabilization with the surface as evidence of possible residue, with DEEP (left) and DMMP (right). The stationary phase may be an organosilicate.

In order to explore the effect of hydration and SiOH content for silicon-containing stationary phases, separation of DMMP, dodecane and hexane may be compared on an organosilicate stationary phase. The results appear to be reflected in FIGS. 44-45, and may show that the quality of separation of DMMP from the alkanes is affected by water and SiOH as is expected from the adsorption data noted hereinin (FIGS. 30-31) but not necessarily to the extent expected from the thermodynamic calculations alone.

Figure 45:
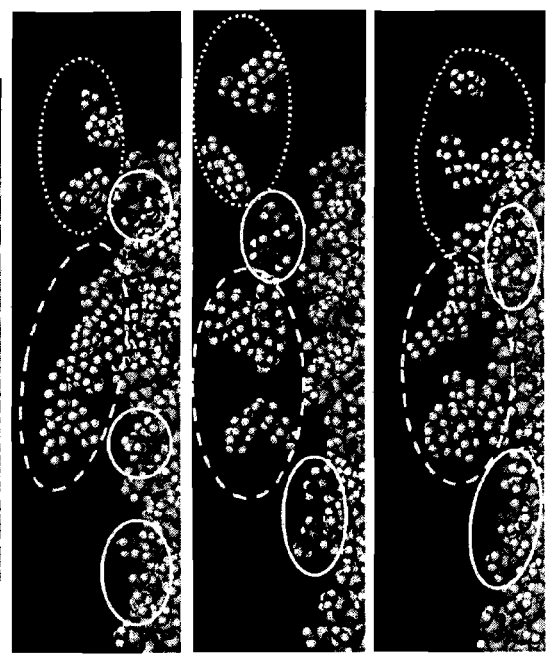
FIG. 45 shows configurations revealing an effect of OH on a silicate stationary phase.

Two effects seem apparent when comparing the simulations. There may be a large amount of DMMP residue left at the starting point (solid circles on the far left), and hexane appears to be eluting first (dotted circles on the far right). When comparing the original silicate structure (top) with the hydrated (middle) and extra silanol case (bottom), the biggest effect on the analyte appears to be for DMMP, and a larger overall movement of DMMP appears to occur when the surface is hydrated (FIG. 45 middle). In this case, half of the DMMP may be moving before dodecane, whereas in the other two cases, most of the DMMP appears to be lagging behind the dodecane. Interestingly, the dynamic trends appear to agree more with the boiling point expectations (hexane BP=342; DMMP BP=454K, dodecane BP=489) than the adsorption thermodynamic trends (FIG. 31) where hexane may be expected to elute, and may appear especially noticable when comparing the hexane energy trends with the dynamic trends of FIG. 45.

Figure 44:
FIG. 44 shows configurations revealing an effect of OH on a silicate stationary phase separating a hexane and dodecane mixture using several molecules of each analyte.

FIG. 44 shows starting configurations revealing an effect of OH on a silicate stationary phase separating hexane and dodecane mixture using four molecules of each analyte. Top portion of the Figure shows silicate with minimal SiOH content. The middle portion shows the same as top, but with a hydrated surface. The bottom portion shows the same as top, but with an increased SiOH surface content.

FIG. 45 shows end configurations revealing an effect of OH on a silicate stationary phase separating DMMP, hexane and dodecane mixture, with solid circles indicating the DMMP location, the dashed circles indicating the dodecane location, and the dotted circles indicating the decane location. The top portion of FIG. 45 shows silicate with minimal SiOH content; the middle portion is the same as the top portion, but with a hydrated surface; and the bottom portion is the same as the top portion, but with an increased SiOH surface content.

For simulation trends, in virtually all cases, hexane is expected to elute first (all hexane is at far right at the flow front); however, the thermodynamic energies suggest that the hexane preference may change depending upon hydration state and silanol content. In experimental cases, hexane may also be known to elute well ahead of the other analytes used in a simulation. The dynamic simulations may also suggest that depending upon conditions, DMMP may elute in a peak that is wide and disperse, rather than in a tight peak as may be suggested by the less disperse and more collective hexane grouping. These grouping qualities may demonstrate a potential usefulness of molecular dynamics in understanding peak separation and resolution. By contrast, the thermodynamic trends alone may distinguish the quality of the separation without transformation through experimental observations like the Golay equation. For a virtually pure simulation, it may be the most useful to predict the experimental differences in separation without imposing an additional mathematical construct.

The differences between the two different molecular modeling analyses might be anticipated, if one considers that the dynamic simulation may attempt to approximate the more kinetic condition of analyte flow and dispersive separation rather than the static equilibrium condition reflected in the thermodynamic energies. Because the dynamic condition should be considered to gauge separation, dynamic simulations may be expected to produce better snapshots of the interactions than simple thermodynamics. Again, as with the previous dynamics, the separation predictability of the simulation may be expected to increase with an increase in scale and a lowering of the dynamics speeds of the simulation toward a more realistic simulation. However, enough approximate trends may be present in the dynamics to help in understanding formulation of the stationary phase.

The molecular modeling study appears to confirm that one may model surface issues associated with a working MEMS-GC. The molecular models appear to show how both enthalpy and free energy trends signal differences between stationary phase performances. In addition, dynamic models of relative retention time on the stationary phases appear to show how the molecules may interact with the specific surface to bring about separation. Given adequate scaling, the peak dispersion might be derived from the statistics of separation.

The thermodynamics and the dynamics of the stationary phase-analyte interaction may be explored using simple molecular modeling techniques to understand basic molecular influences on the GC performance. The question of matching the best surface functionalization to the base stationary phase may be approached via molecular modeling to provide information on the activity of the device's surfaces. For example, as may be appreciated by the description of the material concerns, hydration and polarity issues should be important to the design of the stationary phase. It appears that certain kinds of materials are more heavily affected. In addition, because the molecular model appears not to be limited to the types of base materials that are commercially available, it may be used to explore not only existing and but new materials without constraint.

The modeling described herein appears to represent methods that may serve to screen materials for adsorption tendencies for not only GC-MEMS devices, but may also be used for the identification of surface properties in other applications. For instance, the issue of contaminant migration in IC manufacture may be a key concern, especially as surface dependent processes such as ALD come into fashion. And, as may be envisioned for a multi-function and multi-material device, many material design issues may be addressed using molecular modeling. For example, other future materials issues that can be addressed for the MEMS-GC may be layer adhesion and package reliability.

An example of MGA or GC for which the materials may be utilized is described here for illustrative purposes. A fluid composition sensor, analyzer or chromatograph may have a concentrator, separator, various detectors and a pump. The concentrator may have an array of phased heaters that are turned on at different times relative to each other in a fluid stream channel. It may relate to a phased heater array structure, and more particularly to application of the structure as a sensor, analyzer or chromatograph for the identification and quantification of fluid components. Such apparatus having such heater configuration may be regarded as or referred to as a "PHASED" device. The term "PHASED" also may be regarded as an acronym referring to "Phased Heater Array Structure for Enhanced Detection". The term "fluid" may be a generic term that includes gases and liquids as species.

Some advantages of the present micro fluid analyzer modular structure over other structures may include an ability to operate in a changing temperature environment (i.e., ability to compensate for changing sensitivity of each individual detector) with automatic rather than manual compensation for such changes, and the ability to operate without moving parts, resulting without measurable ripple ($\leq 1$ percent) on the suction side.

The device may be a sensor system/micro analyzer consisting of an array of selective, sensitive, fast and low-power phased heater elements in conjunction with an array of compact, fast, low-power, ambient pressure, minimal pumping mass spectral analysis devices to achieve fluid component presence, identification and quantification. The device may be very small, energy-efficient and portable including its own power source.

The micro fluid analyzer may have one or more concentrators and two or more separators. The analyzer may have one, two or more pumps. The analyzer may have a pre-concentrator having a number of channels. There may be numerous detectors positioned along the flow path of the analyzer. Also, one or more orifices and micro valves may be positioned in the flow path. The concentrator may have an array of phased heater elements that provide a heat pulse to generate- a desorbed-analyte concentration pulse that moves along the fluid path to provide an increasing concentration of analytes. The analyzer may be configured as a multiple fluid or gas chromatograph.

A micro fluid analyzer may incorporate a phased heater array, concentrator, separator and diverse approaches. The micro fluid analyzer may be a low-cost approach to sense ozone with a several parts-per-billion (ppb) maximum emission objective. The analyzer may be capable of detecting a mixture of trace compounds in a host or base sample gas or of trace compounds in a host liquid.

The fluid analyzer may include a connection to an associated microcontroller or processor. An application of the sensor may include the detection and analyses of air pollutants in aircraft space such as aldehydes, butyric acid, toluene, hexane, and the like, besides the conventional $CO_2$, $H_2O$ and CO. Other sensing may include conditioned indoor space for levels of gases such as $CO_2$, $H_2O$, aldehydes, hydrocarbons and alcohols, and sensing outdoor space and process streams of industries such as in chemical, refining, product purity, food, paper, metal, glass, medical and pharmaceutical industries. Also, sensing may have a significant place in environmental assurance and protection. Sensing may provide defensive security in and outside of facilities by early detection of chemicals before their concentrations increase and become harmful.

The sensor has high sensitivity. The sensor offers sub-ppm or sub-ppb level detection which is 100 to more than 10,000 times better than related art technology, such as conventional gas chromatographs which may offer a sensitivity in a 1 to 10 ppm range. The sensor is, among other things, a lower-power, faster, and more compact, more sensitive and affordable version of a gas chromatograph. It may have structural integrity and have very low or no risk of leakage in the application of detecting and analyzing pressurized fluid samples over a very large differential pressure range.

The pump of the sensor may be arranged to draw sample gas through a filter in such a way as to provide both fast sample acquisition and regulated flow through the phased heater sensor. As a pump draws sample gas through the sensor, the gas may expand and thus increase its volume and linear velocity. The control circuit may be designed to compensate for this change in velocity to keep the heater "wave" in sync with the varying gas velocity in the sensor. To compensate for the change in sample gas volume as it is forced through the heater channels, its electronics may need to adjust either the flow control and/or the heater "wave" speed to keep the internal gas flow velocity in sync with the electric-driven heater "wave".

The sensor may have the sensitivity, speed, portability and low power that make the sensor especially well suited for safety-mandated periodic leak surveys of natural gas or propane gas along transmission or distribution pipeline systems and other gas in chemical process plants.

The sensor may in its leak sensing application use some or all sample gas constituents (and their peak ratios) as calibration markers (elution time identifies the nature of the gas constituents) and/or as leak source identifiers. If the presence alone of a certain peak such as methane (which is present in mountain air at about one to two ppm) may not be enough information to indicate that the source of that constituent is from swamp gas, a natural or pipeline gas or another fluid.

The sensor may be used as a portable device or installed at a fixed location. In contrast to comparable related art sensors, it may be more compact than a portable flame ionization detector without requiring the bulkiness of hydrogen tanks, it may be faster and more sensitive than hot-filament or metal oxide combustible gas sensors, and much faster, more compact and more power-thrifty than conventional and/or portable gas chromatographs.

FIG. 5 reveals certain details of an illustrative example of a micro gas apparatus (MGA) 15. The specifications and structural details are illustrative but may be different for similar MGA's. Various structures of an MGA may be implemented for illustrative purposes of the invention. Sample stream 25 may enter input port 34 from pipe or tube 19. There may be a particle filter 43 for removing dirt and other particles from the stream of fluid 25 that is to enter apparatus 15. This removal is for the protection of the apparatus and the filtering should not reduce the apparatus' ability to accurately analyze the composition of fluid 25. Dirty fluid (with suspended solid or liquid non-volatile particles) might impair proper sensor function. A portion 45 of fluid 25 may flow through the first leg of a differential thermal-conductivity detector (TCD), or chemi-sensor (CRD), or photo-ionization sensor/detector (PID), or other device) 127 which may measure photo-ionization current, and a portion 47 of fluid 25 flows through tube 49 to a pump 51. By placing a "T" tube immediately adjacent to the inlet 45, sampling with minimal time delay may be achieved because of the relatively higher flow 47 to help shorten the filter purge time. Pump 51 may cause fluid 47 to flow from the output of particle filter 43 through tube 49 and exit from pump 51. Pump 53 may effect a flow of fluid 45 through the sensor via tube 57. There may be additional or fewer pumps, and various tube or plumbing arrangements or configurations for system 15 in FIG. 46. Data from detectors 127 and 128 may be sent to control 130, which in turn may relay data to microcontroller and/or processor 29 for processing. Resultant information may be sent to station 31.

Figure 46:
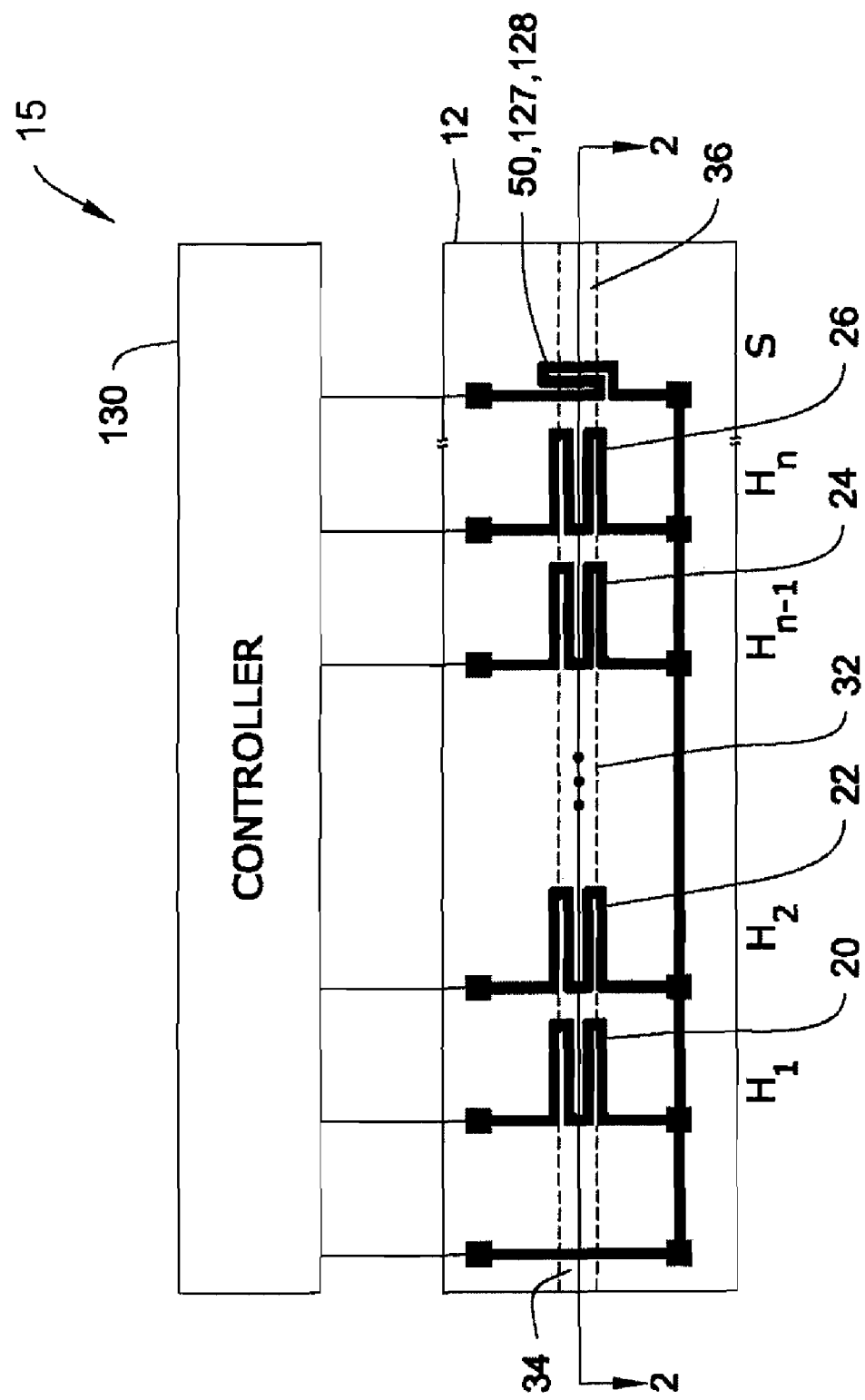
FIG. 46 is a diagram of part of a fluid analyzer representing a portion of a concentrator or separator.
Figure 47:
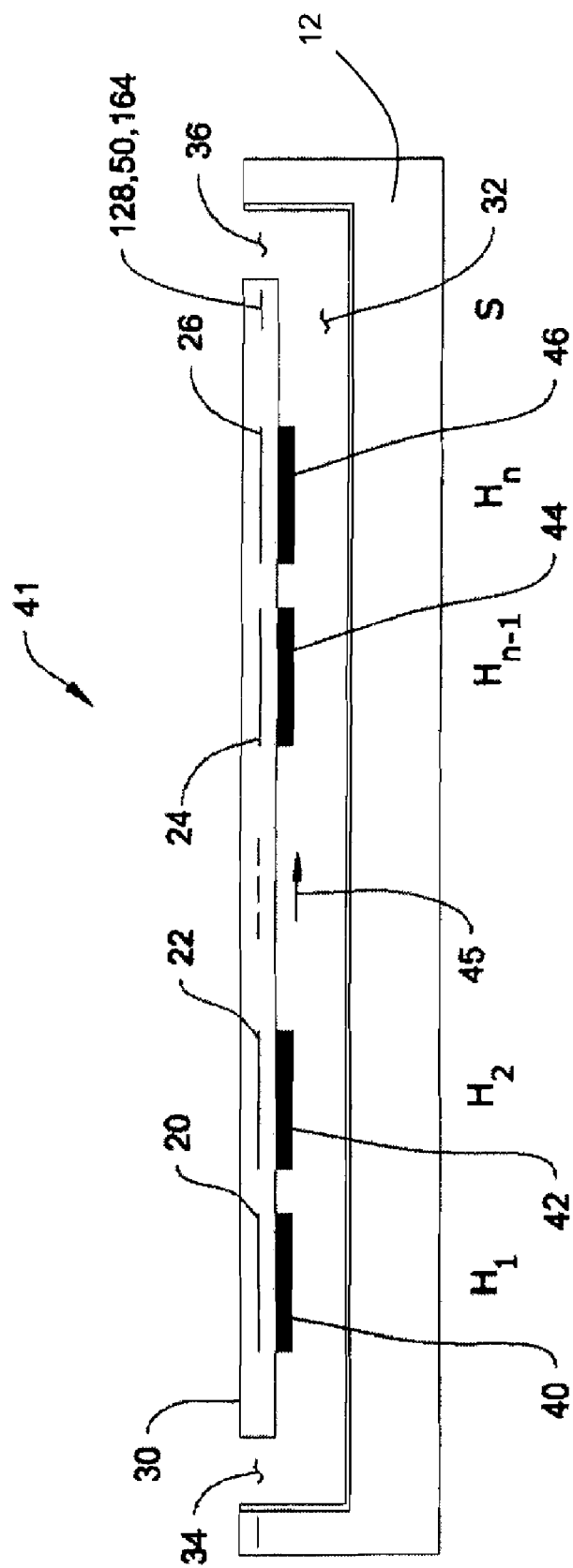
FIG. 47 is a length-wise sectional view of heater elements on a channel.

FIG. 46 is a schematic diagram of part of the sensor apparatus 15, representing a portion of concentrator 124 or separator 126 in FIG. 5. The sensor apparatus may include a substrate 12 and a controller 130. Controller 130 may or may not be incorporated into substrate 12. Substrate 12 may have a number of thin film heater elements 20, 22, 24, and 26 positioned thereon. While only four heater elements are shown, any number of heater elements may be provided, for instance, between two and one thousand, but typically in the 20-100 range. Heater elements 20, 22, 24, and 26 may be fabricated of any suitable electrical conductor, stable metal, or alloy film, such as a nickel-iron alloy sometimes referred to as permalloy having a composition of eighty percent nickel and twenty percent iron; platinum, platinum silicide and polysilicon. Heater elements 20, 22, 24, and 26 may be provided on a thin, low-thermal mass, low-in-plane thermal conduction, support member 30, as shown in FIG. 47. Support member or membrane 30 may be made from $Si_3N_4$ or other appropriate or like material. The heater elements may be made from Pt or other appropriate or like material.

Substrate 12 may have a well-defined single-channel phased heater mechanism 41 having a channel 32 for receiving the sample fluid stream 45, as shown in FIG. 47. The channel may be fabricated by selectively etching silicon channel wafer substrate 12 beneath support member 30. The channel may include an entry port 34 and an exhaust port 36.

The sensor apparatus may also include a number of interactive elements inside channel 31 so that they are exposed to the streaming sample fluid 45. Each of the interactive elements may be positioned adjacent, i.e., for closest possible contact, to a corresponding heater element. For example, in FIG. 47, interactive elements 40, 42, 44, and 46 may be provided on the lower surface of support member 30 in channel 32, and be adjacent to heater elements 20, 22, 24, and 26, respectively. There may be other channels with additional interactive film elements which are not shown in the present illustrative example. The interactive elements may be formed from any number of films commonly used in liquid or gas chromatography, such as silica gel, polymethylsiloxane, polydimethylsiloxane, polyethyleneglycol, porous silica, Nanoglass™, active carbon, and other polymeric substances. Furthermore, the above interactive substances may be modified by suitable dopants to achieve varying degrees of polarity and/or hydrophobicity, to achieve optimal adsorption and/or separation of targeted analytes.

FIG. 6 shows a cross-section end view of a one-channel phased heater mechanism 41. An end view of a single channel phased heater mechanism 41 may incorporate the support member 30 and substrate 12 and the items between them. FIG. 6 shows a version of the phased heater mechanism 41 having an exposed 1 micron membrane. Also shown is open space 392. Support member 30 may be attached to top structure 65. Anchors 67 may hold support member 30 in place relative to channel 32. Fewer anchor 67 points minimize heat conduction losses from support 30 to other portions of structure 41. There may be a heater membrane that has a small number anchor points for little heat conduction from the heater elements.

The heater elements of a phased heater array may be coated with an adsorber material on both surfaces, i.e., top and bottom sides, for less power dissipation and more efficient heating of the incoming detected gas. The heater elements may have small widths for reduced power dissipation.

Interactive film elements may be formed by passing a stream of material carrying the desired sorbent material through channel 32 of heating mechanism 41. This may provide an interactive layer throughout the channel. If separate interactive elements 40, 42, 44, 46 are desired, the coating may be spin-coated onto substrate 30 attached to the bottom wafer 12, and then selectively "developed" by either using standard photoresist masking and patterning methods or by providing a temperature change to the coating, via heater elements 20, 22, 24 and 26.

The surfaces of inside channel of the heater array, except those surfaces intentionally by design coated with an adsorber material, may be coated with a non-adsorbing, thermal insulating layer. The thickness of the adsorber coating or film may be reduced thereby decreasing the time needed for adsorption and desorption. As in FIG. 6, coating 69 of a non-adsorbing, thermal insulating material may be applied to the inside walls of channel 32 in the single-channel heater 41, except where there is adsorber coated surfaces, by design, such as the interactive elements. The material should have thermal conduction that is substantially less than the material used in the channel walls. The latter may be silicon. Alternative materials for coating 69 may include $SiO_2$ or other metal oxides. Coating 69 may reduce power used for the heater elements in support 30. A minimizing or reduction of the size (width, length and thickness) of the heater element membranes as well as the adsorber film, while retaining a reasonable ratio of mobile/stationary phase volume, may result in about a significant power reduction. The minimized or reduced adsorber film thickness may reduce the time needed for adsorption-desorption and save energy needed per fluid analysis for a given analyzer structure.

Heater elements 20, 22, 24 and 26 may be GC-film-coated on both the top and bottom sides so that the width and power dissipation of the heater element surface is improved. The fabrication of these heater elements may involve two coating steps, with the second step requiring wafer-to-wafer bonding and coating after protecting the first coat inside the second wafer and dissolving the first wafer.

The micro gas analyzer may have heater elements 40, 42, . . . , 44, 46, fabricated via repeated, sequentially spin-coated (or other deposition means) steps, so that a pre-arranged pattern of concentrator and separator elements are coated with different adsorber materials A, B, C, . . . (known in GC literature as stationary phases), so that not only can the ratio of concentrator/separator elements be chosen, but also which of those coated with A, B, C and so forth may be chosen (and at what desorption temperature) to contribute to the concentration process and electronically be injected into the separator, where again a choice of element temperature ramping rates may be chosen for the A's to be different for the B, C, . . . elements; and furthermore adding versatility to this system in such a way that after separating the gases from the group of "A" elements; another set of gases may be separated from the group of "B" elements, and so forth. The ratio of concentrator to separator heater elements may be set or changed by a ratio control mechanism 490 connected to controller 130.

Controller 130 may be electrically connected to each of the heater elements 20, 22, 24, 26, and detector 50 as shown in FIG. 46. Controller 130 may energize heater elements 20, 22, 24, and 26 in a time phased sequence (see bottom of FIG. 48)

such that each of the corresponding interactive elements 40, 42, 44, and 46 become heated and desorb selected constituents into a streaming sample fluid 45 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 50, 128, for detection and analysis. Detector 50, 127, or 128 (FIGS. 5 and 46) may be a thermal-conductivity detector, discharge ionization detector, CRD, PID, MDD, or any other type of detector such as that typically used in gas or fluid chromatography.

Figure 48:
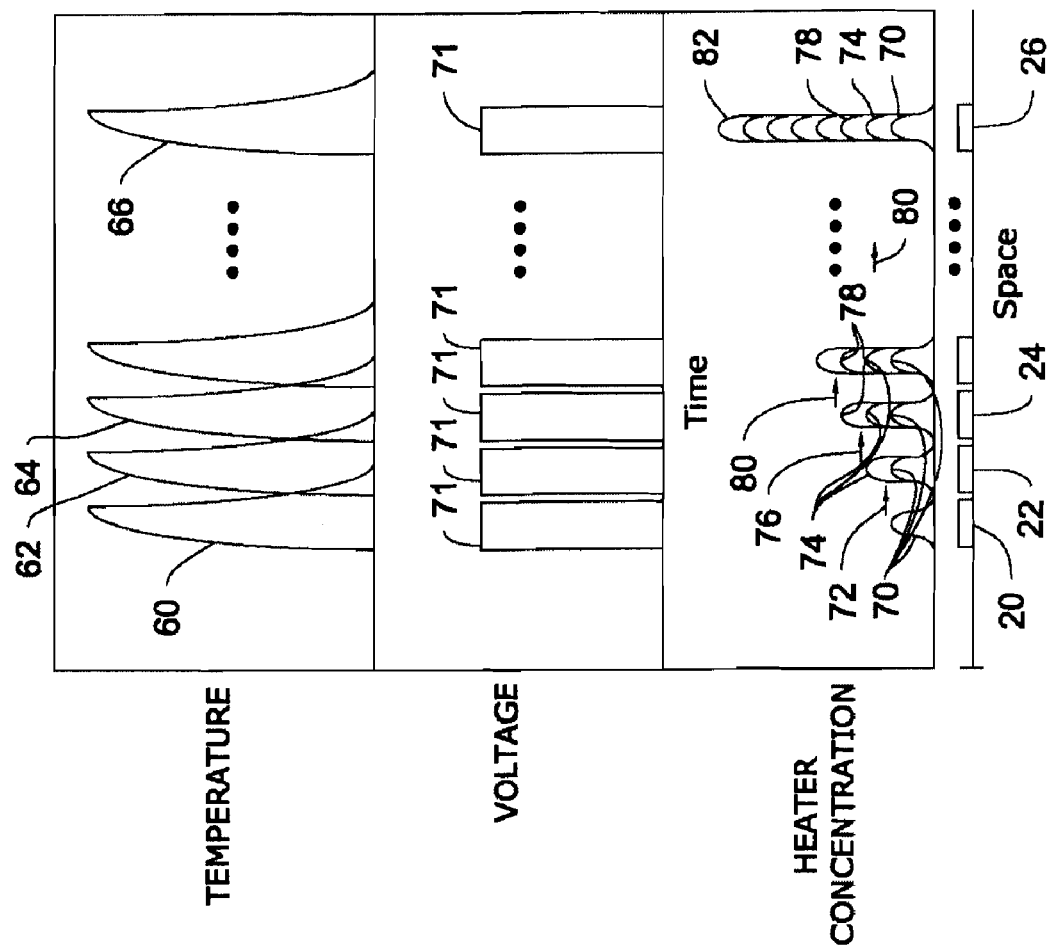
FIG. 48 is a graph illustrating heater temperature profiles, along with corresponding concentration pulses produced at each heater element of the sensor apparatus.
Figure 49:
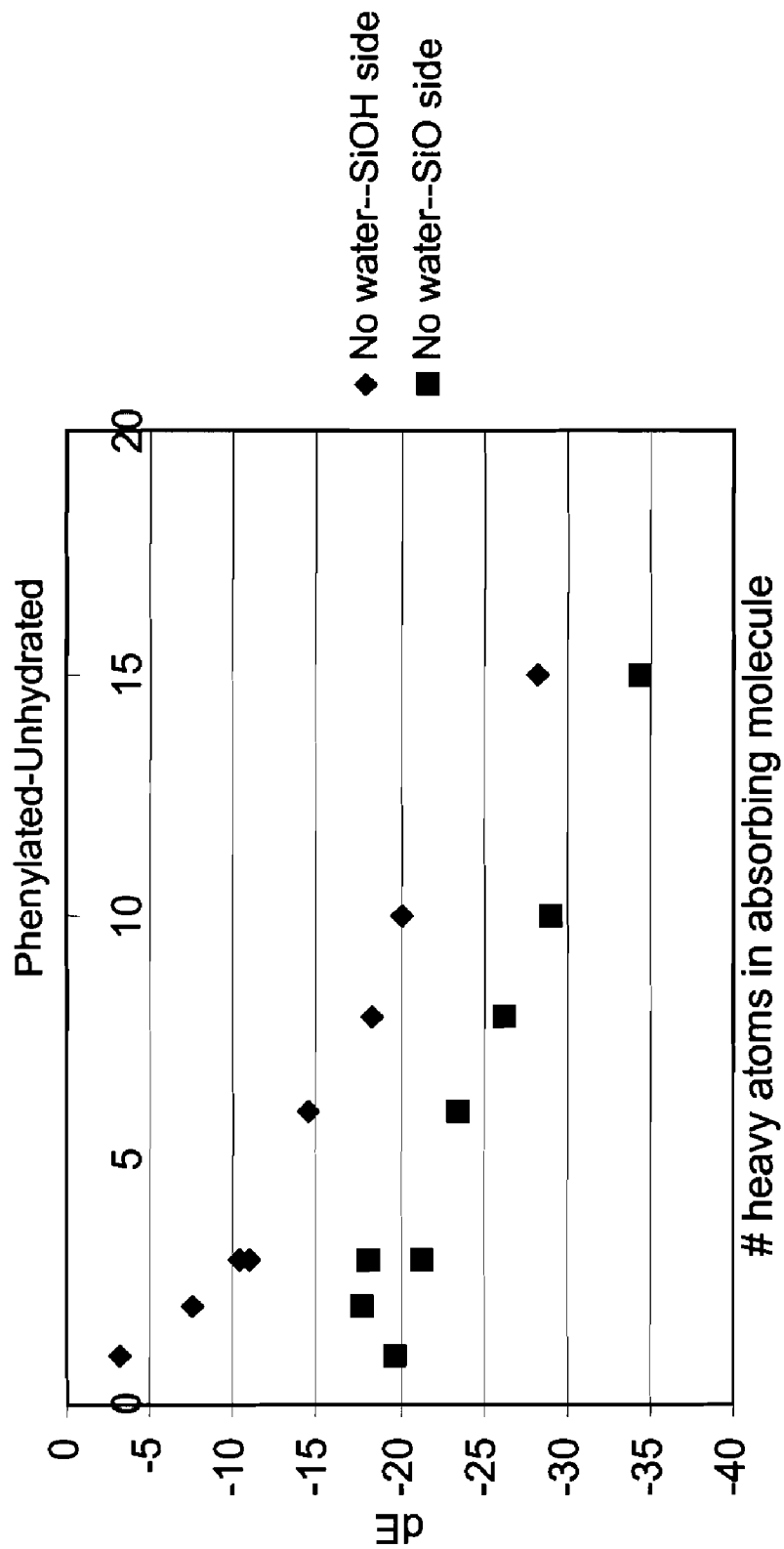
FIGS. 49-63 may relate to adsorption energies of phenylated silica-NG.
Figure 50:
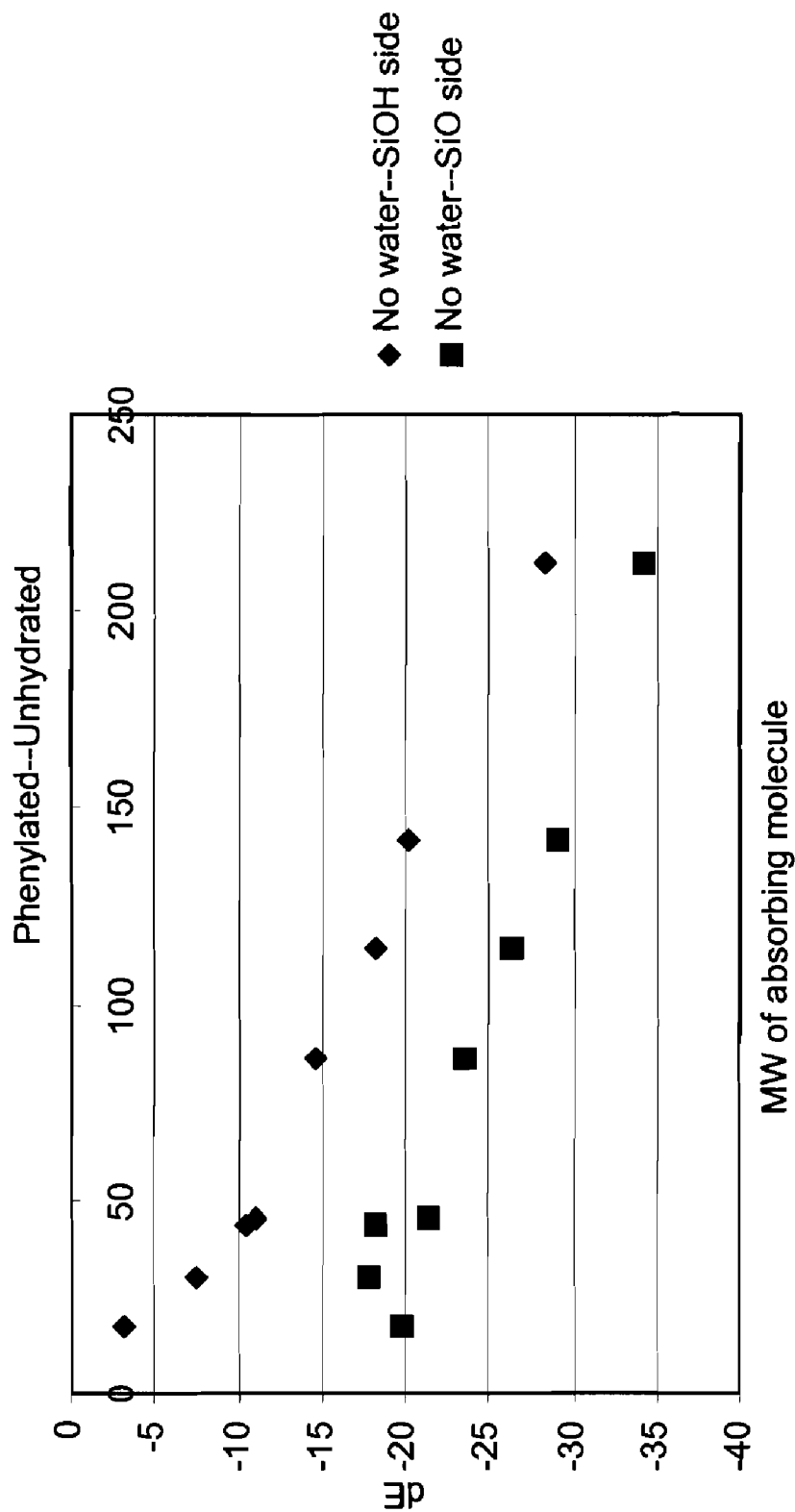
Figure 51:
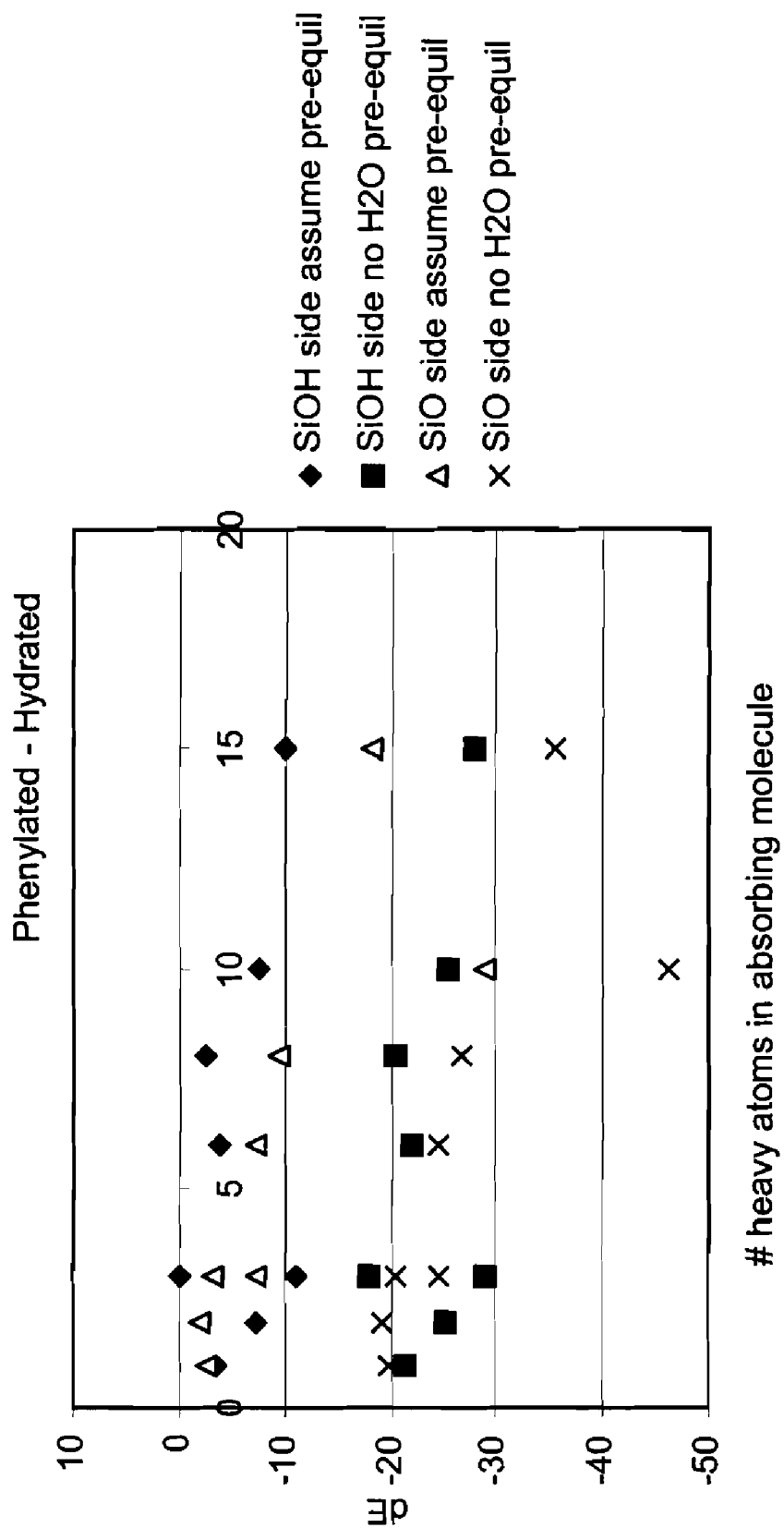
Figure 52:
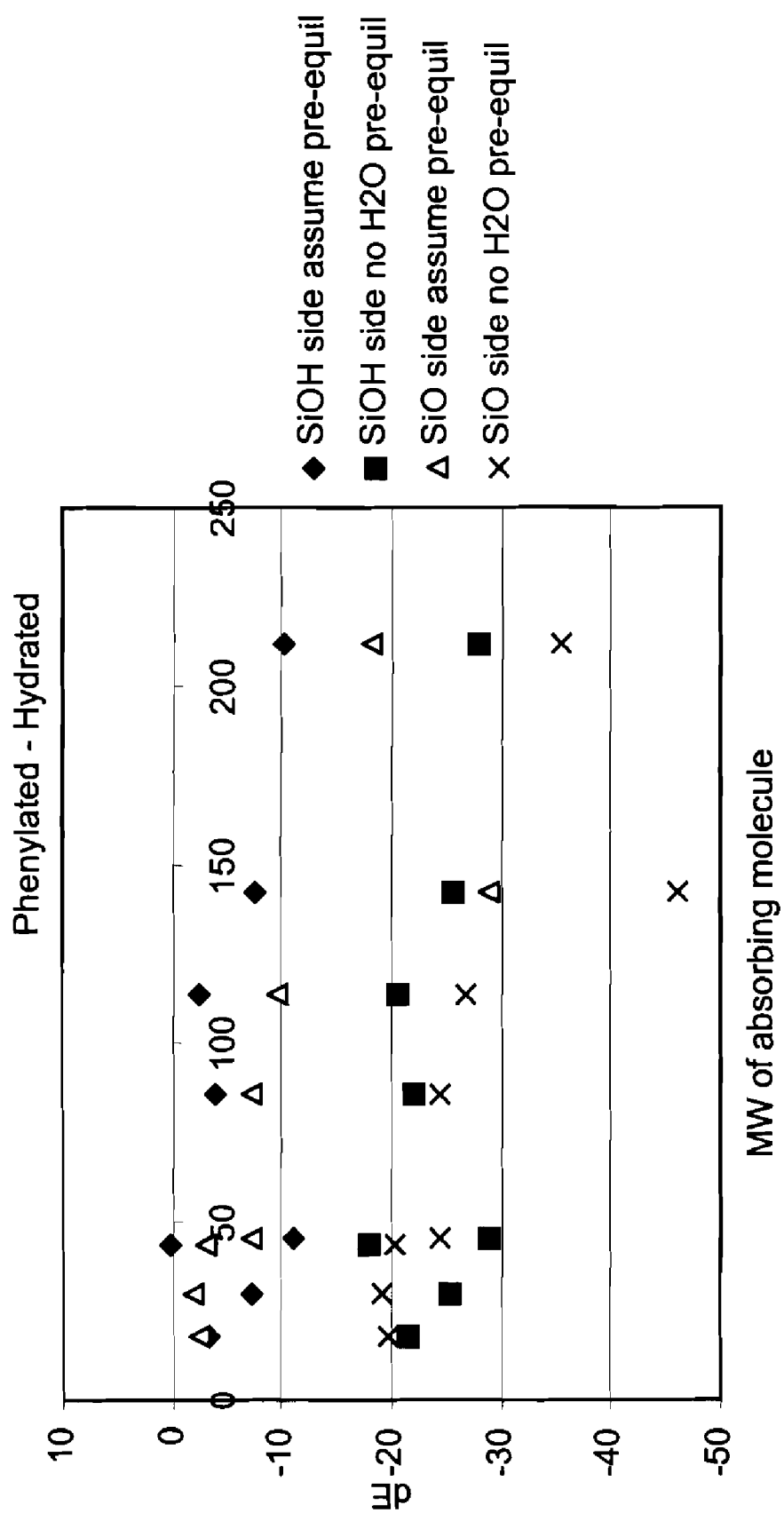
Figure 53:
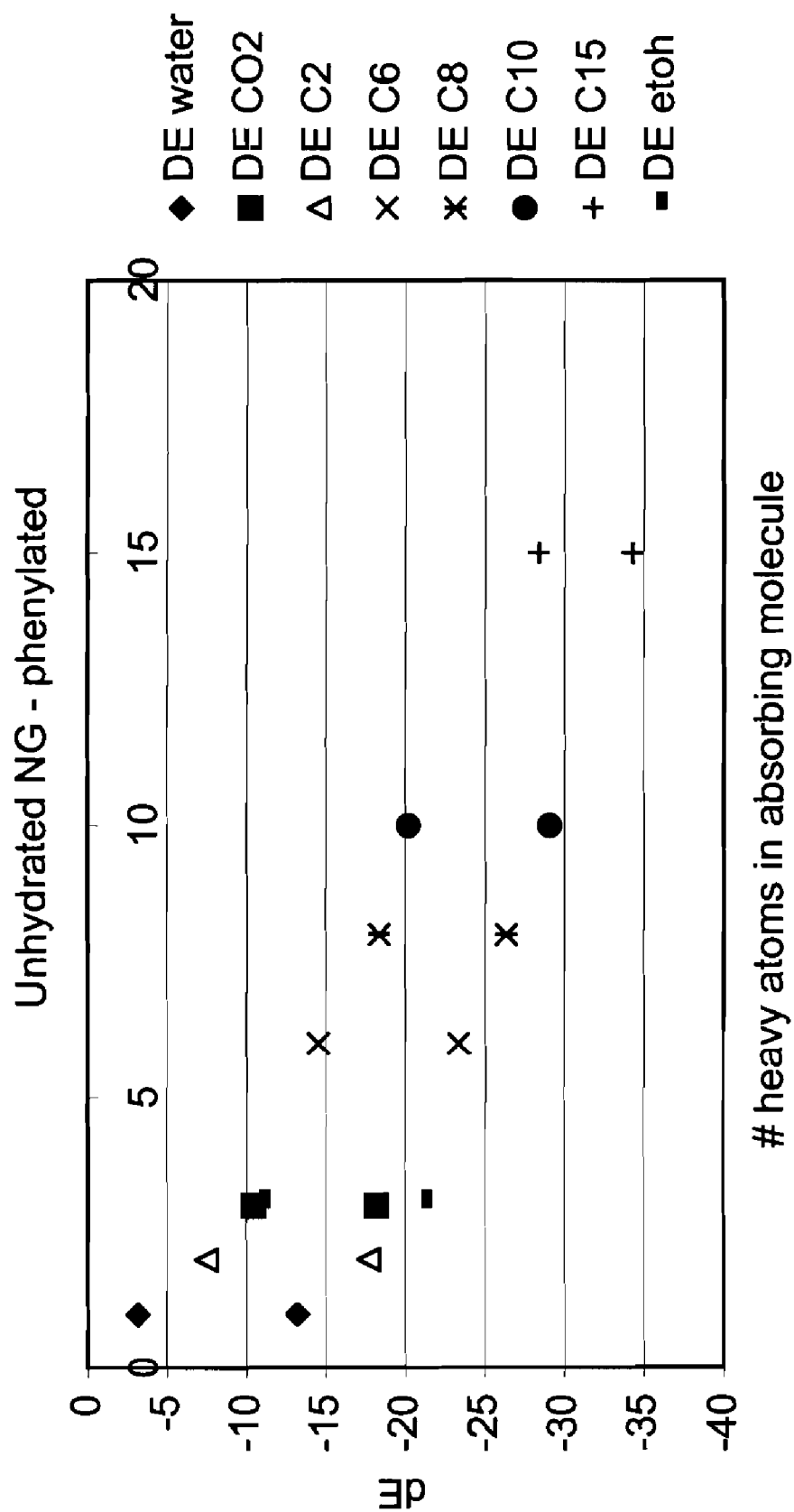
Figure 54:
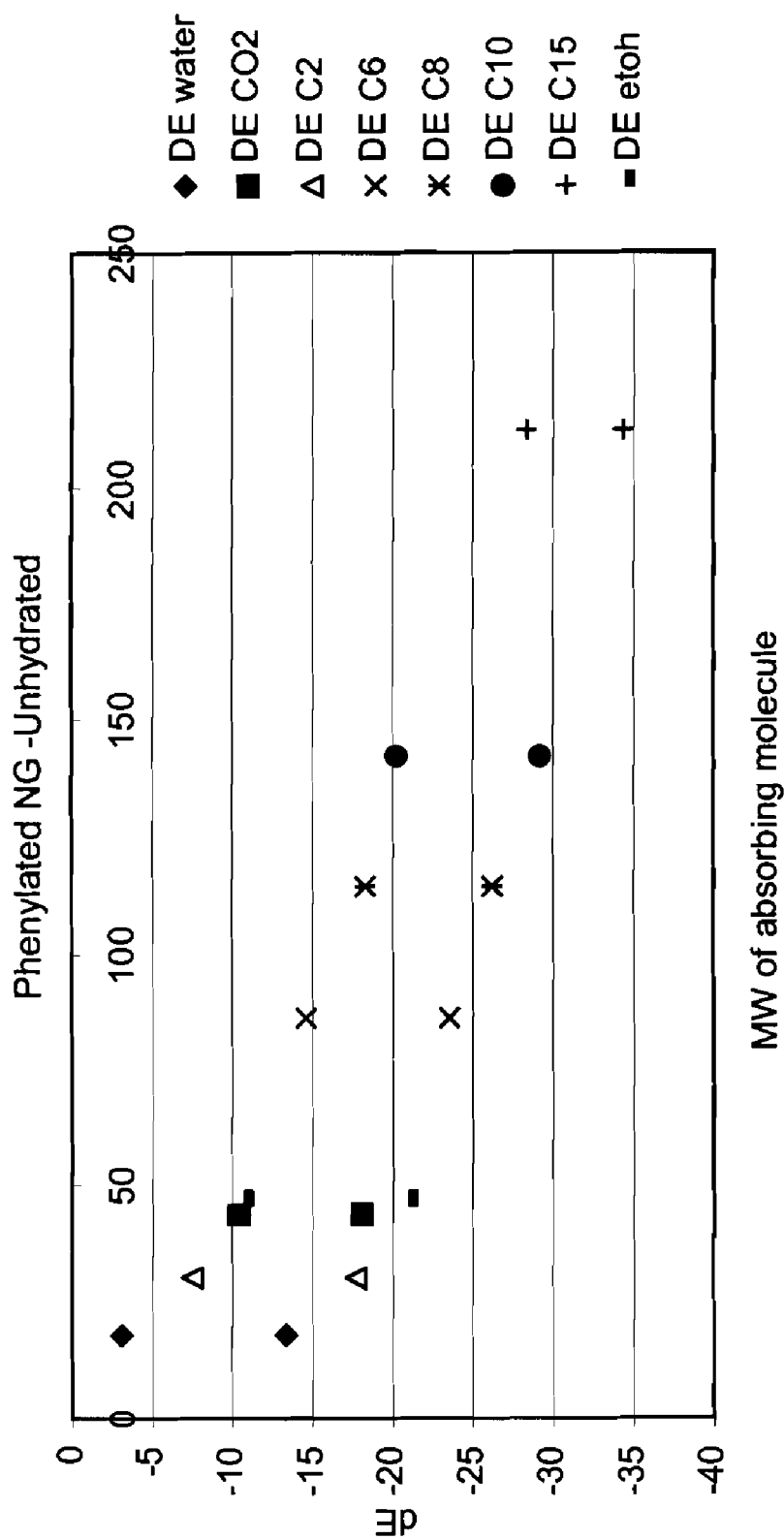
Figure 55:
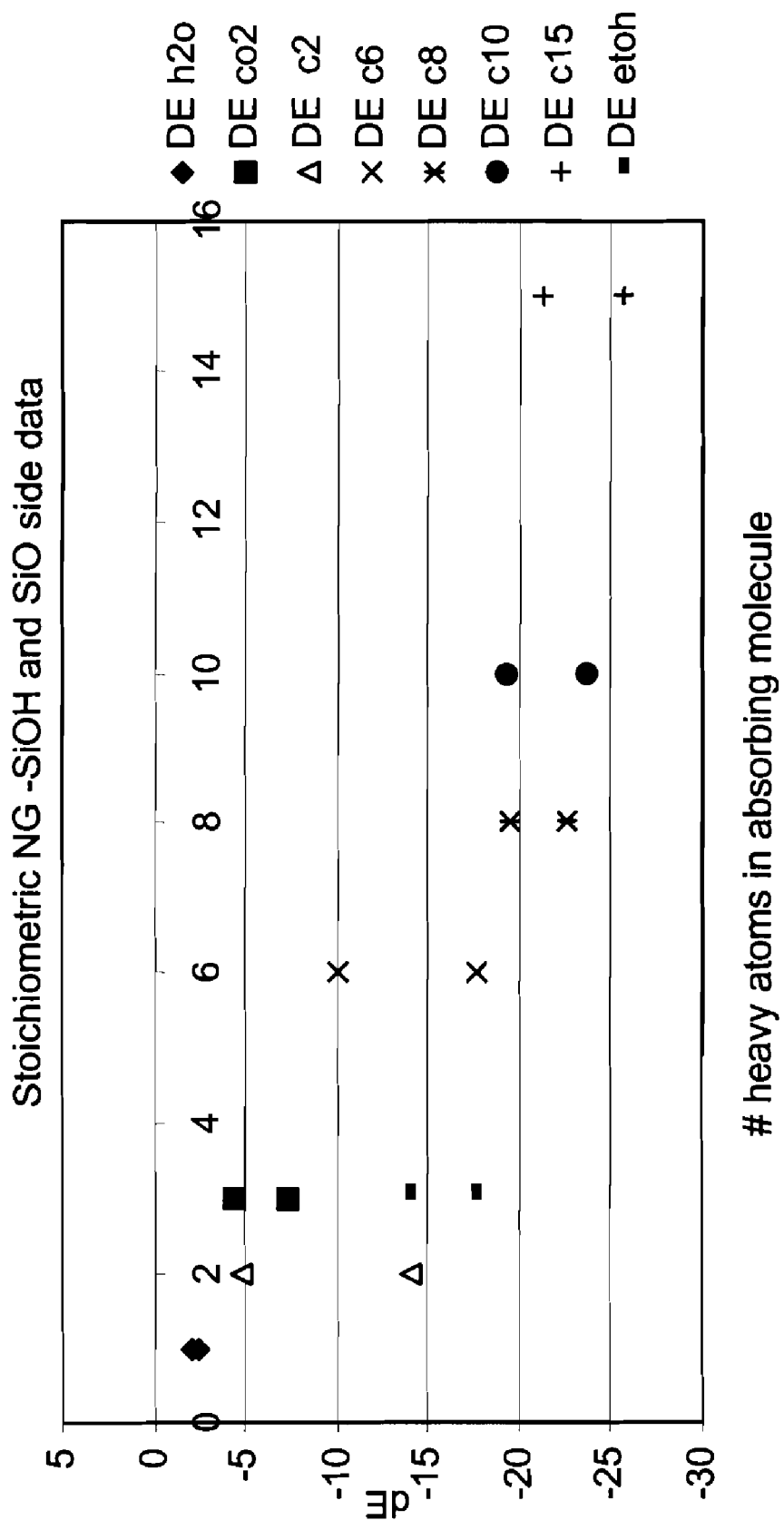
Figure 56:
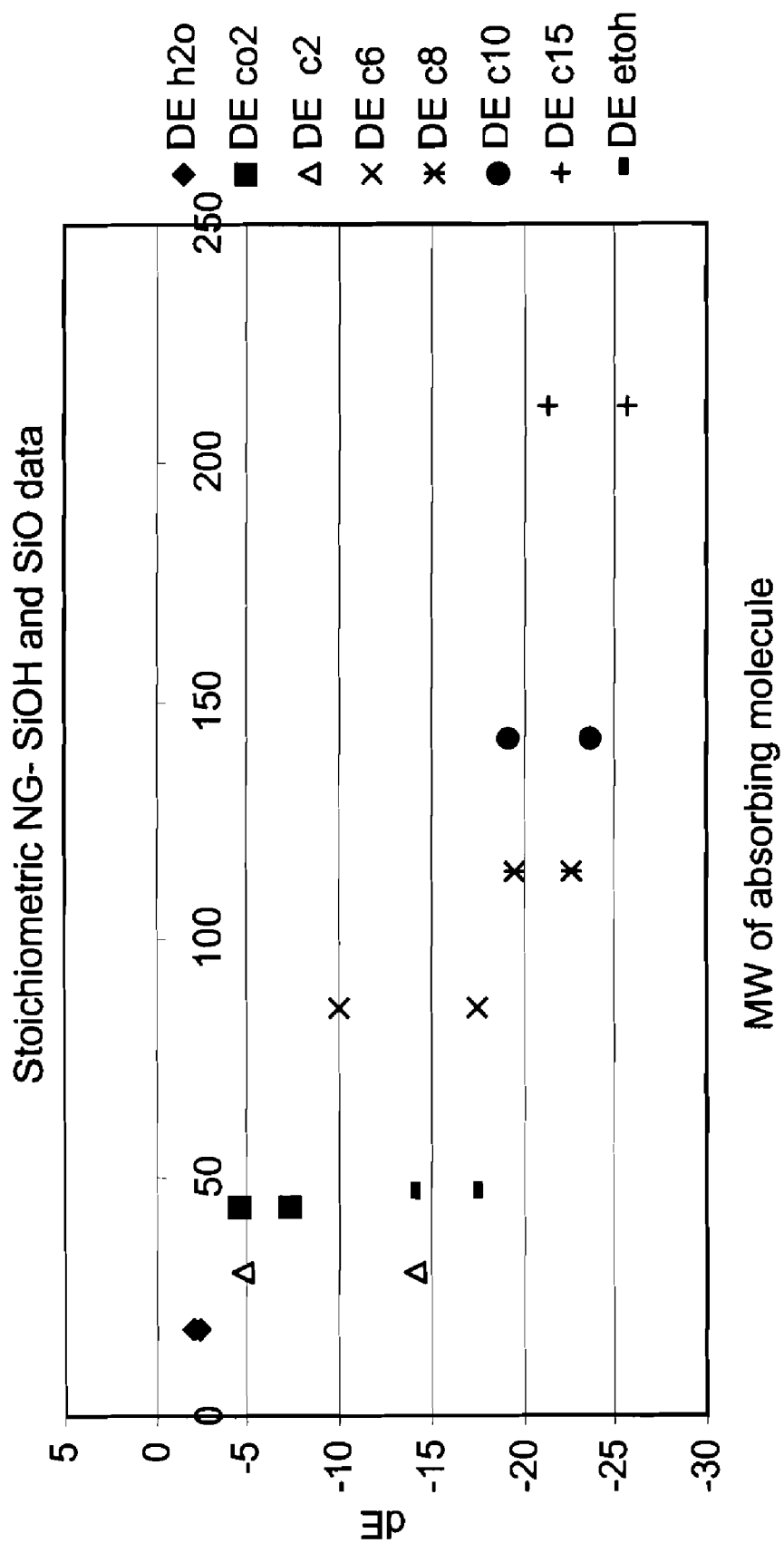
Figure 57:
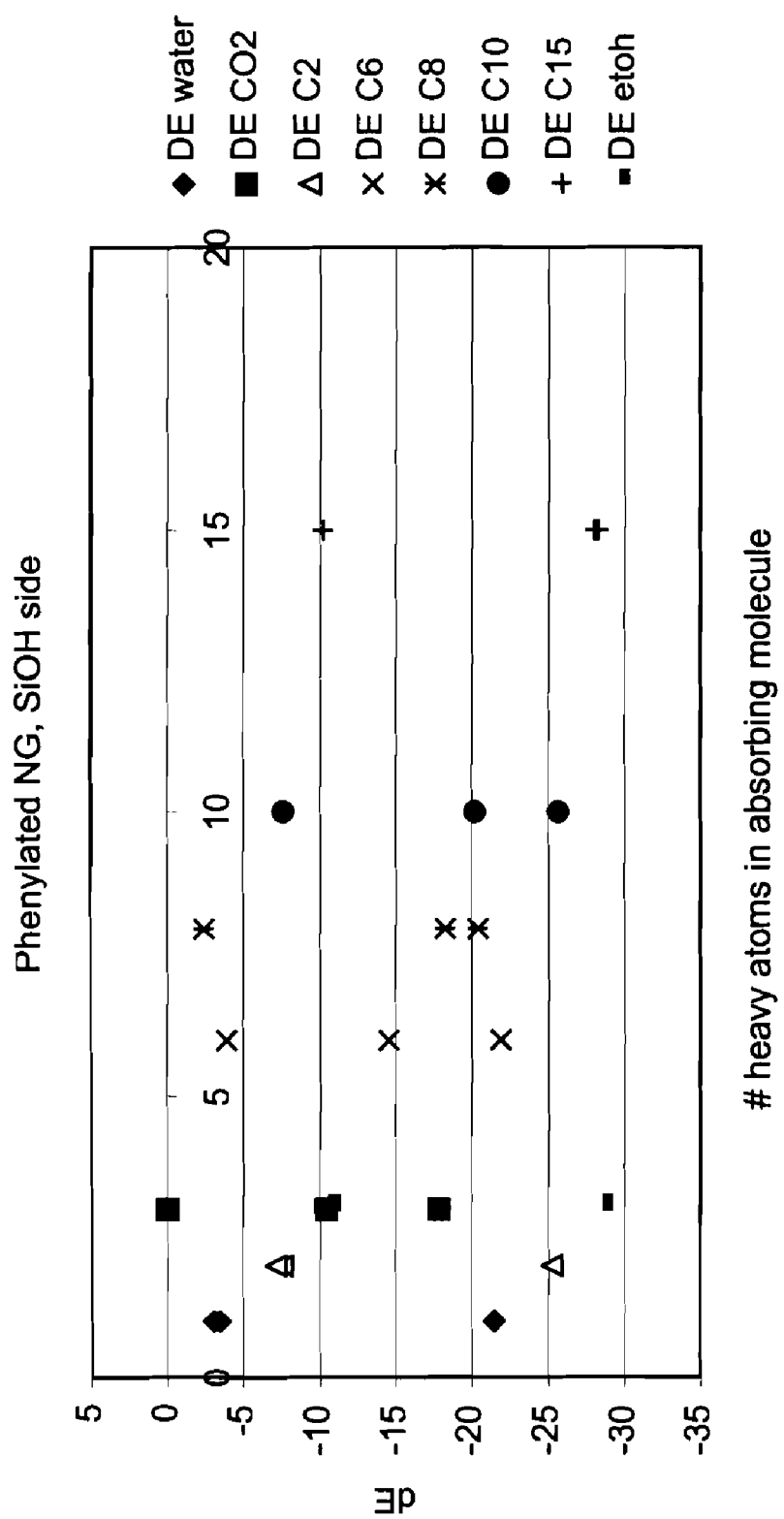

FIG. 48 is a graph showing illustrative relative heater temperatures, along with corresponding concentration pulses produced at each heater element. As indicated above, controller 130 may energize heater elements 20, 22, 24, and 26 in a time phased sequence with voltage signals 71. Illustrative time phased heater relative temperatures for heater elements 20, 22, 24, and 26 are shown by temperature profiles or lines 60, 62, 64, and 66, respectively.

In the example shown, controller 130 (FIG. 46) may first energize first heater element 20 to increase its temperature as shown at line 60 of FIG. 48. Since first heater element 20 is thermally coupled to first interactive element 40 (FIG. 47), the first interactive element desorbs selected constituents into the streaming sample fluid 45 to produce a first concentration pulse 70 (FIG. 48) at the detector 128 or 50, if no other heater elements were to be pulsed. The streaming sample fluid 45 carries the first concentration pulse 70 downstream toward second heater element 22, as shown by arrow 72.

Controller 130 may next energize second heater element 22 to increase its temperature as shown at line 62, starting at or before the energy pulse on element 20 has been stopped. Since second heater element 22 is thermally coupled to second interactive element 42, the second interactive element also desorbs selected constituents into streaming sample fluid 45 to produce a second concentration pulse. Controller 130 may energize second heater element 22 such that the second concentration pulse substantially overlaps first concentration pulse 70 to produce a higher concentration pulse 74, as shown in FIG. 48. The streaming sample fluid 45 carries larger concentration pulse 74 downstream toward third heater element 24, as shown by arrow 76.

Controller 130 may then energize third heater element 24 to increase its temperature as shown at line 64 in FIG. 48. Since third heater element 24 is thermally coupled to third interactive element 44, third interactive element 44 may desorb selected constituents into the streaming sample fluid to produce a third concentration pulse. Controller 130 may energize third heater element 24 such that the third concentration pulse substantially overlaps larger concentration pulse 74 provided by first and second heater elements 20 and 22 to produce an even larger concentration pulse 78. The streaming sample fluid 45 carries this larger concentration pulse 78 downstream toward an "Nth" heater element 26, as shown by arrow 80.

Controller 130 may then energize "N-th" heater element 26 to increase its temperature as shown at line 66. Since "N-th" heater element 26 is thermally coupled to an "N-th" interactive element 46, "N-th" interactive element 46 may desorb selected constituents into streaming sample fluid 45 to produce an "N-th" concentration pulse. Controller 130 may energize "N-th" heater element 26 such that the "N-th" concentration pulse substantially overlaps larger concentration pulse 78 provided by the previous N−1 interactive elements. The streaming sample fluid carries "N-th" concentration pulse 82 to either a separator 126 or a detector 50 or 128, as described below.

As indicated above, heater elements 20, 22, 24, and 26 may have a common length. As such, controller 130 can achieve equal temperatures of the heater elements by providing an equal voltage, current, or power pulse to each heater element. The voltage, current, or power pulse may have any desired shape including a triangular shape, a square shape, a bell shape, or any other shape. An approximately square shaped current, power or voltage pulse 71 may be used to achieve temperature profiles 60, 62, 64, and 66 as shown in FIG. 48. The temperature profiles look like that, and note that the desorbed species are generated with a small time delay, relative to the voltage pulses.

To simplify the control of the heater elements, the length of each successive heater element may be kept constant to produce the same overall heater resistance between heater elements, thereby allowing equal voltage, current, or power pulses to be used to produce similar temperature profiles. Alternatively, the heater elements may have different lengths, and the controller may provide different voltage, current, or power pulse amplitudes to the heater element to produce a similar temperature profile.

FIGS. 49-63 involve adsorption energies of phenylated silica-NG. A model such energy minimization on phenylated nanoglass (same stoichiometry as an Me case). Cases may include unhydrated, hydrated, all SiO side, and SiOH containing side (OH/Si=1/10). Absorbing molecules may include ethane, hexane, octane, decane, pentadecane, carbon dioxide, water and ethanol.

Observations that may be note are energy trends and separation of energies seem more consistent on the unhydrated surfaces, so still showing water sensistivity. The unhydrated SiOH side shows better energy separation of compounds than the unhydrated SiO side. An unhydrated phenylated surface should have better energy separation than unhydrated methylated NG case. There may less energy separation between CO2 and EtOH than the methylated nanoglass case. Comparing SiOH vs. SiO side, the SiO side seems to have better general trends-consistent with methylated (standard) NG case. Unhydrated case may be more consistent in energy trends than hydrated case. SiOH side may have a little better selectivity (energy separation) than SiO side when unhydrated SiOH side has a little better selectivity (energy separation) than SiO side when unhydrated. There may be less energy separation between CO2 and EtOH than a Me-NG case. As to unhydrated cases, phenylated may give better energy separation.

There may be specific compounds labelled as SiOH vs. SiO. Regardless of hydration state, the SiO side seems more trend consistent. However, there appears anomalous behavior with C10 due to a hydrated surface that wasn't pre-equilibrated with water.

Figure 58:
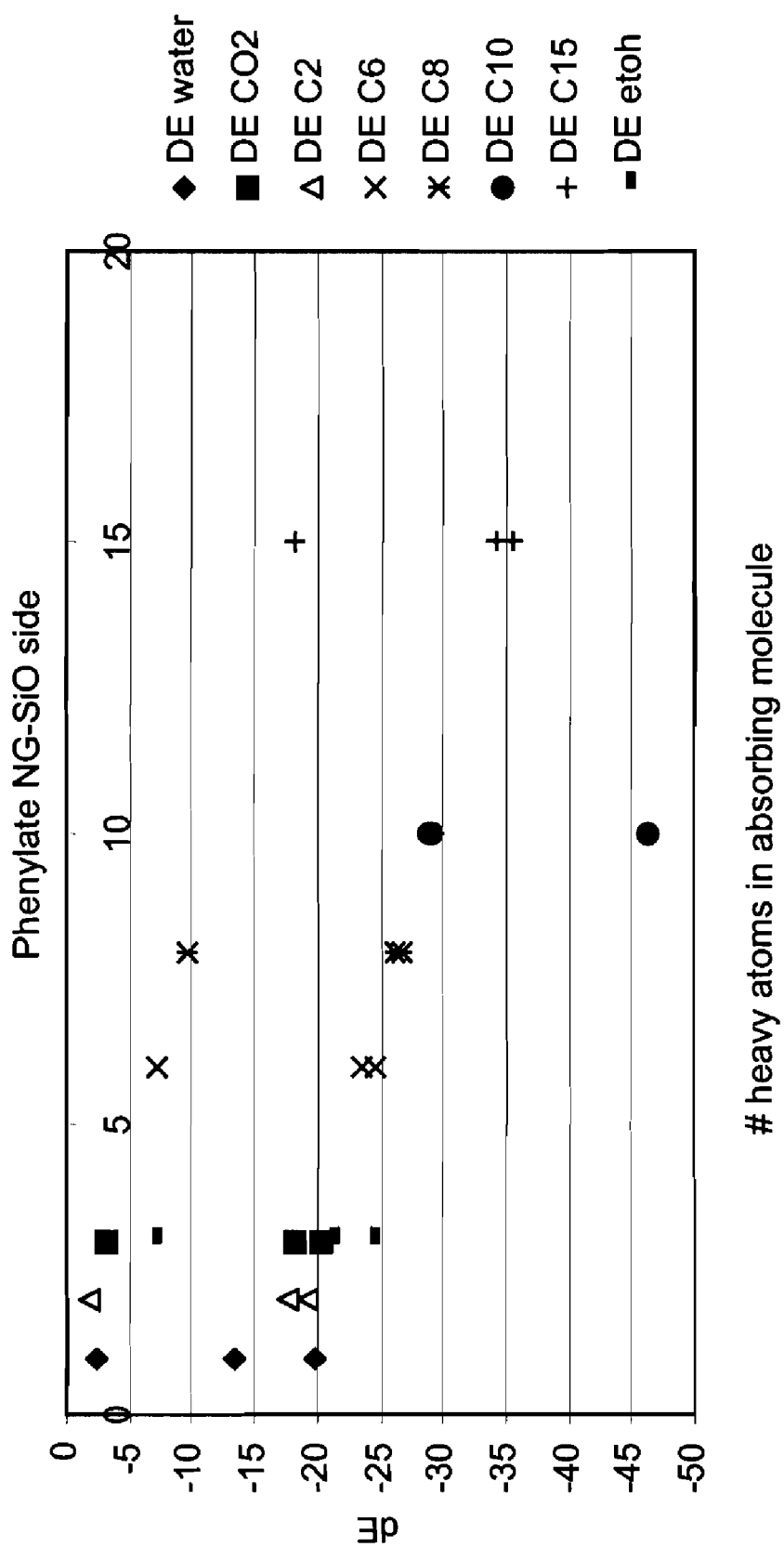
Figure 59:
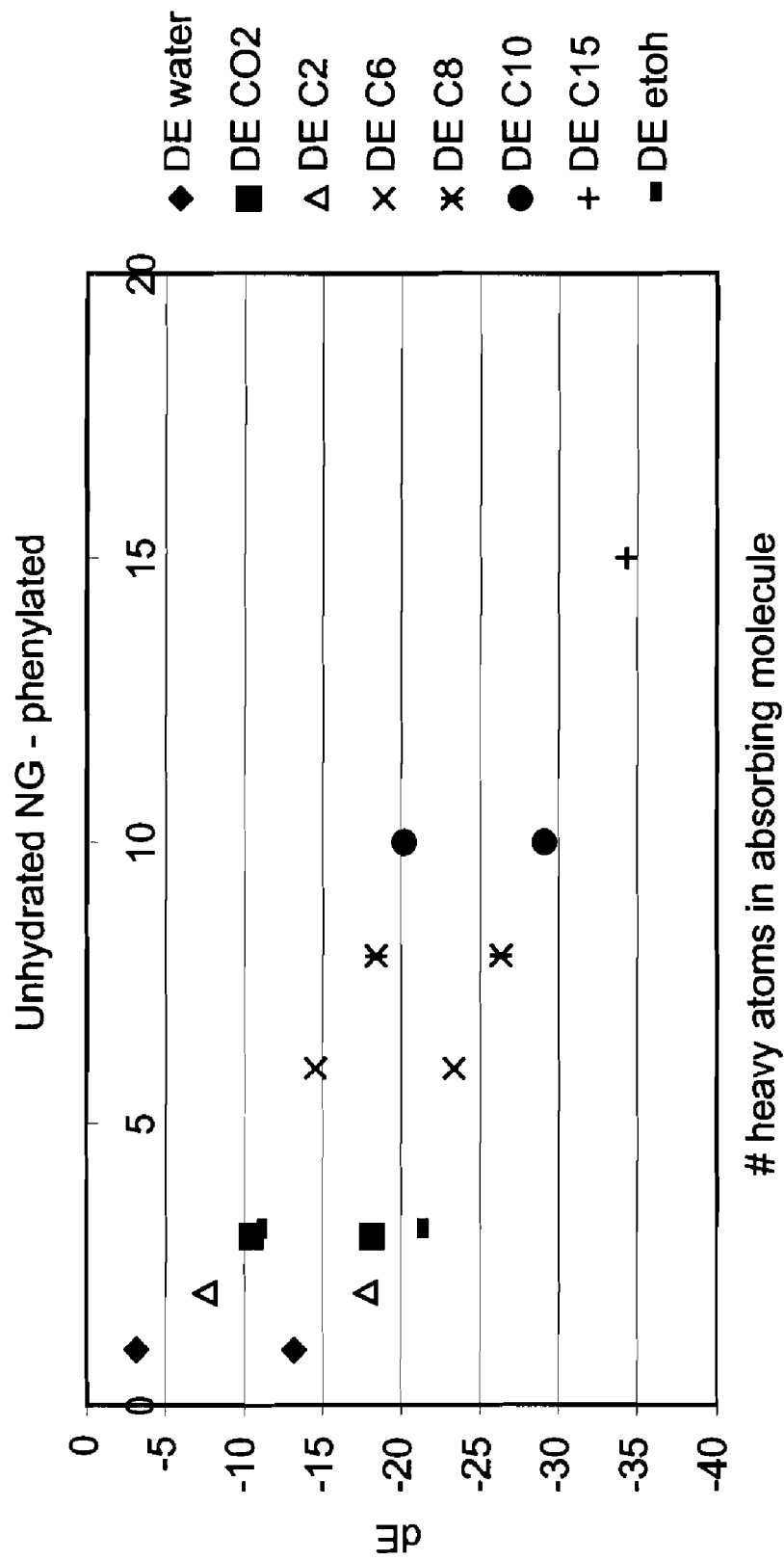
Figure 60:
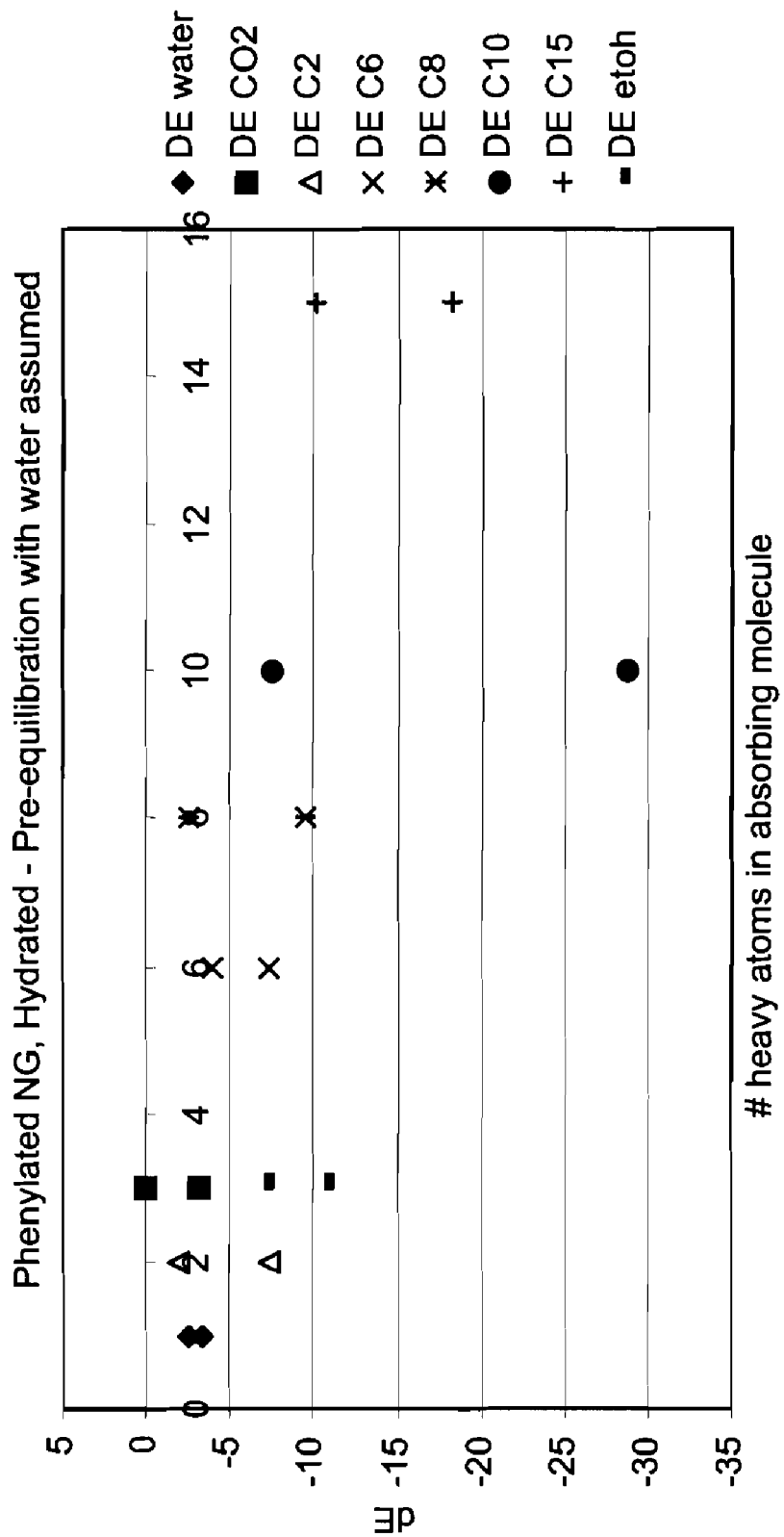
Figure 61:
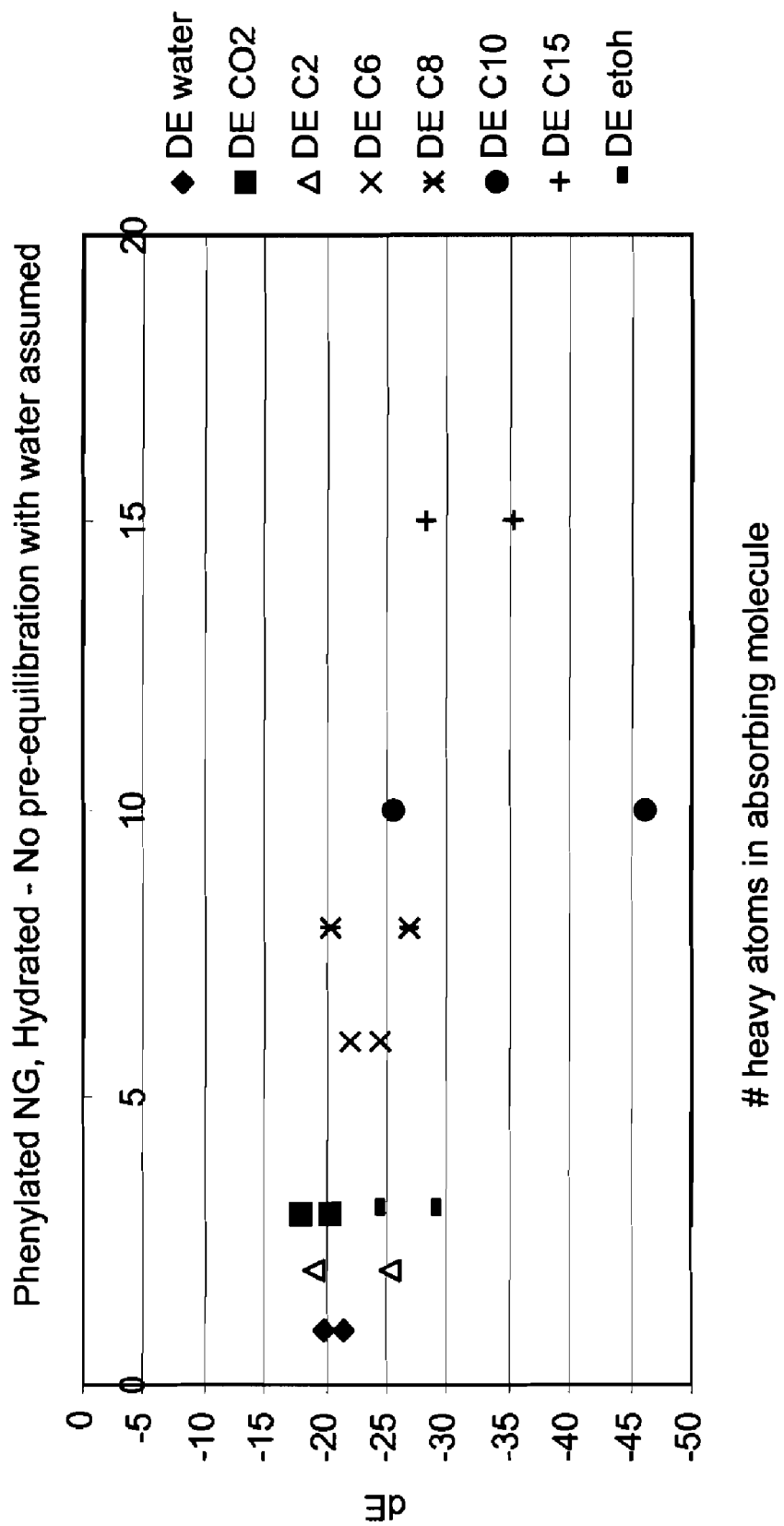
Figure 62:
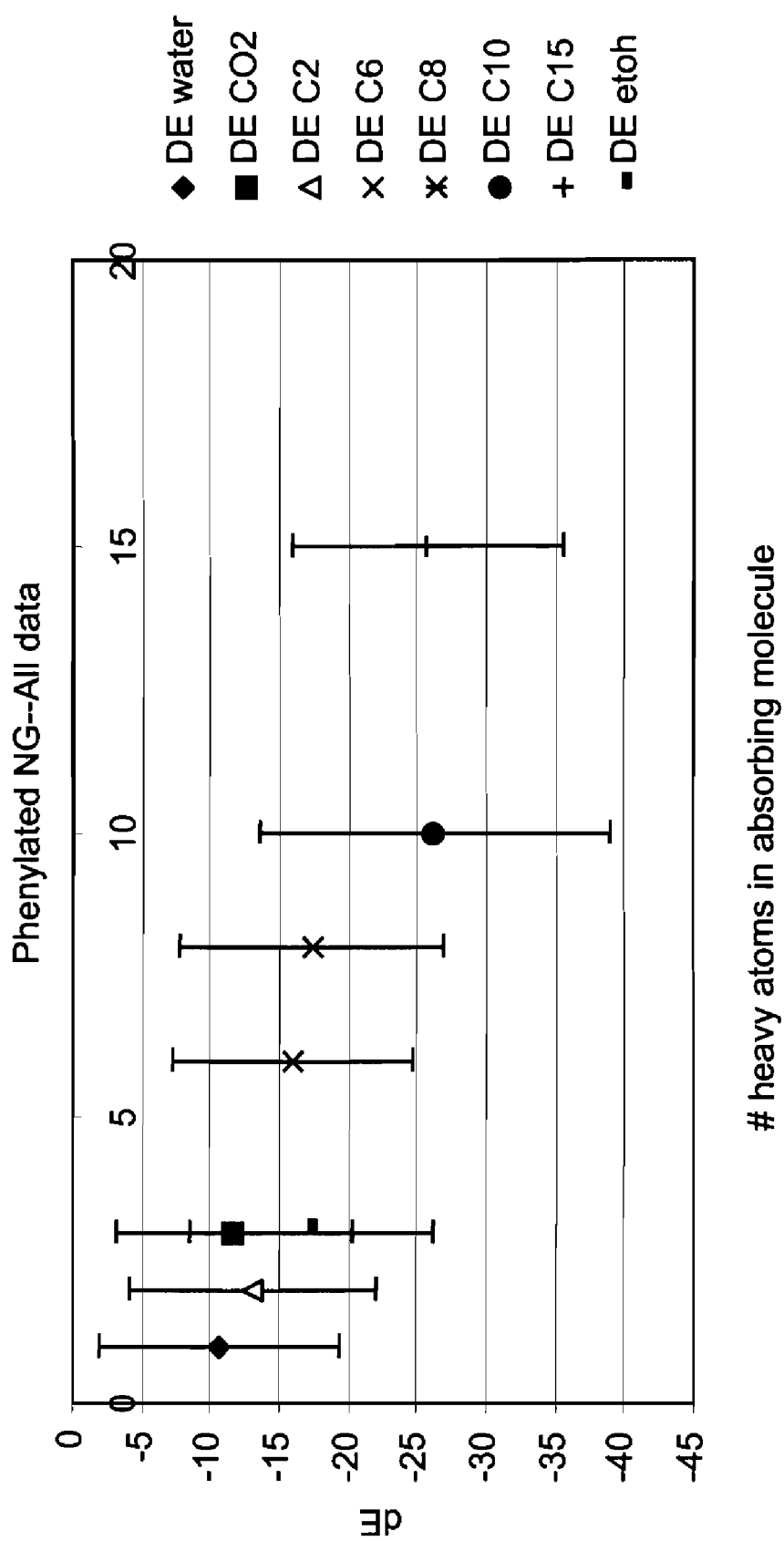
Figure 63:
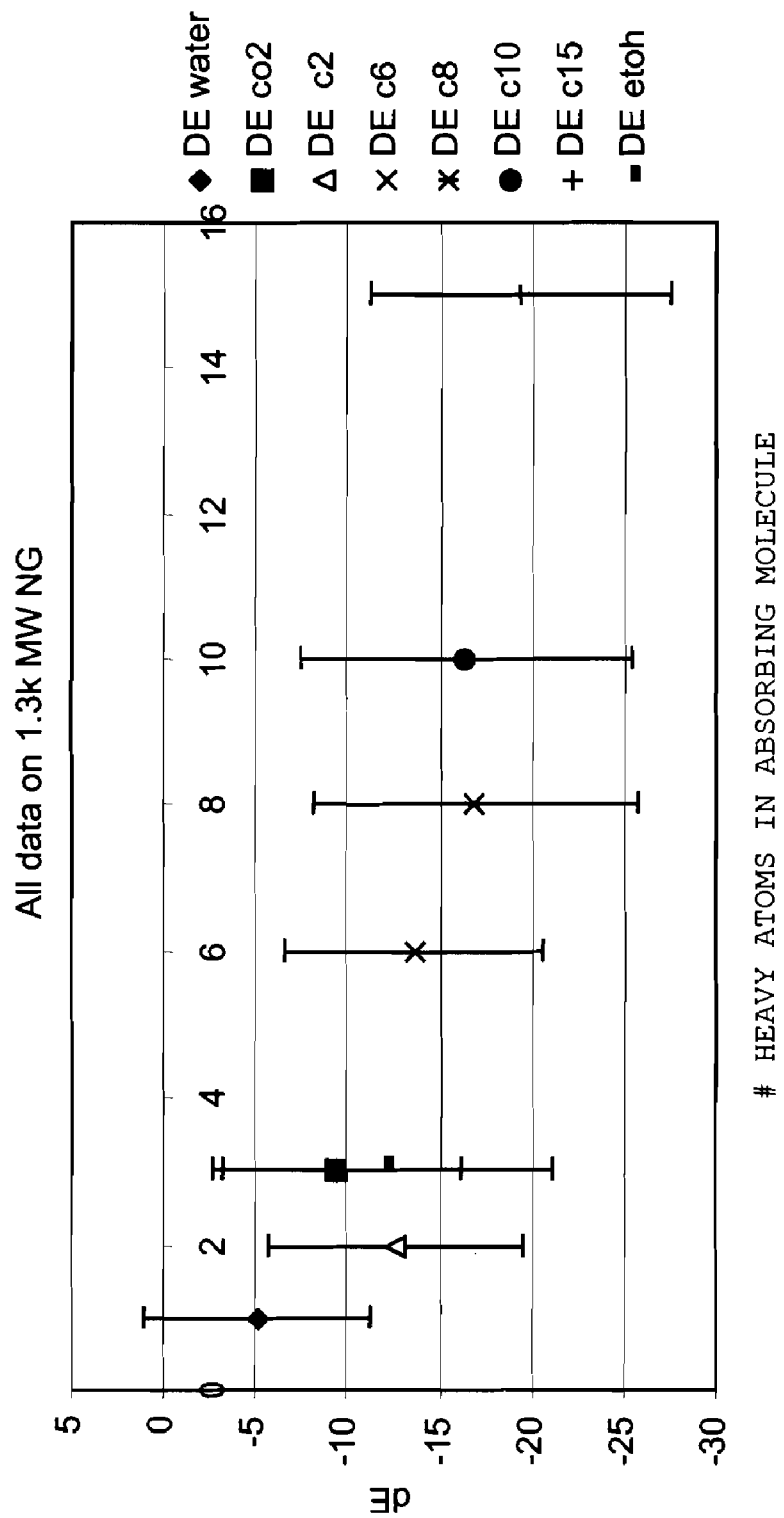
Figures 64, 65:
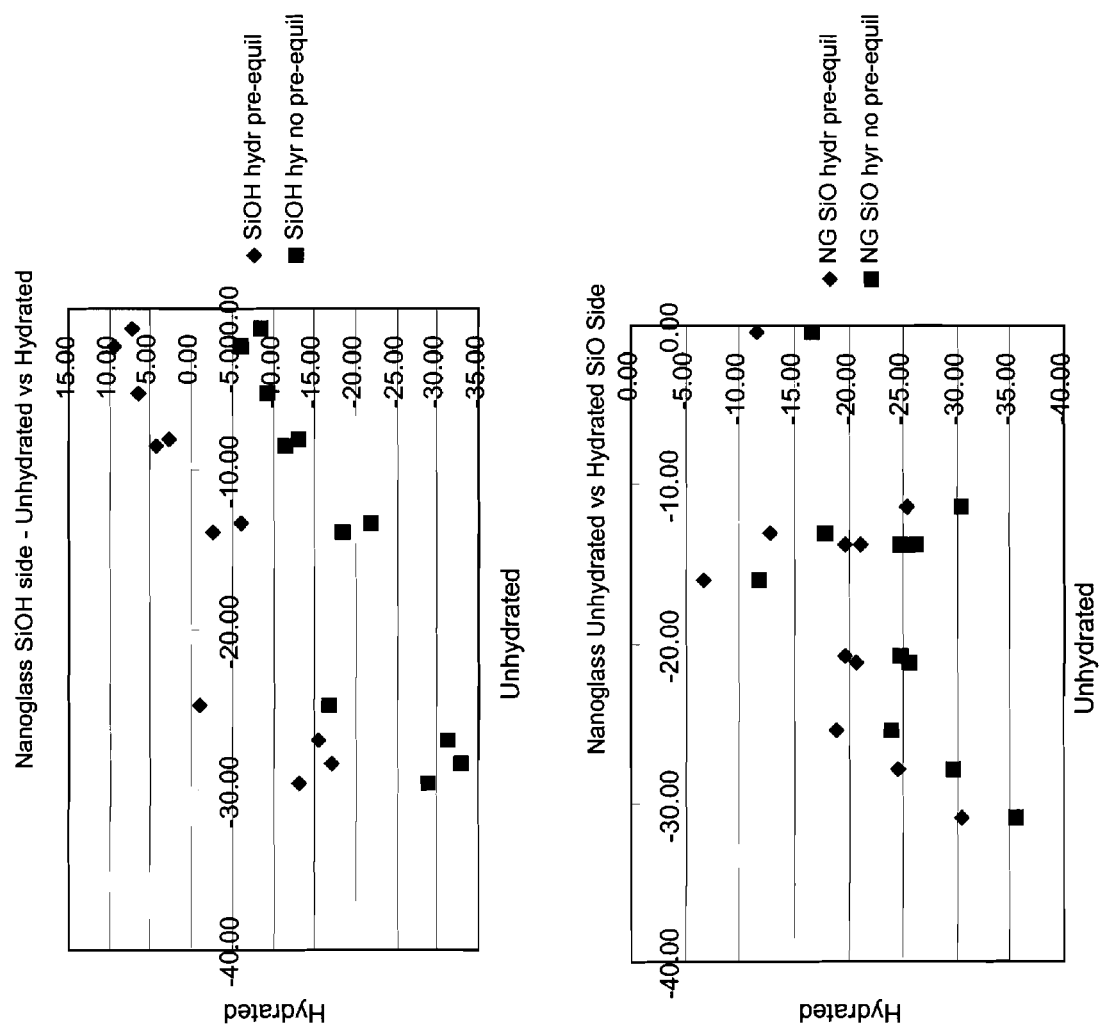
Figure 66:
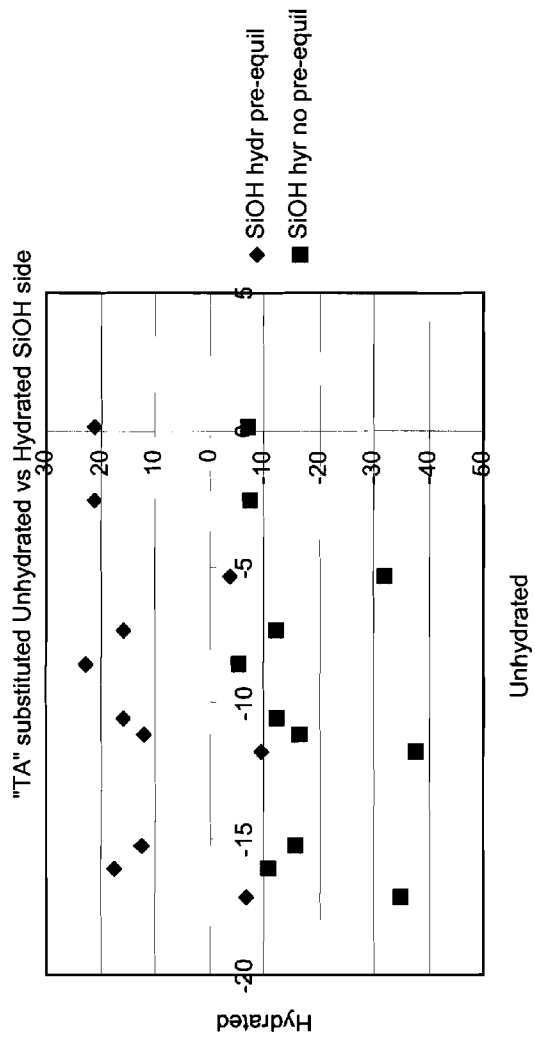
Figure 67:
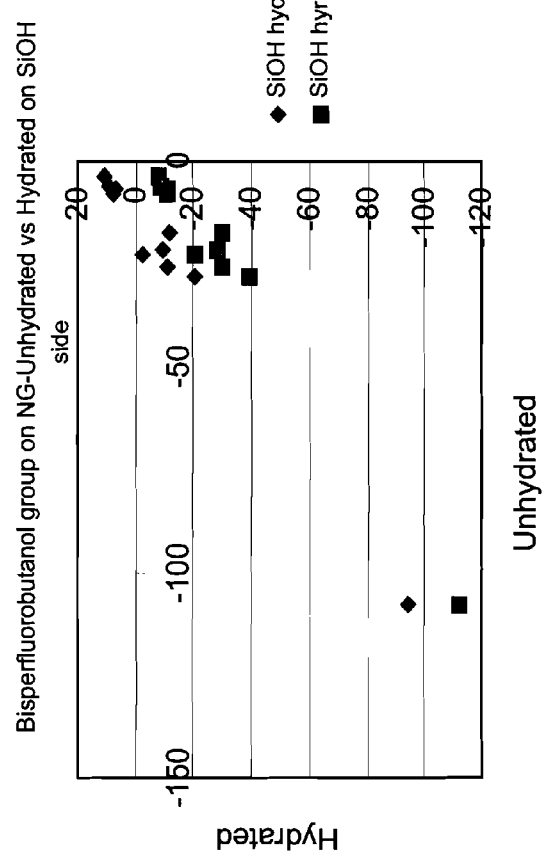
Figure 68:
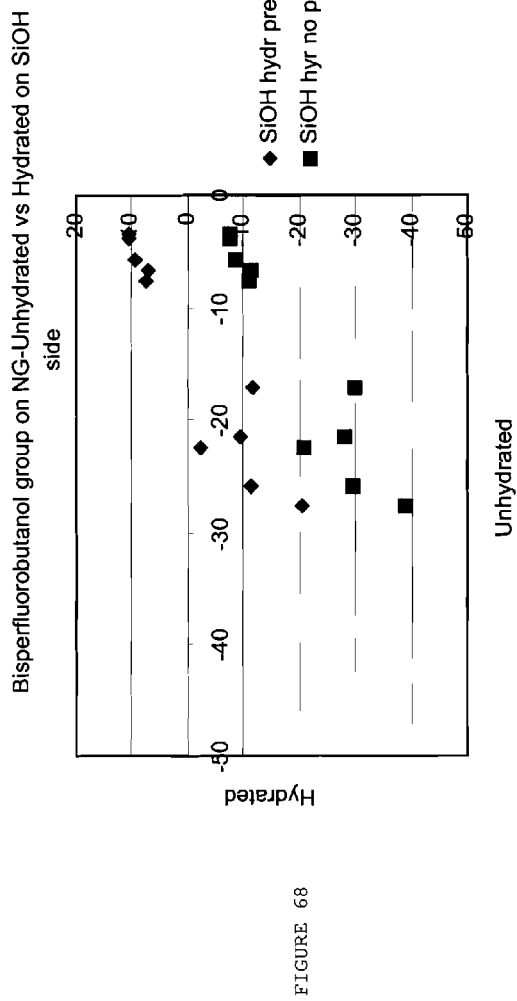
Figure 69:
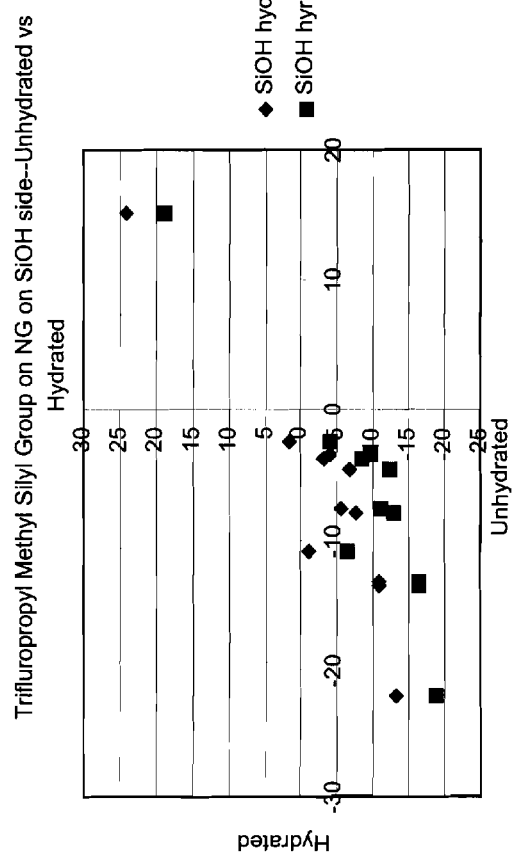
Figure 70:
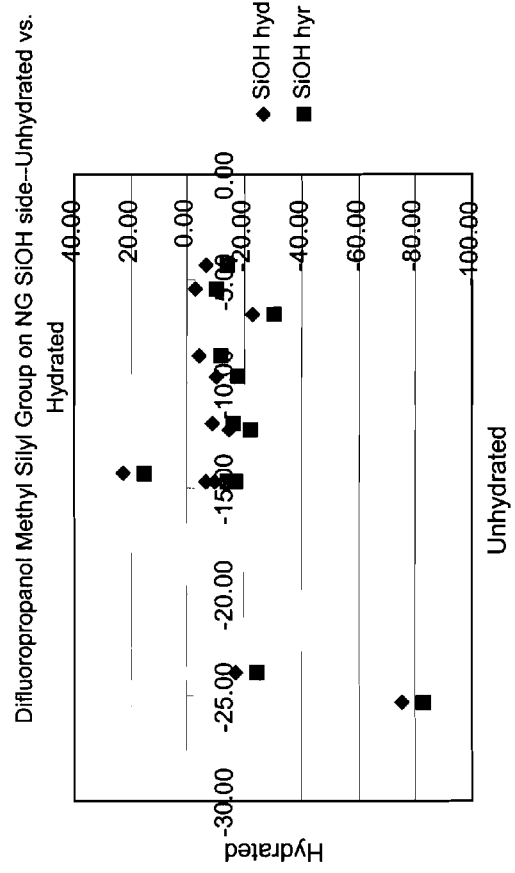
Figure 71:
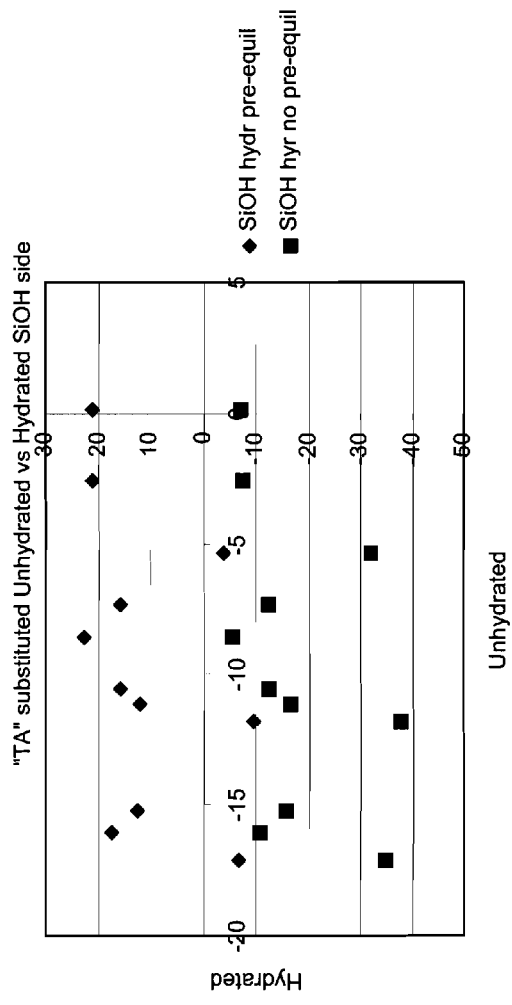
Figure 72:
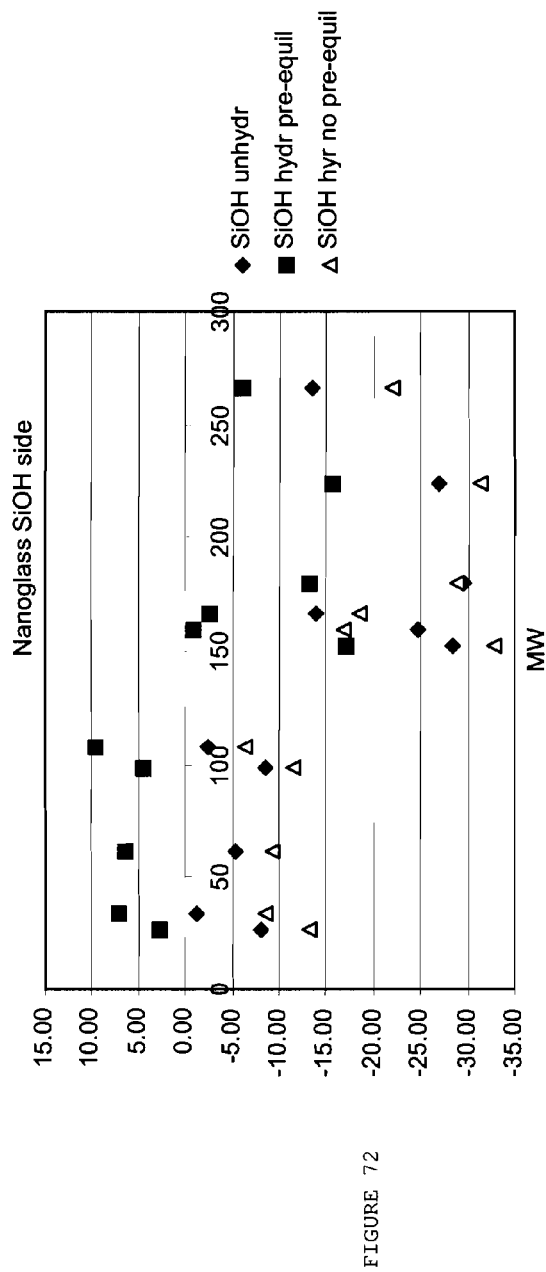
Figure 73:
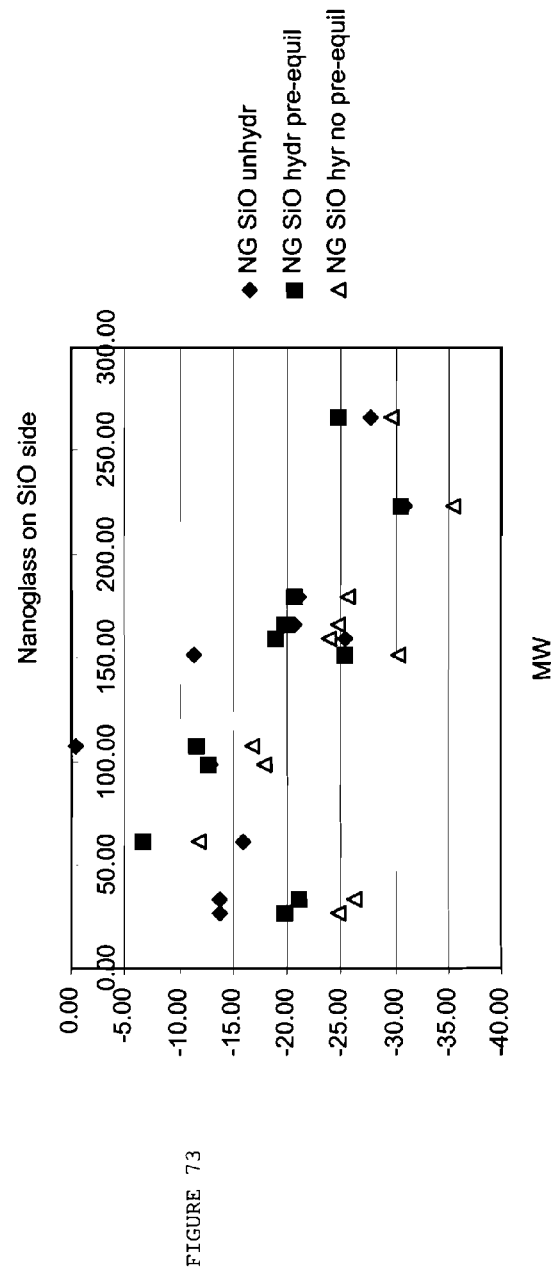
Figure 74:
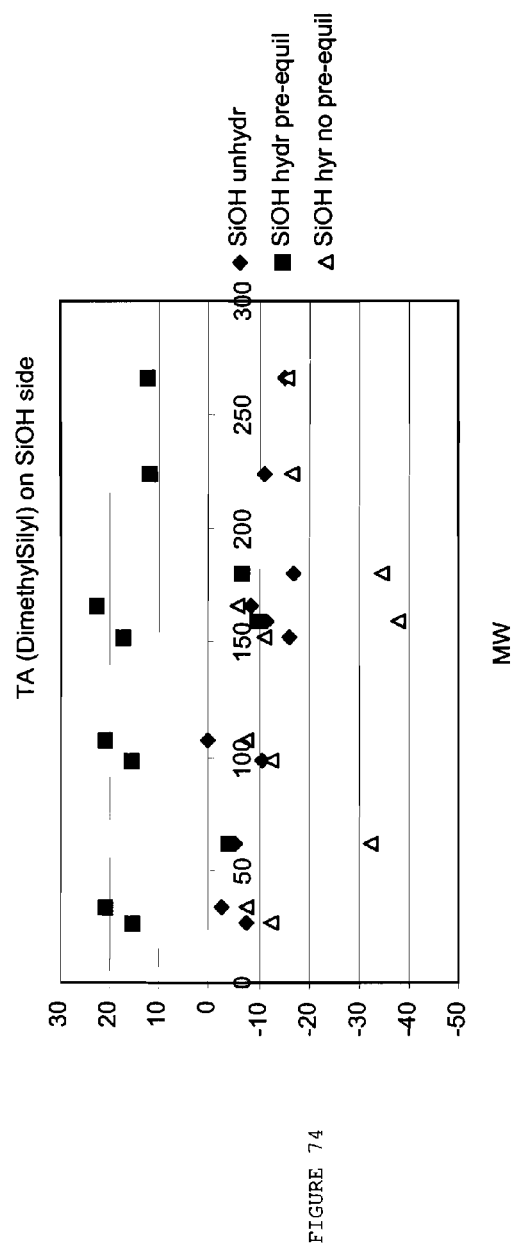
Figure 75:
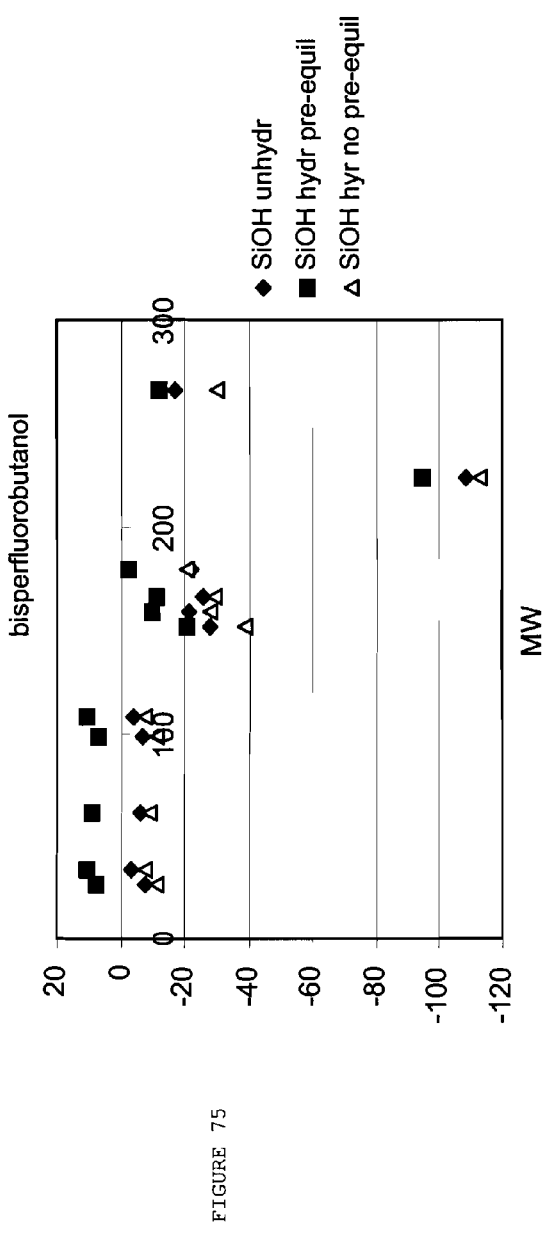
Figure 76:
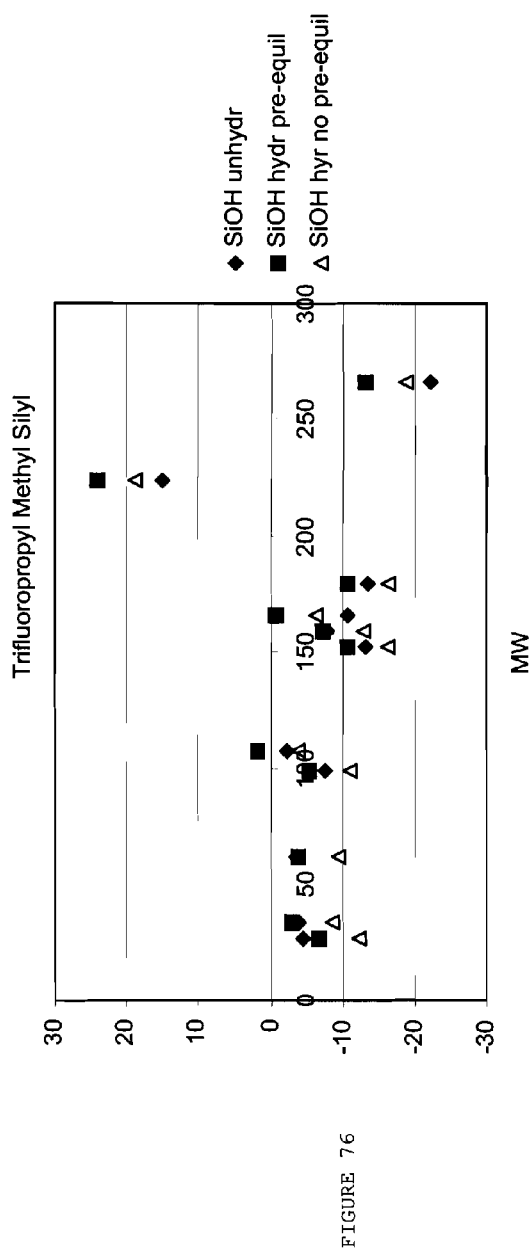
Figure 77:
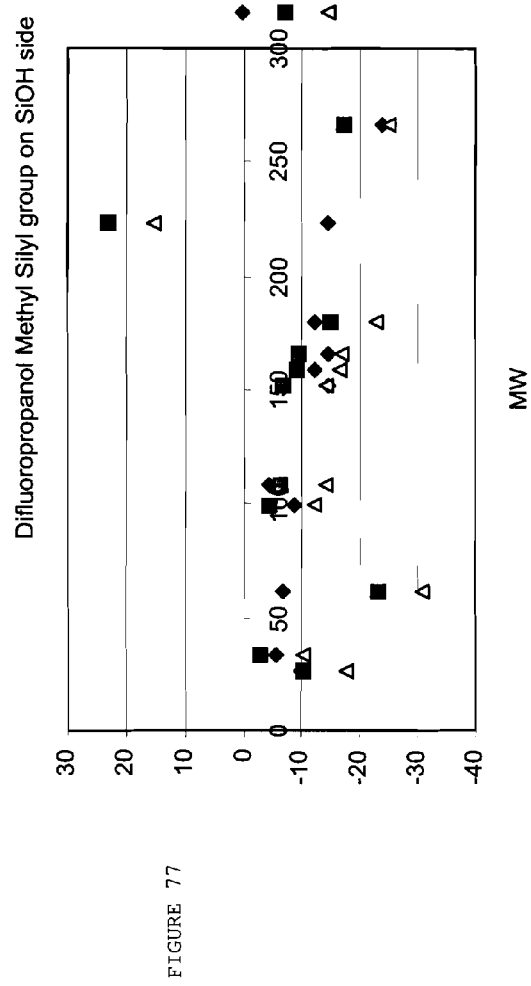
Figure 78:
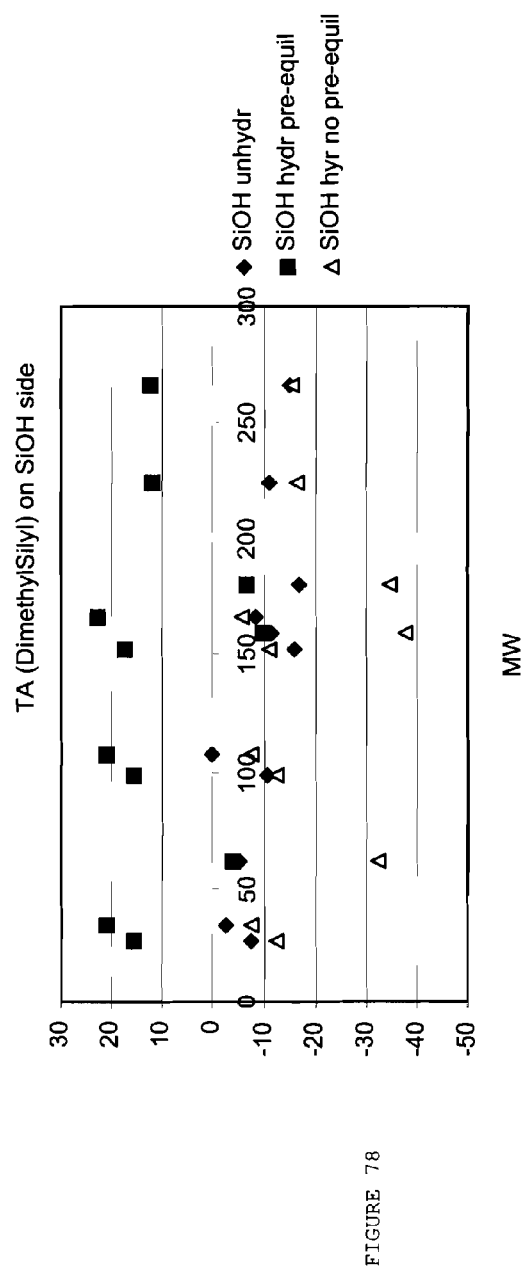
Figure 79:
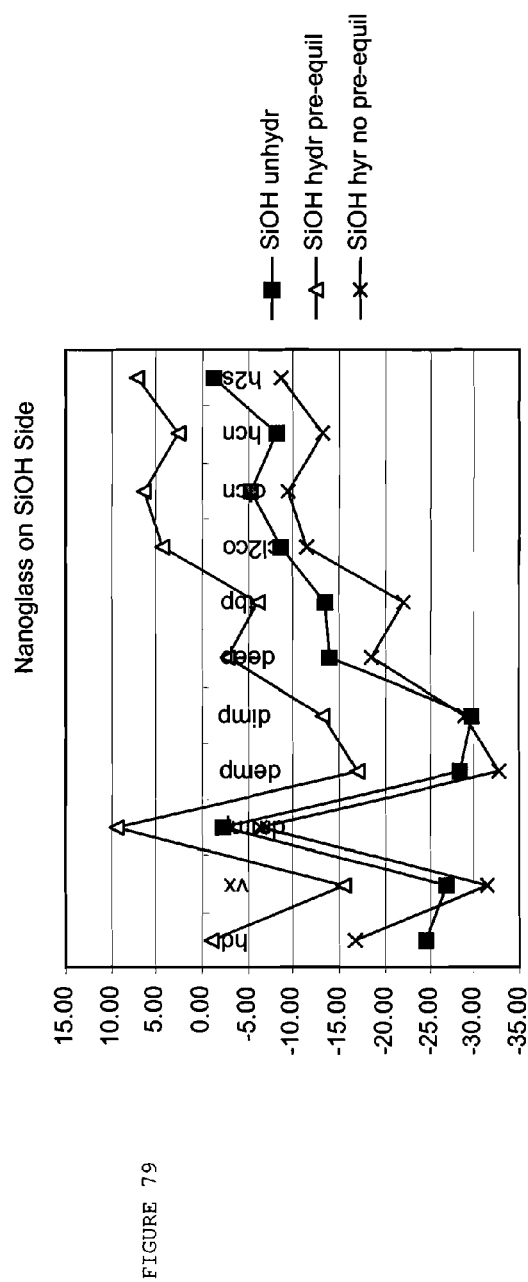
Figure 80:
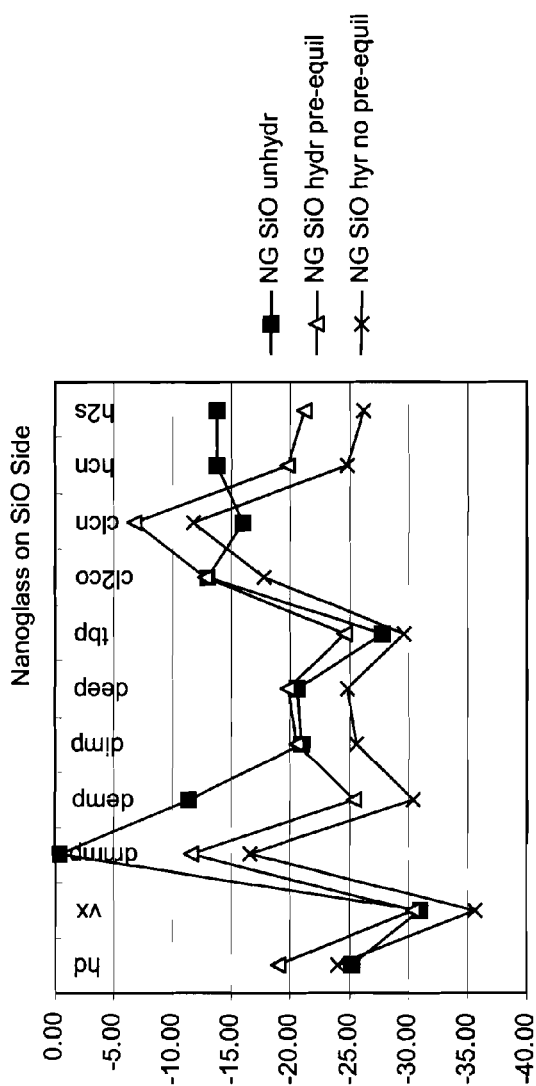
Figure 81:
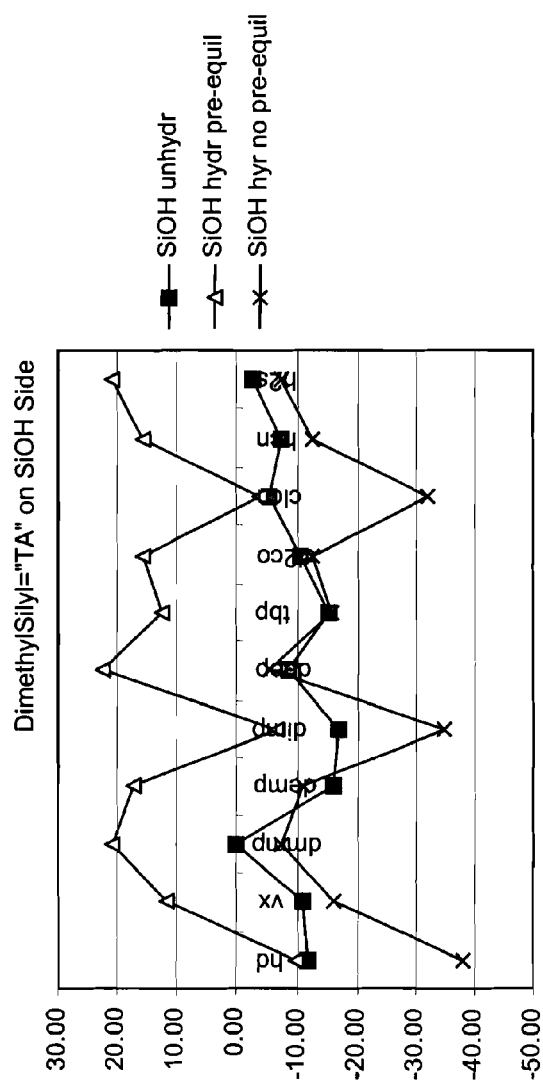
Figure 82:
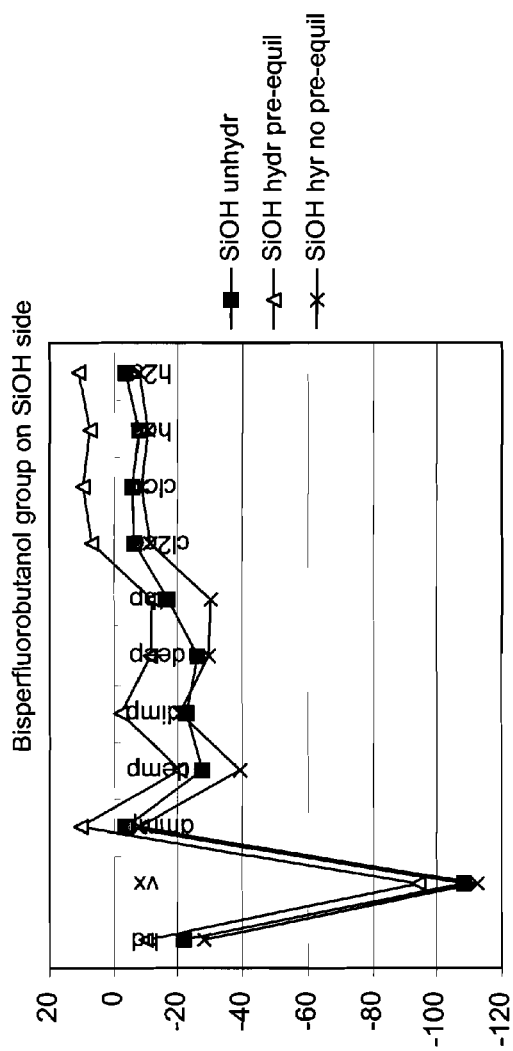
Figure 83:
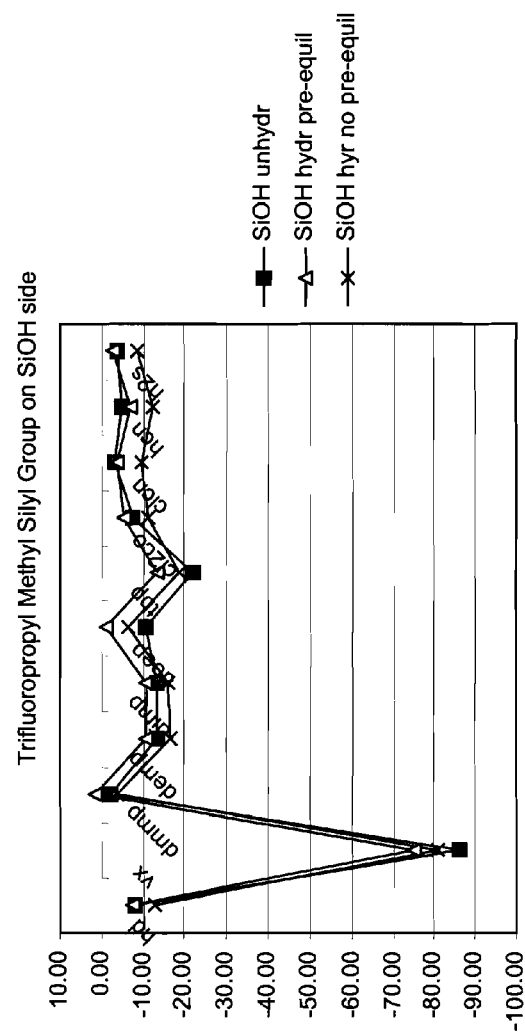
Figure 84:
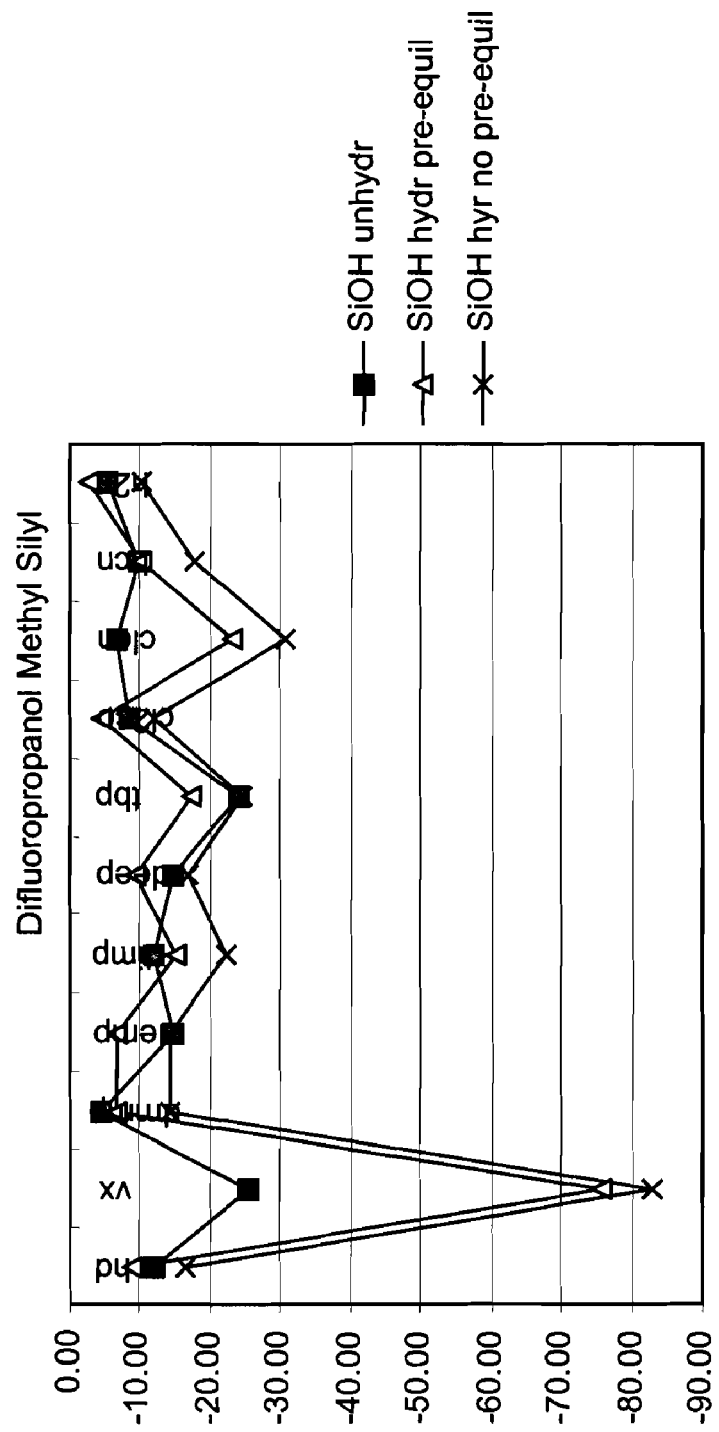
Figure 92:
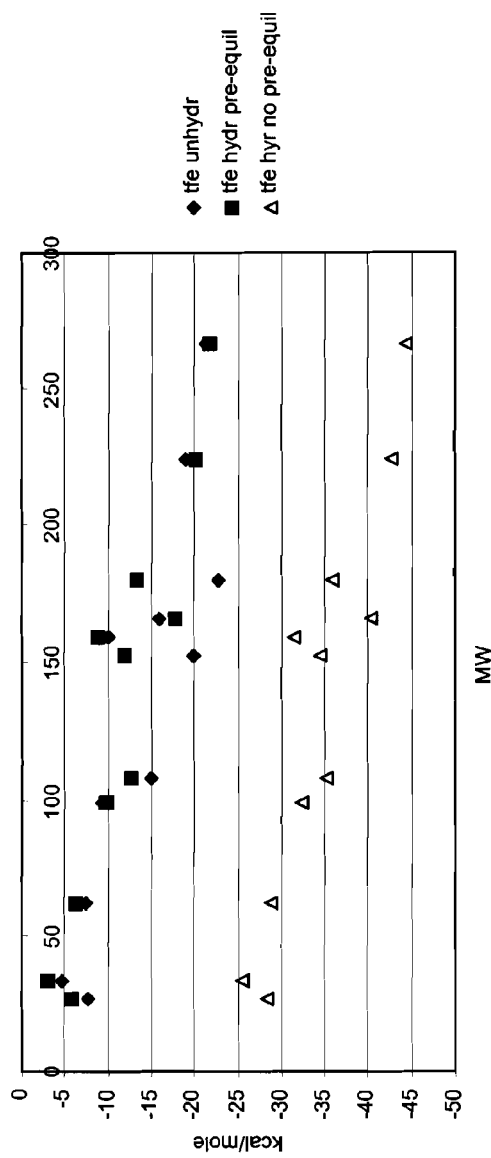
Figure 93:
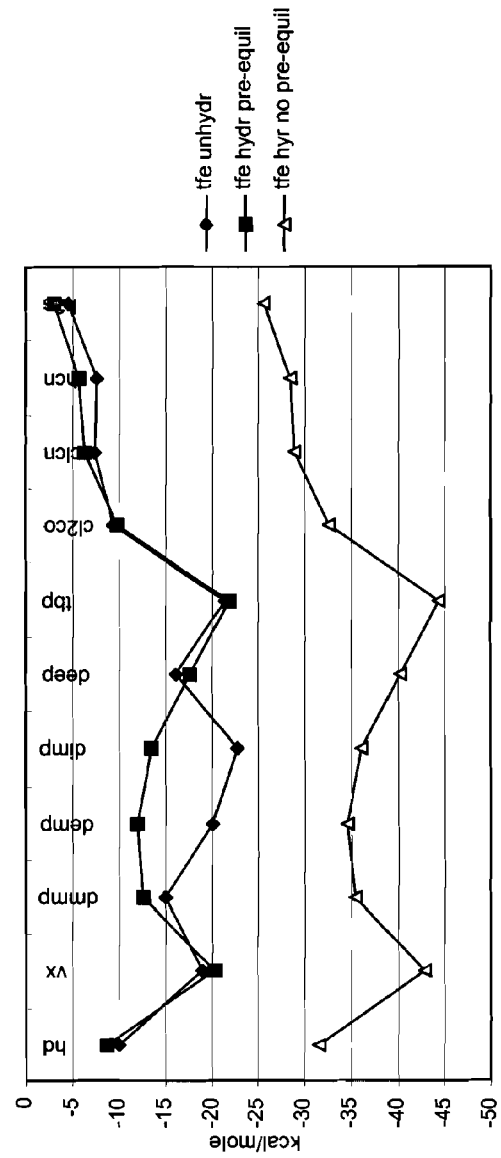
Figure 97:
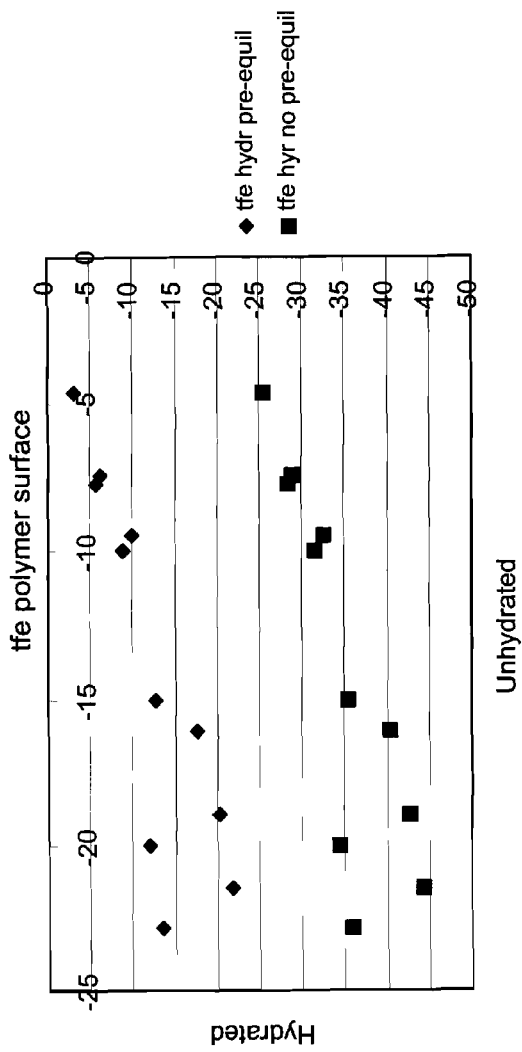
Figure 98:
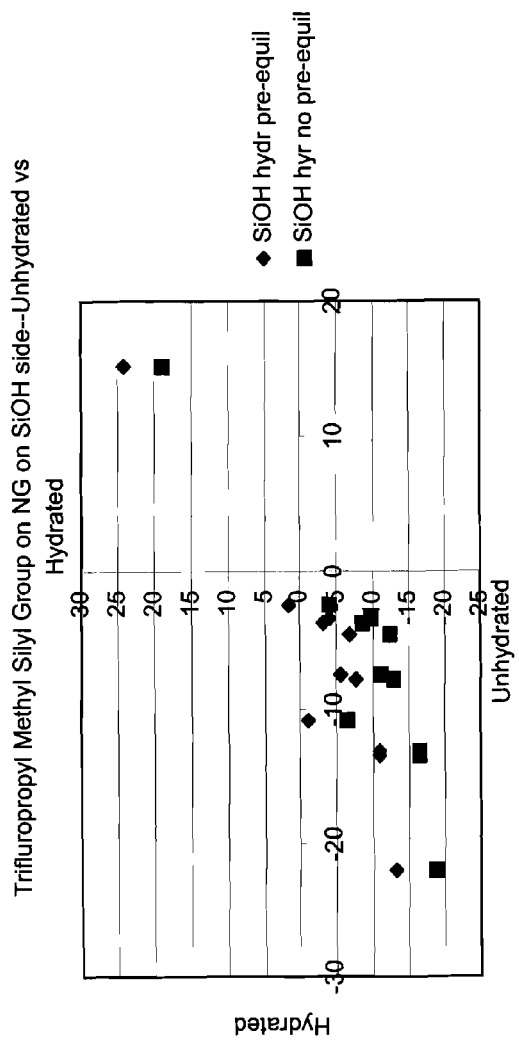
Figure 99:
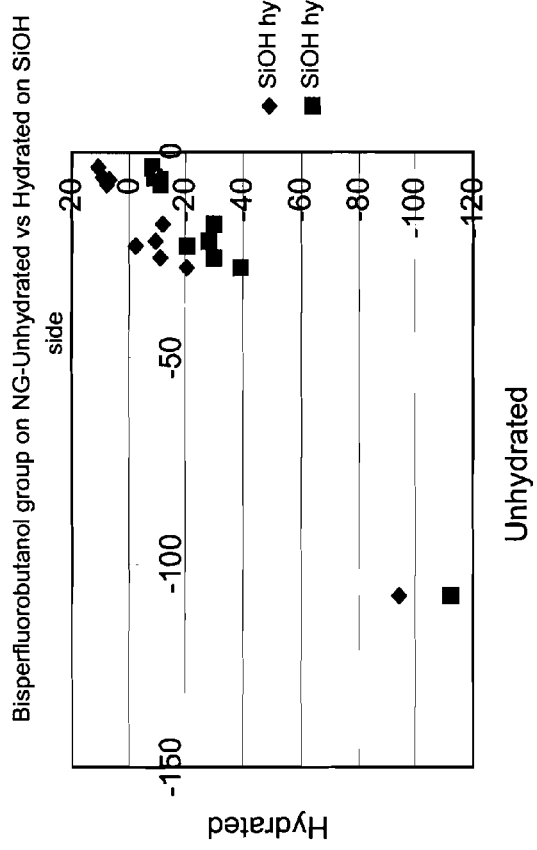
Figure 100:
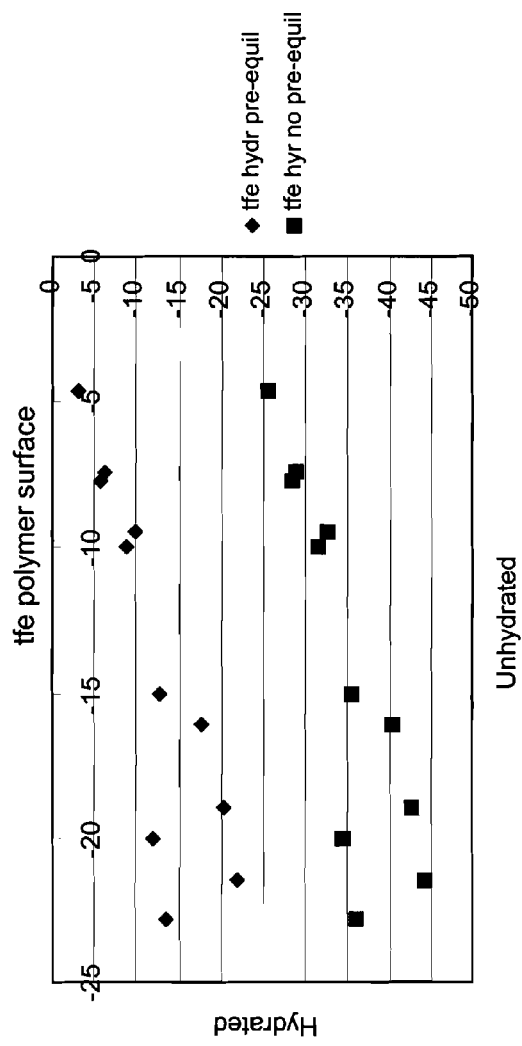
Figure 101:
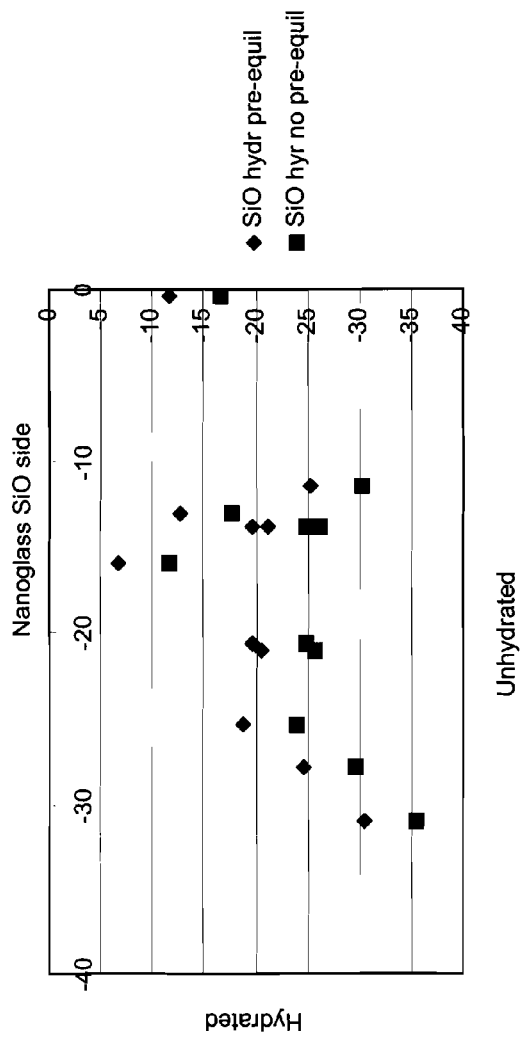
Figure 102:
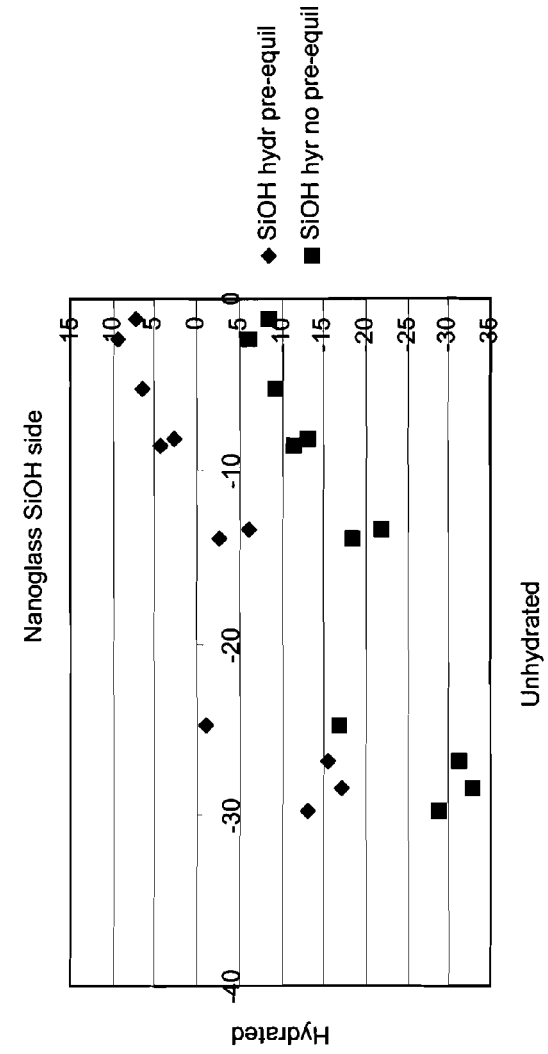
Figure 103:
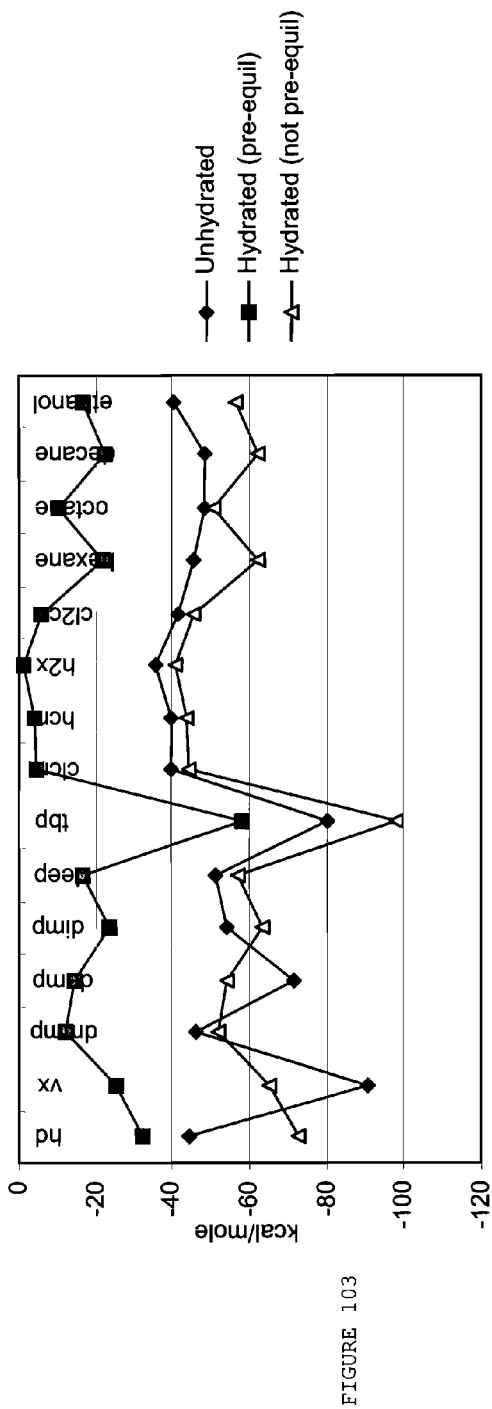
Figure 104:
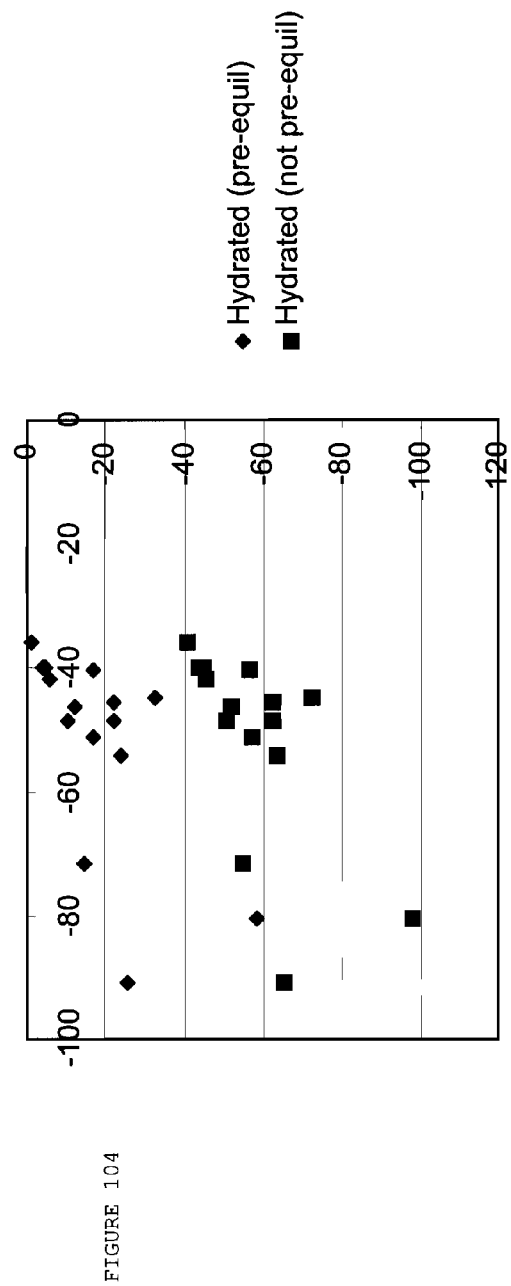
Figure 105:
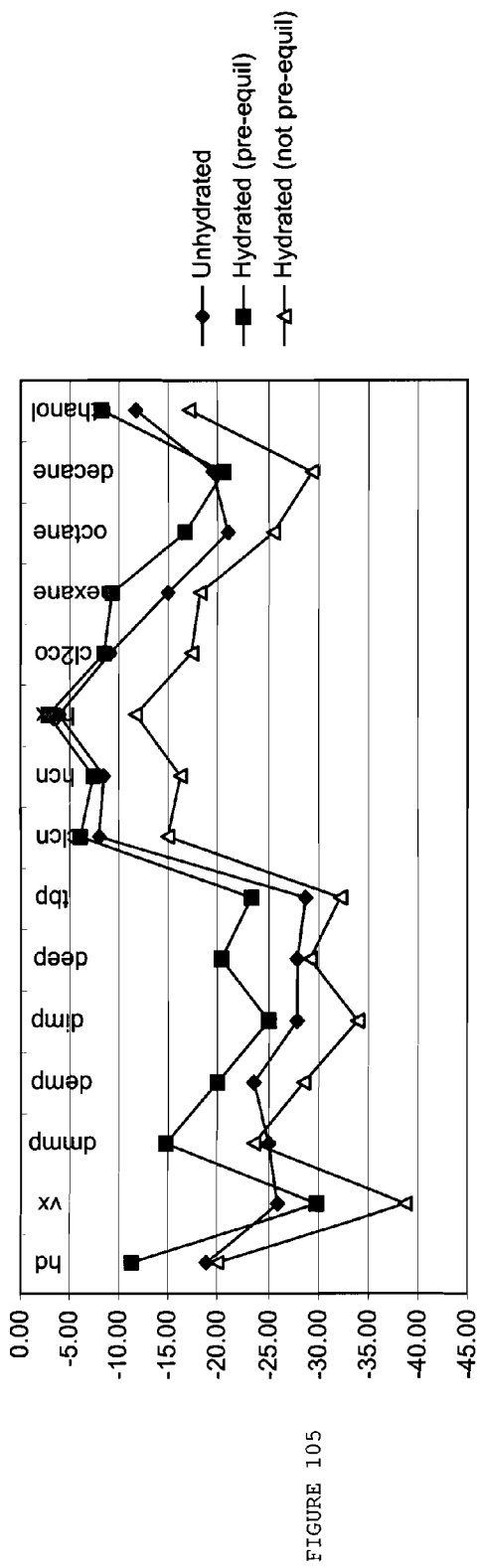
Figure 106:
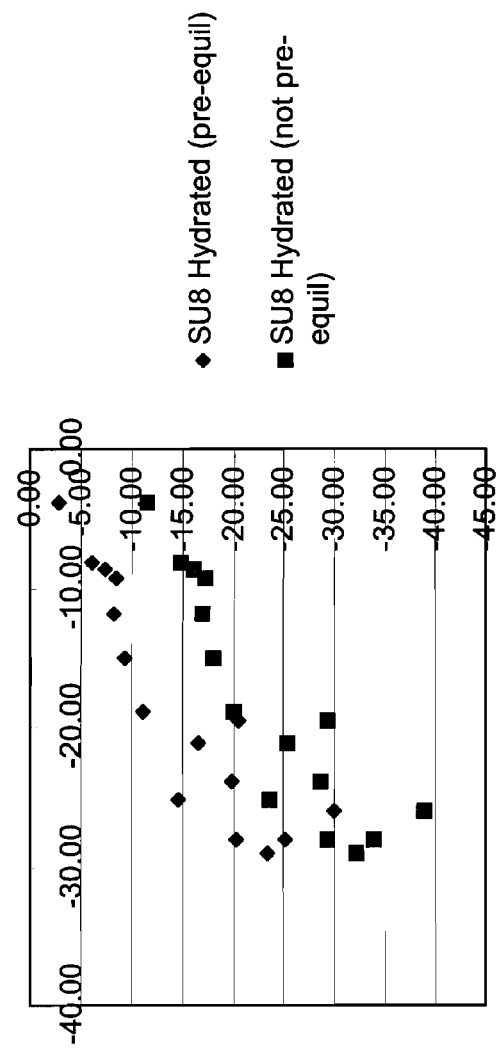
Figures 114, 115:
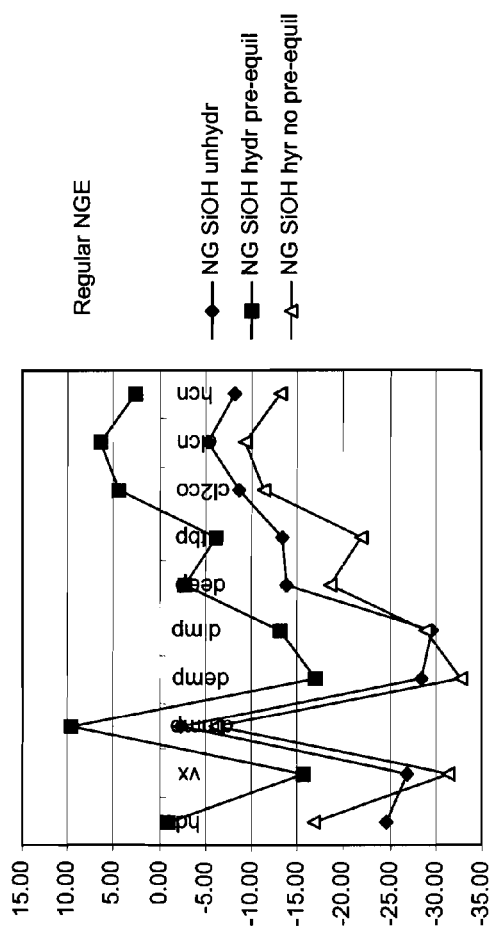
Figures 116, 117:
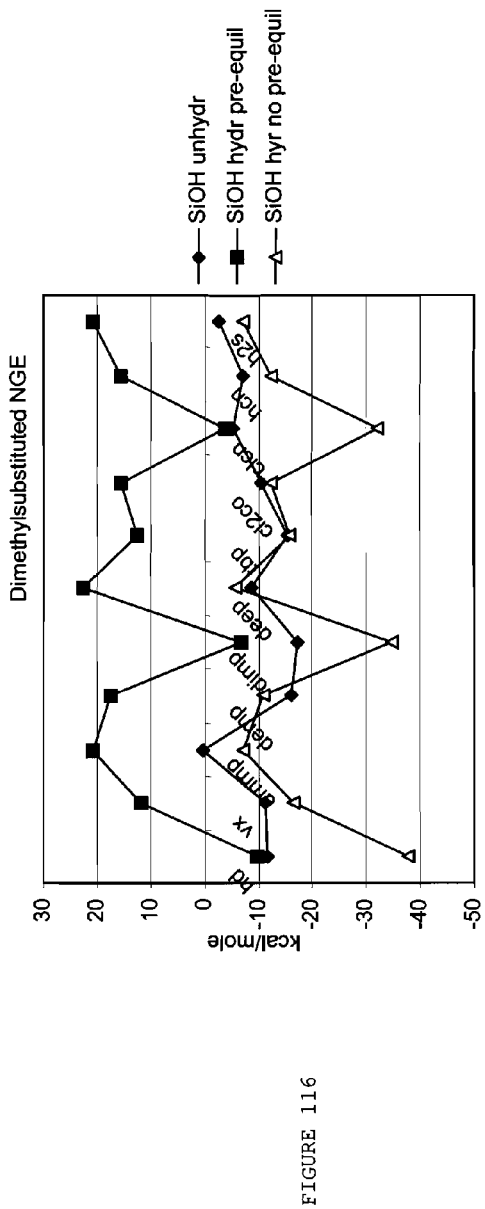
Figures 118, 119:
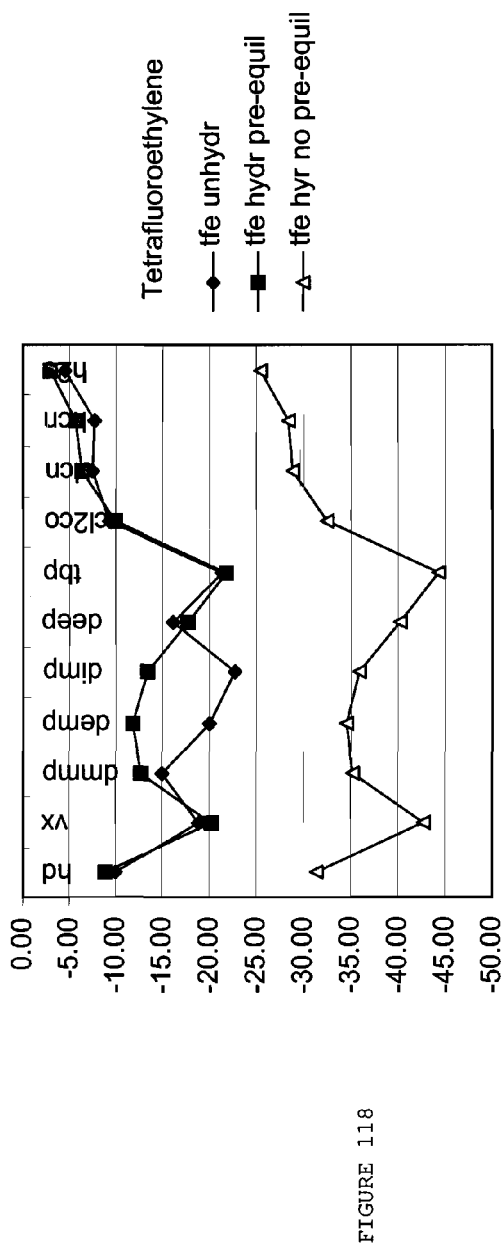
Figures 120, 121:
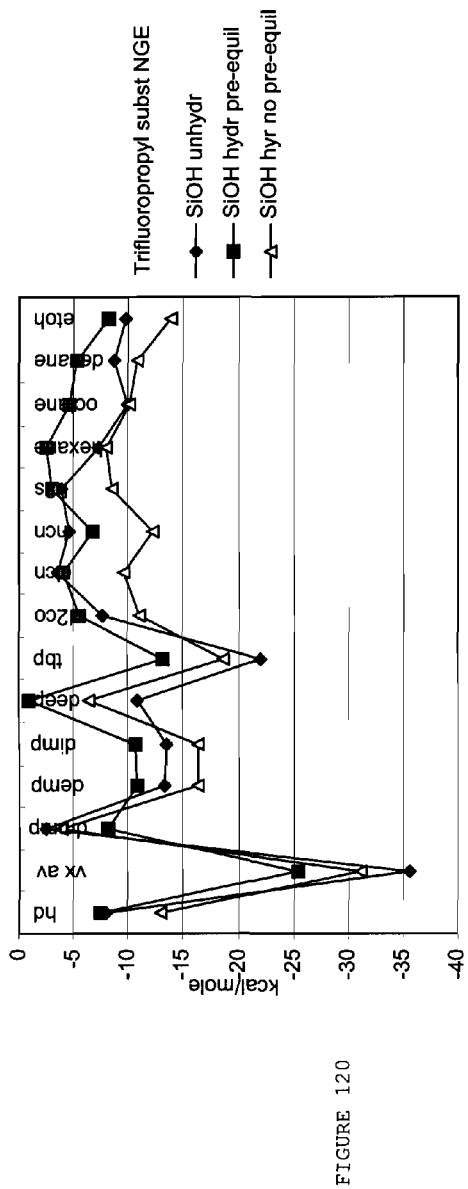
Figures 122, 123:
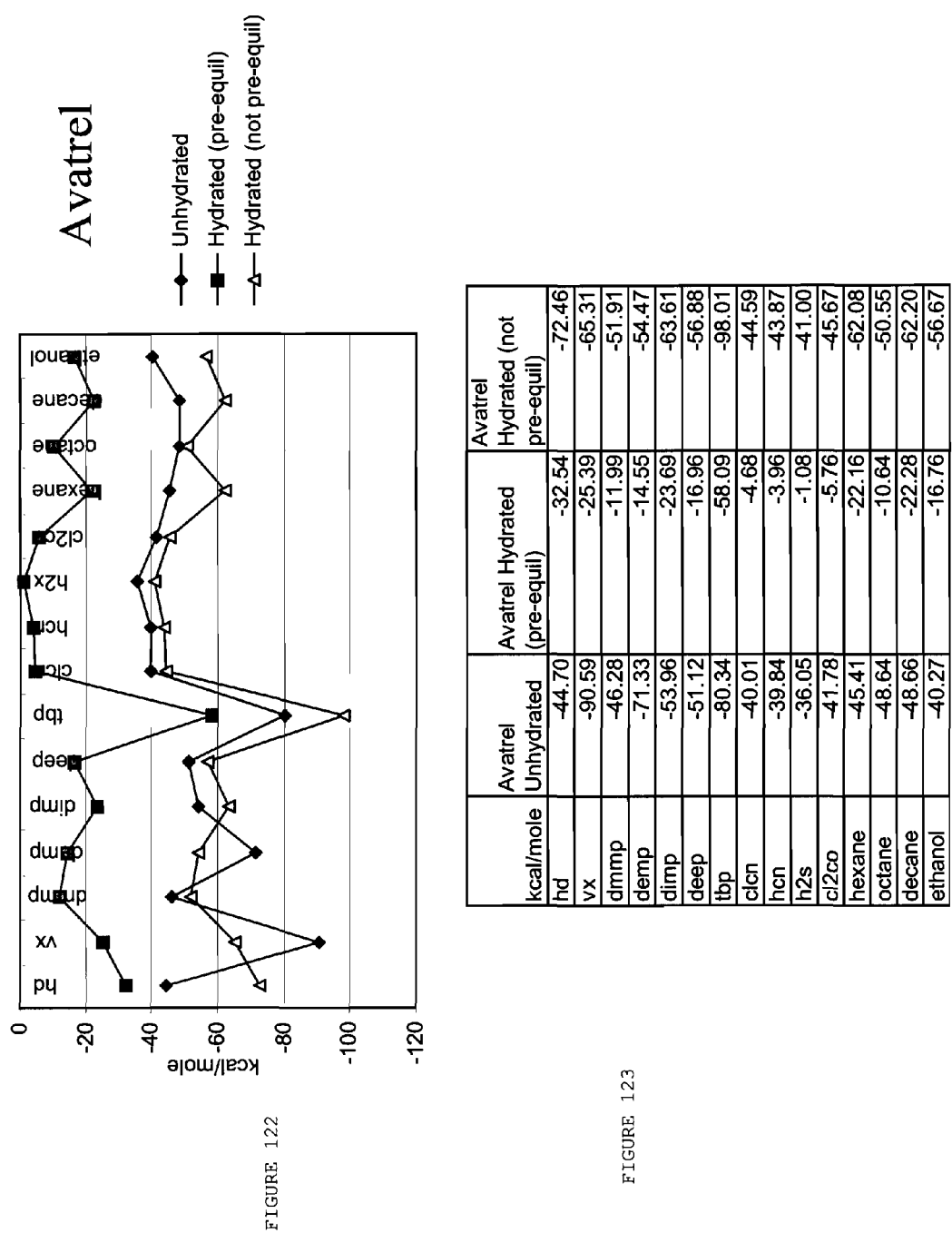
Figures 124, 125:
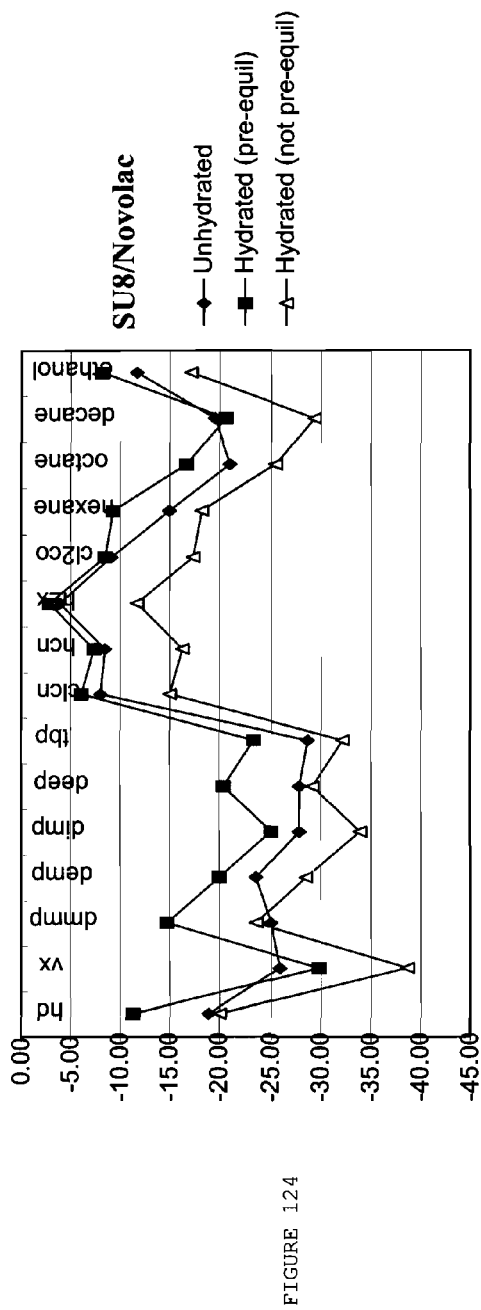
Figures 126, 127:
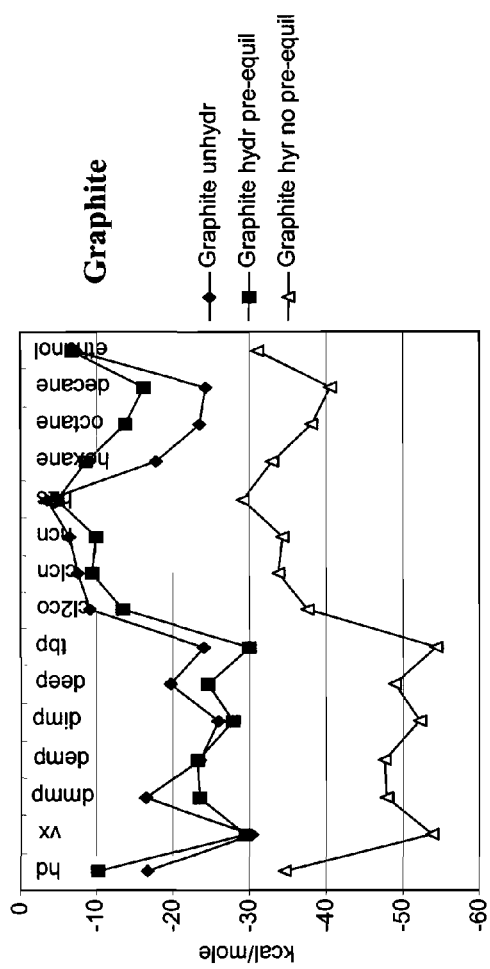

An anomalous point in FIG. 58 may be due to non pre-equilibrated hydration. Specific compounds may be labelled in FIG. 59-61. FIGS. 62 and 63 may provide a data summary. An unhydrated case may be more consistent in energy trends than a hydrated case. Across the data, separation doesn't appear so definitive, but appears to be due to hydration effect.

FIGS. 64-91 may relate to adsorption energies of CWA's. The models were derived from the Nanoglass model on the SiOH side. The nanoglass surfaces were substituted to represent effect of a bisperfluorobutanol silyl group on nanoglass, effect of a trifluoropropyl Methyl silyl group on nanoglass;

effect of a difluoropropanol Methyl silyl group on nanoglass, and the effect of the HON "TA"=dimethyl silyl group on nanoglass.

Observations appeared to indicate that the TA group is not as good as the standard nanoglass in reducing effect of water variability. It appears that fluorination of the side chain appears to help the water variability. Of the new surfaces, the trifluoropropyl methyl group appears to show the least effect of water, although the bisperfluorobutanol group looks very consistent also. There may be a hydrophobicity balance of side chain (the difluoropropanol group appears not as good as the trifluropropyl group). There may be target treatments for silica surfaces to consider. Available commercially are trifluoroprophymethylcyclotrisiloxane, trifluoropropylmethyl dichlorosilane; heptadecafluorotetrahydrodecylmethyldichlorosilane; tridecafluorotetrahydrooctylmethyldichlorosilane; Nanoglass™ and "TA". Plots may use unhydrated vs. hydrated. One may want a slope=1, intersecting at 0,0 in order to show no effect of water, relative to FIGS. 64-66. TA appears the worst for trend. The may be plots of unhydrated vs. hydrated for different adsorbers relative to FIGS. 67-71. Here, one may want a slope=1, intersecting at 0,0. One may note energies vs. MW.

FIGS. 92-102 may relate to CWA on Tetrafluoroethylene (TFE). Observations may include this being considered as an extreme case of a fluorocarbon surface. There may be a similar trend response to CWA in both hydration cases as the unhydrated. The pre-equilibrated water case may have similar energy ranges as unhydrated. The no-equilibrated water case appears to still have similar energy trends, but energy range seems shifted to larger adsorption. However, the large differences seem to appear between hydration state. The fluorocarbon substituted nanoglass still appears to look better in this respect.

FIGS. 103-110 appear to regard to Avatrel and SU8 stationary phases. The models may involve two new polymer stationary phases modeled. Avatrel may be based upon a polynorbornene polymer. It may be usually functionalized for adhesion. SU8 may be a standard stationary phase and be based on a novolac-epoxy. For these models, a cycloaliphatic epoxy (bis epoxy cyclohexylmethyladipate) version may be used for simulation.

Some observations may regard the following items. There seems to be surprising high energy adsorptivity of the cycloaliphatic Avatrel polymer, but low separation of energies of the analytes. The SU8/Novolac simulant using a cycloaliphatic epoxy may also be surprising in that water interference appears to be almost gone, and looks to have a good separation of groups of materials. The SU8 appears to show three distinct separation areas: <~10 kcal/mole small molecules; ~10-20 kcal/mole nonpolar molecules; >~20 polar molecules. These results, along with the other results seem to suggest that if one has high hydrophobicity (GX3P, CNT/Graphite, Avatrel), one may have a stationary phase with high adsorptivity. If one has polar content, one may see separation (SU8, NG-SiOH side, Teflon). If one removes potential hydrogen-bonding hydrogens, water interference may diminish (NG-SiO side, GX3P, CNT/Graphite, Teflon, Trifluoroprop-NG).

A stationary phase need may involve high hydrophobicity for high adsorptivity magnitude, low content of H-bond ability hydrogens for low water interference, and polar content for separation. Overall, SU8 may have the best balance of properties so far. Models may be run for epoxy-substituted Avatrel, as this could add the sufficient polarity for separation and one may look for the tradeoff of polar content to the adsorption magnitude.

An unhydrated vs. hydrated energy comparison may indicate good large magnitude adsorption energies for the CWAs in unhydrated state, "not pre-equilibrated" tracks best with unhydrated case, and may make a good collector phase.

The novolac epoxy may have very good retention of trends when hydrated and appears to be the best aspect of this material. It appears to have little difference between the two different hydration states.

Energy magnitudes appear similar to other stationary phases. The two polymers may have in common high hydrophobicity and cycloaliphatic content.

FIGS. 111-127 may relate to DB1 and comparisons. A new model stationary phase may concern DB1 (PDMS) with CWA series and some hydrocarbons.

Observations may indicate that DB1 adsorption energy range appears a little worse than NGE and about the same as treated NGE. Polynorbornene seems to still have the best absolute adsorption energies, followed by SU8 and Graphite. In general for adsorptivity: Polynorbornene>SU8~Graphite~NGE>DB1~dimethylsubstituted-NGE~tetrafluoroethylene~trifluoropropylsubst-NGE.

There seems to be little change in adsorption energy with moisture with the exception of HCN. For retention of energies comparing unhydrated and hydrated (pre-equil of water assumed), one may note that DB1, SU8, tetrafluoroethylene and Trifluoropropyl-subst-NGE and graphite appear better than polynorbornene, NGE and dimethyl substituted NGE.

The more hydrophobic materials appear to still have the best performance overall. For the Si-based compounds, the most hydrophobic (e.g., DB1) appear to be the ones that have less effect of water. Hydrophobicity may be expected to increase: NGE<Trifluoropropyl Subst NGE<DB1. However, there may not be a clear dielectric constant trend. For example, NGE and SU8 should have higher dielectric constants than PDMS (DB1) and polynorbornene should have a low dielectric constant.

The following indicate some nomenclature that may be relevant herein. Some possible stationary phase materials may include DB-1 (100% PDMS), DB-5 (PDMS with 5% phenyl), F-100 (VINAR7, a polysiloxane copolymer with dimethylsiloxane and silylarylene monomers), NGE (Nanoglass-E™, a nano-porous organosilicate), OV1 (PDMS), OV225 (cyano propyl methyl phenylmethyl silicone), OV275 (dicyano allyl silicone), PCUT (polycarbonate urethane), PDMS (polydimethylsiloxane), PECH (polyepicholorohydrine) PEVA (polyethylene-co-vinylacetate with 40% acetate), RTX-1 (100% PDMS by Restek™), RTX-200 (PDMS with trifluoropropyl addition) RTX-2330 (90% biscyanopropyl with 10% phenyl-cyanopropyl), SE-54 (DB-5), SOG (spin-on glass), and SXFA (siloxane flouoro alcohol).

A summary of some acronyms of interest may include CID (chemical impedance detector), DEEP (diethyl ethyl phosphonate), DMMP (dimethyl methyl phosphonate), FID (flame ionization detector), GC (gas chromatograph(y)), IDHL (immediately dangerous to health and life), MEMS (micro-elecro-mechanical structure or system), MDD (microdischarge detector(, MDL (minimum detection limit), MS (mass spectrometer), PC (pre-concentration), PHASED (phased heater array structure for enhanced detection), SAW (surface-acoustic wave), TCD (thermal conductivity detector), TLS (total logarithmic sensitivity), and TME (total maximum error).

Some symbols of interest may include H (height of theoretical plate for GC separation in cm or μm), ΔH (enthalpy of vaporization or desorption in kJ/mol or kcal/mol; $\log_e(k')=\Delta H/RT+\Delta S/R-\ln(\beta)$), k' (capacity or retention factor, dimensionless), K (partition or equilibrium coefficient, K=k'·β), L (length of GC separation column in cm or m), ΔS (entropy of vaporization or desorption in kJ/(K·mol) or kcal/(K·mol)), $t_o$ (elution time with zero retention in the column in s or ms), $t_r$ (elution time with retention in s or ms), $T_b$ (boiling point temperature in K or ° C.), v (velocity in cm/s or m/s), w (width of a GC peak at half height in s or ms), β (volumetric ratio of (gas phase)/(stationary phase) of a GC column), and ε (relative dielectric constant).

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A method for making a stationary phase for a fluid analyzer, comprising:
    selecting a material, and wherein selecting a material includes utilizing computer based molecular modeling and qualitatively comparing interactions from a molecular scale; and
    applying the material on a support member; wherein the material comprises a hydrophobic polymer and a porous dielectric having a toughening agent that uses a neutral leaving group and has:
        an adsorption energy that monotonically increases with molecular weight or boiling point; and
        a potential activity to resist water interference during adsorption; and
    wherein the polymer comprises: polynorbornene; polytetrafluoroethylene;
        fluorinated polyolefins; and/or novolac resins.

2. The method of claim 1, wherein the material further has:
    a nonpolar property; and
    a temperature tolerance greater than 200 degrees C.

3. The method of claim 1, wherein the material comprises an organic low k dielectric.

4. The method of claim 1, wherein the material comprises nanotubes.

5. The method of claim 1, wherein the material is a composite comprising a low k inorganic and a low k organic mixture.

* * * * *